US011656230B2

(12) United States Patent
Cardone

(10) Patent No.: US 11,656,230 B2
(45) Date of Patent: *May 23, 2023

(54) METHOD FOR PREDICTING CANCER SENSITIVITY

(71) Applicant: Eutropics Pharmaceuticals, Inc., Cambridge, MA (US)

(72) Inventor: Michael H. Cardone, Dorchester, MA (US)

(73) Assignee: Eutropics Pharmaceuticals, Inc., Cambridge, MA (US)

(*) Notice: Subject to any disclaimer, the term of this patent is extended or adjusted under 35 U.S.C. 154(b) by 303 days.

This patent is subject to a terminal disclaimer.

(21) Appl. No.: 16/912,087

(22) Filed: Jun. 25, 2020

(65) Prior Publication Data

US 2020/0393468 A1 Dec. 17, 2020

Related U.S. Application Data

(63) Continuation of application No. 14/909,373, filed as application No. PCT/US2014/049420 on Aug. 1, 2014, now Pat. No. 10,732,182.

(60) Provisional application No. 61/861,009, filed on Aug. 1, 2013.

(51) Int. Cl.
*G01N 31/00* (2006.01)
*G01N 33/53* (2006.01)
*G01N 33/574* (2006.01)
*C07K 16/40* (2006.01)

(52) U.S. Cl.
CPC ....... *G01N 33/57496* (2013.01); *C07K 16/40* (2013.01); *G01N 33/574* (2013.01); *G01N 33/57488* (2013.01); *C07K 2317/622* (2013.01); *G01N 2333/96466* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,856,445 A | 1/1999 | Korsmeyer |
| 5,955,593 A | 9/1999 | Korsmeyer |
| 5,998,583 A | 12/1999 | Korsmeyer |
| 6,165,732 A | 12/2000 | Korsmeyer et al. |
| 6,258,540 B1 | 7/2001 | Lo et al. |
| 6,326,354 B1 | 12/2001 | Gross et al. |
| 7,026,456 B1 | 4/2006 | Gately et al. |
| 7,247,700 B2 | 7/2007 | Korsmeyer et al. |
| 7,345,700 B2 | 3/2008 | Nortrup |
| 7,723,469 B2 | 5/2010 | Walensky et al. |
| 7,755,765 B2 | 7/2010 | Post et al. |
| 7,829,662 B2 | 11/2010 | Korsmeyer et al. |
| 7,868,133 B2 | 1/2011 | Korsmeyer et al. |
| 7,871,769 B2 | 1/2011 | Baker et al. |
| 8,168,755 B2 * | 5/2012 | Cardone .......... G01N 33/57492 530/389.1 |
| 8,198,405 B2 | 6/2012 | Walensky et al. |
| 8,221,966 B2 | 7/2012 | Letai |
| 8,323,987 B2 | 12/2012 | Threadgill et al. |
| 2002/0177692 A1 | 11/2002 | Bartel et al. |
| 2003/0073661 A1 | 4/2003 | Matsuyama et al. |
| 2003/0181404 A1 | 9/2003 | Avraham et al. |
| 2004/0171809 A1 | 9/2004 | Korsmeyer et al. |
| 2004/0241902 A1 | 10/2004 | Wang et al. |
| 2005/0191696 A1 | 9/2005 | Goldmakher et al. |
| 2006/0183687 A1 | 8/2006 | Cory et al. |
| 2008/0104721 A1 | 5/2008 | Barsova et al. |
| 2008/0199890 A1 | 8/2008 | Letai |
| 2008/0300239 A1 | 12/2008 | Adams et al. |
| 2009/0005416 A1 | 1/2009 | Munchhof et al. |
| 2009/0030005 A1 | 1/2009 | Kamb et al. |
| 2009/0280510 A1 | 11/2009 | Cardone et al. |
| 2010/0015058 A1 | 1/2010 | Li et al. |
| 2011/0008371 A1 | 1/2011 | Michelson |
| 2011/0071042 A1 | 3/2011 | Kim et al. |
| 2011/0154522 A1 | 6/2011 | Korsmeyer et al. |
| 2011/0301193 A1 | 12/2011 | Errico et al. |
| 2012/0041070 A1 | 2/2012 | Jin et al. |
| 2012/0172371 A1 | 7/2012 | Pommier et al. |
| 2012/0196853 A1 | 8/2012 | Durrenberger et al. |
| 2012/0225794 A1 | 9/2012 | Cardone et al. |

(Continued)

FOREIGN PATENT DOCUMENTS

| | | |
|---|---|---|
| CN | 1583776 A | 2/2005 |
| WO | 96/13614 A1 | 5/1996 |
| WO | 96/15263 A1 | 5/1996 |

(Continued)

OTHER PUBLICATIONS

Yamanaka et al. (Molecular Cancer Ther., 2005, vol. 4, No. 11, pp. 1689-1698) (Year: 2005).*
Bellows et al. (Journal of Virology, Jun. 2000, vol. 74, No. 11, pp. 5024-5031). (Year: 2000).*
Reed et al. (Blood, 2008, vol. 111, No. 7, pp. 3322-3330). (Year: 2008).*
Yang et al. (Cancer Research, vol. 63, 2003, pp. 6815-6824) (Year: 2003).*
International Search Report, PCT appl. No. PCT/US2014/049420, 4 pages (dated Dec. 11, 2014).
Written Opinion of the International Seaching Authority, PCT appl. No. PCT/US2014/049420, 5 pages (dated Dec. 11, 2014).

(Continued)

*Primary Examiner* — Lisa V Cook
(74) *Attorney, Agent, or Firm* — Morgan, Lewis & Bockius LLP

(57) ABSTRACT

The present invention relates to methods of determining cancer cell sensitivity to treatment by using antibodies to detect the presence of heterodimers in the cell, as well as to determine the relationship between the antibody binding to the heterodimer in the cancer cell and the sensitivity of the cell to cancer treatment. The invention also provides a method of predicting therapeutic efficacy in a cancer patient.

11 Claims, 18 Drawing Sheets

Specification includes a Sequence Listing.

(56) References Cited

U.S. PATENT DOCUMENTS

| | | |
|---|---|---|
| 2012/0225851 A1 | 9/2012 | Cardone et al. |
| 2013/0079424 A1 | 3/2013 | Gerber et al. |

FOREIGN PATENT DOCUMENTS

| | | | |
|---|---|---|---|
| WO | 1998/009643 A1 | 3/1998 | |
| WO | 1998/009980 A1 | 3/1998 | |
| WO | 1998/017682 A1 | 4/1998 | |
| WO | 1999/016787 A9 | 4/1999 | |
| WO | 2000/006187 A2 | 2/2000 | |
| WO | 2000/011162 A2 | 2/2000 | |
| WO | 2002/005835 A2 | 1/2002 | |
| WO | 2003/057158 A2 | 7/2003 | |
| WO | 2004/022580 A2 | 3/2004 | |
| WO | WO-2004066958 A2 * | 8/2004 | ......... A61K 47/6923 |
| WO | 2004/074218 A2 | 9/2004 | |
| WO | 2004/080463 A1 | 9/2004 | |
| WO | 2004/087887 A2 | 10/2004 | |
| WO | 2005/028444 A1 | 3/2005 | |
| WO | 2005/044839 A2 | 5/2005 | |
| WO | 2005/049576 A1 | 6/2005 | |
| WO | 2007/123791 A9 | 1/2007 | |
| WO | 2008/021484 A2 | 2/2008 | |
| WO | 2010/042163 A2 | 4/2010 | |
| WO | 2010/093742 A2 | 8/2010 | |
| WO | 2010/107765 A1 | 9/2010 | |
| WO | 2010/143168 A2 | 12/2010 | |
| WO | 2011/020886 A1 | 2/2011 | |
| WO | 2011/085126 A2 | 7/2011 | |
| WO | 2011/088137 A2 | 7/2011 | |
| WO | 2011/094708 A2 | 8/2011 | |
| WO | 2011/127333 A1 | 10/2011 | |
| WO | 2012/012653 A1 | 1/2012 | |
| WO | 2012/122370 A1 | 9/2012 | |
| WO | WO 2012/122370 A2 | 9/2012 | |

OTHER PUBLICATIONS

KG-Ia (ATCC® CCL-246.1™) ATCC Product Sheet, 3 pages (2013).
Adlard, et al., "Prediction of the response of colorectal cancer to systemic therapy," Lancet Oncol. 3:75-82 (2002).
Bhat, S. et al., "Substituted Oxines Inhibit Endothelial Cell Proliferation and Angiogenesis", Organic & Biomolecular Chemistry (2012) 10(15):2979-2992.
Bodet, et al., "BH3-only protein Bik is involved in both apoptosis induction and sensitivity to oxidative stress in multiple myeloma," Br. J. Cancer 103:1808-1814 (2010).
Campbell, et al., "General properties and applications of monoclonal antibodies," Monoclonal Antibody Technology, pp. 1-32 (1984).
Certo, et al., "Mitochondria Primed by Death Signals Determine Cellular Addiction to Antiapoptotic BCL-2 Family Members," Cancel Cell 9:351-365 (May 2006).
Chonghaile, et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1142, 53rd ASH Annual Meeting and Exposition, Dec. 10-13, 2011, American Society of Hematology.
Chonghaile, et al., "Pretreatment Mitochondrial Priming Correlates with Clinical Response to Cytotoxic Chemotherapy," Science 334:1129-1133, including supporting material (2011).
Cimmino, et al., "miR-15 and miR-16 induce apoptosis by targeting BCL2," Proc. Natl. Acad. Sci. USA 102 (39):13944-13945 (2005).
Colman, "Effects of amino acid sequence changes on antibody-antigen interactions," Res. Immunol. 145"33-36 (1994).
Combaret, V. et al., Effect of Bortezomib on Human Neuroblastoma: Analysis of Molecular Mechanisms Involved in Cytotoxicity, Molecular Cancer, Jun. 5, 2008, vol. 7, No. 50; DOI:10.1186/1476-4598-7-50.
Davids, et al., "BH3 Profiling Demonstrates That Restoration of Apoptotic Priming Contributes to Increased Sensitivity to P13K Inhibition on Stroma-Exposed Chronic Lymphocytic Leukemia Cells," Blood 118: Abstract 974 (2011).
Del Gaizo Moore, et al., "BH3 profiling—measuring intergrated function of the mitochondrial apoptotic to predict cell fate decisions," Cancer Lett. 332(2):202-205 (2013).
Del Gaizo Moore, et al., "Chronic lymphocytic leukemia requires BCL2 to sequester prodeath BIM, explaining sensitivity to BCL2 antagonist ABT-737," J. Clin. Invest. 117(1):112-121 (2007).
Deng, et al., "BH3 Profiling Identifies Three Distinct Classes of Apoptotic Blocks to Predict Response to ABT-737 and Conventional Chemotherapeutic Agents," Cancel Cell 12:171-185 (2007).
Fidler, Tumor Heterogeneity and the Biology of Cancer Invasion andMetastasis, (Cancer Res 1978; 38:2651-2660).
Hann, et al., "Therapeutic Efficacy of ABT-737, a Selective Inhibitor of BCL-2, in Small Cell Lung Cancer," Cancer Res. 68:2321-2328 (2008).
Kasper, et al., "Targeting MCL-1 sensitizes FLT3-ITD-positive leukemias to cytotoxic therapies," Blood Cancer J. 2:10 pages (2012).
Letai, et al., "Antiapoptotic BCL-2 is required for maintenance of a model leukemia," Cancer Cell, 6:241-249 (2004).
Letai, et al., "Diagnosing and exploiting cancer's addiction to blocks in apoptosis," Nat. Rev. Cancer 8:121-132 (2008).
Liu, et al., "The Structure of a Bcl-xL/Bim Fragment Complex: Implications for Bim Function," Immunity, vol. 19, 341-352, Sep. 2003.
Lupo, B. et al. "Lenalidomide in the Treatment of Young Patients with Multiple Myeloma: From Induction to Consolidation/Maintenance Therapy", Advances in Hematology, Jul. 11, 2012, vol. 2012, ID No. 906247, pp. 1-6.
Maccallum et al., "Antibody-antigen Interactions: Contact Analysis and Binding Site Topography," J. Mol. Biol. 262:732-745 (1996).
Miller, et al., "Therapeutic Strategies to Enhance the Anticancer Efficacy of Histone Deacetylase Inhibitors," J. Biomed Biotechnol. 2011:17 pages (2011).
Mohammad et al., "Nonpeptidic Small-Molecule Inhibitor of Bcl-2 and Bcl-XL, (-)-Gossypol, Enhances Biological Effect of Genistein Against BxPC-3 Human Pancreatic Cancer Cell Line," Pancreas, vol. 31, No. 4, Nov. 2005, pp. 317-324.
Neidle, Stephen, ed. :Cancer Drug Design and Discover, Elsevier/Academic Press, 2008, p. 431.
Paoluzzi, et al., "The BH3-only mimetic ABT-737 synergizes the antineoplastic activity of proteasome inhibitors in lymphoid malignancies," Blood 112:2906-2916 (2008).
Patani and Lavoie, "Bioisosterism: A Rational Approach in Drug Design", Chem. Rev. 1996, 96, 3147-3176.
Paul, "Fundamental Immunology," 3rd Edition, Raven Press, Ltd., pp. 292-295 (1993).
Pierceall, et al., "BH3 Profiling Discriminates Response to Cytarabine-Based Treatment of Acute Myelogenous Leukemia," Mol. Cancer Ther. 12(12):2940-2949 (2013).
Pode-Shakked, et al., "Developmental tumourigenesis: NCAM as a putative marker for the malignant renal stem/progenitorcell population," J. Cell. Mol. Med. 13(88):1792-1808 (2009).
Pritzker, et al., "Cancer Biomarkers: Easier Said Than Done," Clin. Chem. 48(8):1147-1150 (2002).
PUBCHEM Compound ID 49790728, Create Date Dec. 15, 2010 (online), retrieved on Aug. 3, 2012; http://pubchem.ncbi.nim.nih.gov/sumary/summary.cgi?cid+49790728.
Qin, Jie et al., "Identification of a Novel Family of BRAFV600E Inhibitors", J. Med. Chem. 2012, 55(11):5220-5230.
Raychaudhuri, et al., "Low probability Bid-Bax reaction generates heterogeneit in apoptosis resistance of cancer and cancer stem cells," arXiv:1108.209 [q-bio.MN], 17 pages (2011).
Rudikoff, et al., "Single amino acid substitution altering antigen-binding specificity," Proc. Natl. Acad. Sci. USA 79:1979-1983 (1982).
Sinicrope, et al., "Proapoptotic Bad and Bid Protein Expression Predict Survival in Stages II and III Colon Cancers," Clin. Canc. Res. 14(13):4128-4133 (2008).
Sinicrope, et al., "Prognostic Impact of Bim, Puma, and Noxa Expression in Human Colon Carcinomas," Clin. Canc. Res. 14(18):5810-5818 (2008).

(56) References Cited

OTHER PUBLICATIONS

Stewart, et al., "The MCL-1 BH3 Helix is an Exclusive MCL-1 inhibitor and Apoptosis Sensitizer," Nat. Chem. Biol. 6(8):595-601 (2010).

Strigacova et al., "Some Biological Properties of New Quinoline-4-carboxylic Acid and Quinoline-4 Carboxamide Derivatives", Folia Microbiol (Praha) 2000, 45(4):305-9.

Taussig, et al., "Anti-CD38 antibody-mediated clearance of human repopulating cells masks the heterogeneity of leukemia-initiating cells," Blood 112:568-575 (2008).

Thomenius, et al., "Using BH3 Profiling As a Predictive Indicator for Myeloma Patient Response to Bortezomib," Blood 118(21):abstract No. 3952 (2011).

Valencia, et al., "A new reliable fluorescence in situ hybridization method for identifying multiple specific cytogenetic abnormalities in acute myeloid leukemia," Leukemia & Lymphoma 51 (4):680-685 (2010).

Vo, "Mitchondrial Priming Determines Chemotherapeutic Response in Acute Myeloid Leukemia," Disseration, Harvard University, UMI No. 3514220, 119 pages (2012).

Vo, "Relative Mitochondrial Priming of Myeloblasts and Normal HCSs Detemines Chemotherapeutic Success in AML," Cell 151(2):344-355 (2012).

Weniger, et al., "Treatment-Induced Oxidative Stress and Cellular Antioxidant Capacity Determine Response to Bortezomib in Mantel Cell Lymphoma," Clin. Canc. Res. 17(15):5101-5112 (2011).

\* cited by examiner

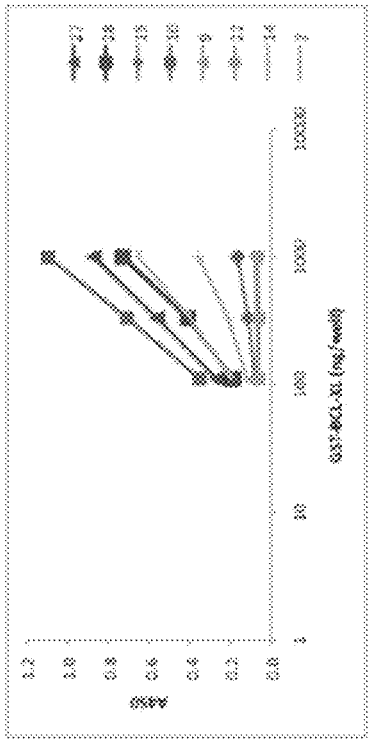
FIGURE 11A
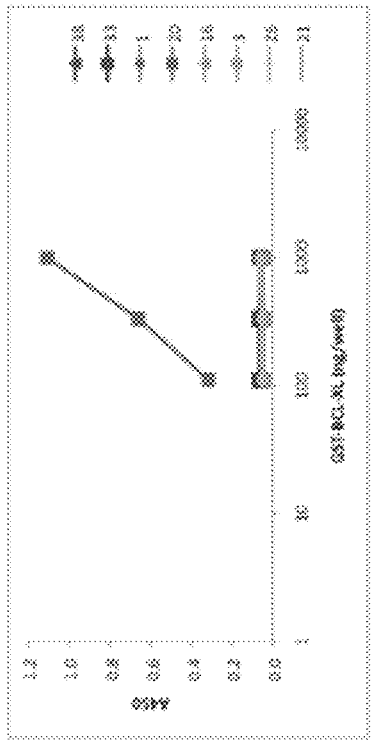
FIGURE 11B
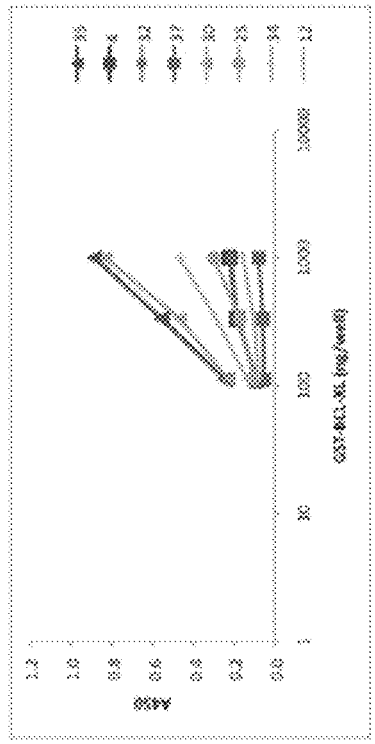
FIGURE 11C
FIGURE 11D

6. TMB reagent

5. HRP-conj. secondary ab 4. monoclonal antibody clone

3. GST-Bcl-XL

2. Biotinylated peptide

1. Streptavidin coated plate

SEQUENCE LISTING

<160> NUMBER OF SEQ ID NOS: 26

<210> SEQ ID NO 1
<211> LENGTH: 239
<212> TYPE: PRT
<213> ORGANISM: Homo sapiens

<400> SEQUENCE: 1

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 2
<211> LENGTH: 233
<212> TYPE: PRT
<213> ORGANISM: homo sapiens

<400> SEQUENCE: 2

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu

```
                   85                  90                  95

Phe Glu Leu Arg Tyr Arg Arg Ala Phe Ser Asp Leu Thr Ser Gln Leu
                100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
        130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 3
<211> LENGTH: 350
<212> TYPE: PRT
<213> ORGANISM: Homo sapiens

<400> SEQUENCE: 3

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220
```

```
Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
            245                 250                 255

Gly Val Thr Asn Trp Gly Arg Ile Val Thr Leu Ile Ser Phe Gly Ala
        260                 265                 270

Phe Val Ala Lys His Leu Lys Thr Ile Asn Gln Glu Ser Cys Ile Glu
    275                 280                 285

Pro Leu Ala Glu Ser Ile Thr Asp Val Leu Val Arg Thr Lys Arg Asp
290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 4
<211> LENGTH: 193
<212> TYPE: PRT
<213> ORGANISM: Homo sapiens

<400> SEQUENCE: 4

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys

<210> SEQ ID NO 5
<211> LENGTH: 175
<212> TYPE: PRT
<213> ORGANISM: Homo sapiens

<400> SEQUENCE: 5

Met Thr Asp Cys Glu Phe Gly Tyr Ile Tyr Arg Leu Ala Gln Asp Tyr
```

-continued

```
                1               5                  10                 15
            Leu Gln Cys Val Leu Gln Ile Pro Gln Pro Gly Ser Gly Pro Ser Lys
                            20                 25                 30

Thr Ser Arg Val Leu Gln Asn Val Ala Phe Ser Val Gln Lys Glu Val
                            35                 40                 45

Glu Lys Asn Leu Lys Ser Cys Leu Asp Asn Val Asn Val Val Ser Val
                        50                 55                 60

Asp Thr Ala Arg Thr Leu Phe Asn Gln Val Met Glu Lys Glu Phe Glu
             65                 70                 75                 80

Asp Gly Ile Ile Asn Trp Gly Arg Ile Val Thr Ile Phe Ala Phe Glu
                                85                 90                 95

Gly Ile Leu Ile Lys Lys Leu Leu Arg Gln Gln Ile Ala Pro Asp Val
                            100                105                110

Asp Thr Tyr Lys Glu Ile Ser Tyr Phe Val Ala Glu Phe Ile Met Asn
                            115                120                125

Asn Thr Gly Glu Trp Ile Arg Gln Asn Gly Gly Trp Glu Asn Gly Phe
                            130                135                140

Val Lys Lys Phe Glu Pro Lys Ser Gly Trp Met Thr Phe Leu Glu Val
            145                150                155                160

Thr Gly Lys Ile Cys Glu Met Leu Ser Leu Leu Lys Gln Tyr Cys
                            165                170                175

<210> SEQ ID NO 6
<211> LENGTH: 192
<212> TYPE: PRT
<213> ORGANISM: Homo sapiens

<400> SEQUENCE: 6

Met Asp Gly Ser Gly Glu Gln Pro Arg Gly Gly Gly Pro Thr Ser Ser
             1               5                  10                 15

Glu Gln Ile Met Lys Thr Gly Ala Leu Leu Leu Gln Gly Phe Ile Gln
                            20                 25                 30

Asp Arg Ala Gly Arg Met Gly Gly Glu Ala Pro Glu Leu Ala Leu Asp
                            35                 40                 45

Pro Val Pro Gln Asp Ala Ser Thr Lys Lys Leu Ser Glu Cys Leu Lys
                        50                 55                 60

Arg Ile Gly Asp Glu Leu Asp Ser Asn Met Glu Leu Gln Arg Met Ile
             65                 70                 75                 80

Ala Ala Val Asp Thr Asp Ser Pro Arg Glu Val Phe Phe Arg Val Ala
                                85                 90                 95

Ala Asp Met Phe Ser Asp Gly Asn Phe Asn Trp Gly Arg Val Val Ala
                            100                105                110

Leu Phe Tyr Phe Ala Ser Lys Leu Val Leu Lys Ala Leu Cys Thr Lys
                            115                120                125

Val Pro Glu Leu Ile Arg Thr Ile Met Gly Trp Thr Leu Asp Phe Leu
                            130                135                140

Arg Glu Arg Leu Leu Gly Trp Ile Gln Asp Gln Gly Gly Trp Asp Gly
            145                150                155                160

Leu Leu Ser Tyr Phe Gly Thr Pro Thr Trp Gln Thr Val Thr Ile Phe
                            165                170                175

Val Ala Gly Val Leu Thr Ala Ser Leu Thr Ile Trp Lys Lys Met Gly
                            180                185                190

<210> SEQ ID NO 7
<211> LENGTH: 211
```

```
<212> TYPE: PRT
<213> ORGANISM: Homo sapiens

<400> SEQUENCE: 7

Met Ala Ser Gly Gln Gly Pro Gly Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
        35                  40                  45

Ala Glu Gly Val Ala Ala Pro Ala Asp Pro Glu Met Val Thr Leu Pro
    50                  55                  60

Leu Gln Pro Ser Ser Thr Met Gly Gln Val Gly Arg Gln Leu Ala Ile
65              70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
        115                 120                 125

Val Ala Leu Leu Gly Phe Gly Tyr Arg Leu Ala Leu His Val Tyr Gln
    130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205

Phe Lys Ser
    210

<210> SEQ ID NO 8
<211> LENGTH: 168
<212> TYPE: PRT
<213> ORGANISM: Homo sapiens

<400> SEQUENCE: 8

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65              70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125
```

-continued

```
Leu Pro Arg Pro Lys Ser Ala Gly Thr Ala Thr Gln Met Arg Gln Ser
        130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 9
<211> LENGTH: 160
<212> TYPE: PRT
<213> ORGANISM: Homo sapiens

<400> SEQUENCE: 9

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
                20                  25                  30

Thr Asp Ser Glu Glu Asp Leu Asp Pro Met Glu Asp Phe Asp Ser Leu
            35                  40                  45

Glu Cys Met Glu Gly Ser Asp Ala Leu Ala Leu Arg Leu Ala Cys Ile
    50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Ala Leu Leu Leu Leu Leu Leu
    130                 135                 140

Ala Leu Leu Leu Pro Leu Leu Ser Gly Gly Leu His Leu Leu Leu Lys
145                 150                 155                 160

<210> SEQ ID NO 10
<211> LENGTH: 54
<212> TYPE: PRT
<213> ORGANISM: Homo sapiens

<400> SEQUENCE: 10

Met Pro Gly Lys Lys Ala Arg Lys Asn Ala Gln Pro Ser Pro Ala Arg
1               5                   10                  15

Ala Pro Ala Glu Leu Glu Val Glu Cys Ala Thr Gln Leu Arg Arg Phe
                20                  25                  30

Gly Asp Lys Leu Asn Phe Arg Gln Lys Leu Leu Asn Leu Ile Ser Lys
            35                  40                  45

Leu Phe Cys Ser Gly Thr
    50

<210> SEQ ID NO 11
<211> LENGTH: 91
<212> TYPE: PRT
<213> ORGANISM: Homo sapiens

<400> SEQUENCE: 11

Met Cys Pro Cys Pro Leu His Arg Gly Arg Gly Pro Pro Ala Val Cys
1               5                   10                  15

Ala Cys Ser Ala Gly Arg Leu Gly Leu Arg Ser Ser Ala Ala Gln Leu
```

```
            20                  25                  30

Thr Ala Ala Arg Leu Lys Ala Leu Gly Asp Glu Leu His Gln Arg Thr
        35                  40                  45

Met Trp Arg Arg Arg Ala Arg Ser Arg Arg Ala Pro Ala Pro Gly Ala
 50                  55                  60

Leu Pro Thr Tyr Trp Pro Trp Leu Cys Ala Ala Ala Gln Val Ala Ala
 65                  70                  75                  80

Leu Ala Ala Trp Leu Leu Gly Arg Arg Asn Leu
                 85                  90

<210> SEQ ID NO 12
<211> LENGTH: 184
<212> TYPE: PRT
<213> ORGANISM: Homo sapiens

<400> SEQUENCE: 12

Met Glu Pro Ser Gln Cys Val Glu Glu Leu Glu Asp Asp Val Phe Gln
 1               5                  10                  15

Pro Glu Asp Gly Glu Pro Val Thr Gln Pro Gly Ser Leu Leu Ser Ala
                 20                  25                  30

Asp Leu Phe Ala Gln Ser Leu Leu Asp Cys Pro Leu Ser Arg Leu Gln
            35                  40                  45

Leu Phe Pro Leu Thr His Cys Cys Gly Pro Gly Leu Gln Pro Thr Ser
 50                  55                  60

Gln Glu Asp Lys Ala Thr Gln Thr Leu Ser Pro Ala Ser Pro Ser Gln
 65                  70                  75                  80

Gly Val Met Leu Pro Cys Gly Val Thr Glu Glu Pro Gln Arg Leu Phe
                 85                  90                  95

Tyr Gly Asn Ala Gly Tyr Arg Leu Pro Leu Pro Ala Ser Phe Pro Ala
            100                 105                 110

Val Leu Pro Ile Gly Glu Gln Pro Pro Glu Gly Gln Trp Gln His Gln
        115                 120                 125

Ala Glu Val Gln Ile Ala Arg Lys Leu Gln Cys Ile Ala Asp Gln Phe
    130                 135                 140

His Arg Leu His Val Gln Gln His Gln Gln Asn Gln Asn Arg Val Trp
145                 150                 155                 160

Trp Gln Ile Leu Leu Phe Leu His Asn Leu Ala Leu Asn Gly Glu Glu
                165                 170                 175

Asn Arg Asn Gly Ala Gly Pro Arg
            180

<210> SEQ ID NO 13
<211> LENGTH: 261
<212> TYPE: PRT
<213> ORGANISM: Homo sapiens

<400> SEQUENCE: 13

Lys Gln Tyr Arg Thr Val Arg Ser Gly Leu Leu Pro Pro Arg Pro Val
 1               5                  10                  15

Pro Ala Arg Arg Arg Pro Cys Leu Arg Leu Pro Pro Ala Ala Ala
                 20                  25                  30

Arg Trp Ala Phe Ser Leu Leu Pro Asn Arg Val Trp Ala Ser Ser Pro
            35                  40                  45

Arg Val Leu Val Thr Leu Asp Pro Gly Ala Glu Pro Trp His His Asp
 50                  55                  60

Ser Glu Ala Glu Thr Leu Ser Trp Ser His Pro Gly Glu Met Glu Pro
```

-continued

```
                 65                  70                  75                  80
Ser Gln Cys Val Glu Glu Leu Glu Asp Asp Val Phe Gln Pro Glu Asp
                     85                  90                  95

Gly Glu Pro Val Thr Gln Pro Gly Ser Leu Leu Ser Ala Asp Leu Phe
                100                 105                 110

Ala Gln Ser Leu Leu Asp Cys Pro Leu Ser Arg Leu Gln Leu Phe Pro
            115                 120                 125

Leu Thr His Cys Cys Gly Pro Gly Leu Arg Pro Thr Ser Gln Glu Asp
        130                 135                 140

Lys Ala Thr Gln Thr Leu Ser Pro Ala Ser Pro Ser Gln Gly Val Met
145                 150                 155                 160

Leu Pro Cys Gly Val Thr Glu Glu Pro Gln Arg Leu Phe Tyr Gly Asn
                165                 170                 175

Ala Gly Tyr Arg Leu Pro Leu Pro Ala Ser Phe Pro Ala Val Leu Pro
            180                 185                 190

Ile Gly Glu Gln Pro Pro Glu Gly Gln Trp Gln His Gln Ala Glu Val
        195                 200                 205

Gln Ile Ala Arg Lys Leu Gln Cys Ile Ala Asp Gln Phe His Arg Leu
    210                 215                 220

His Val Gln Gln His Gln Asn Gln Asn Arg Val Trp Trp Gln Ile
225                 230                 235                 240

Leu Leu Phe Leu His Asn Leu Ala Leu Asn Gly Glu Glu Asn Arg Asn
                245                 250                 255

Gly Ala Gly Pro Arg
            260

<210> SEQ ID NO 14
<211> LENGTH: 193
<212> TYPE: PRT
<213> ORGANISM: Homo sapiens

<400> SEQUENCE: 14

Met Ala Arg Ala Arg Gln Glu Gly Ser Ser Pro Glu Pro Val Glu Gly
1               5                   10                  15

Leu Ala Arg Asp Gly Pro Arg Pro Phe Pro Leu Gly Arg Leu Val Pro
            20                  25                  30

Ser Ala Val Ser Cys Gly Leu Cys Glu Pro Gly Leu Ala Ala Ala Pro
        35                  40                  45

Ala Ala Pro Thr Leu Leu Pro Ala Ala Tyr Leu Cys Ala Pro Thr Ala
    50                  55                  60

Pro Pro Ala Val Thr Ala Ala Leu Gly Gly Ser Arg Trp Pro Gly Gly
65                  70                  75                  80

Pro Arg Ser Arg Pro Arg Gly Pro Arg Pro Asp Gly Pro Gln Pro Ser
                85                  90                  95

Leu Ser Leu Ala Glu Gln His Leu Glu Ser Pro Val Pro Ser Ala Pro
            100                 105                 110

Gly Ala Leu Ala Gly Gly Pro Thr Gln Ala Ala Pro Gly Val Arg Gly
        115                 120                 125

Glu Glu Glu Gln Trp Ala Arg Glu Ile Gly Ala Gln Leu Arg Arg Met
    130                 135                 140

Ala Asp Asp Leu Asn Ala Gln Tyr Glu Arg Arg Arg Gln Glu Glu Gln
145                 150                 155                 160

Gln Arg His Arg Pro Ser Pro Trp Arg Val Leu Tyr Asn Leu Ile Met
                165                 170                 175
```

-continued

```
Gly Leu Leu Pro Leu Pro Arg Gly His Arg Ala Pro Glu Met Glu Pro
            180                 185                 190
Asn

<210> SEQ ID NO 15
<211> LENGTH: 4374
<212> TYPE: PRT
<213> ORGANISM: Homo sapiens

<400> SEQUENCE: 15

Met Lys Val Asp Arg Thr Lys Leu Lys Lys Thr Pro Thr Glu Ala Pro
1               5                   10                  15

Ala Asp Cys Arg Ala Leu Ile Asp Lys Leu Lys Val Cys Asn Asp Glu
            20                  25                  30

Gln Leu Leu Leu Glu Leu Gln Gln Ile Lys Thr Trp Asn Ile Gly Lys
        35                  40                  45

Cys Glu Leu Tyr His Trp Val Asp Leu Leu Asp Arg Phe Asp Gly Ile
    50                  55                  60

Leu Ala Asp Ala Gly Gln Thr Val Glu Asn Met Ser Trp Met Leu Val
65                  70                  75                  80

Cys Asp Arg Pro Glu Arg Glu Gln Leu Lys Met Leu Leu Leu Ala Val
                85                  90                  95

Leu Asn Phe Thr Ala Leu Leu Ile Glu Tyr Ser Phe Ser Arg His Leu
            100                 105                 110

Tyr Ser Ser Ile Glu His Leu Thr Thr Leu Leu Ala Ser Ser Asp Met
        115                 120                 125

Gln Val Val Leu Ala Val Leu Asn Leu Leu Tyr Val Phe Ser Lys Arg
    130                 135                 140

Ser Asn Tyr Ile Thr Arg Leu Gly Ser Asp Lys Arg Thr Pro Leu Leu
145                 150                 155                 160

Thr Arg Leu Gln His Leu Ala Glu Ser Trp Gly Gly Lys Glu Asn Gly
                165                 170                 175

Phe Gly Leu Ala Glu Cys Cys Arg Asp Leu His Met Met Lys Tyr Pro
            180                 185                 190

Pro Ser Ala Thr Thr Leu His Phe Glu Phe Tyr Ala Asp Pro Gly Ala
        195                 200                 205

Glu Val Lys Ile Glu Lys Arg Thr Thr Ser Asn Thr Leu His Tyr Ile
    210                 215                 220

His Ile Glu Gln Leu Asp Lys Ile Ser Glu Ser Pro Ser Glu Ile Met
225                 230                 235                 240

Glu Ser Leu Thr Lys Met Tyr Ser Ile Pro Lys Asp Lys Gln Met Leu
                245                 250                 255

Leu Phe Thr His Ile Arg Leu Ala His Gly Phe Ser Asn His Arg Lys
            260                 265                 270

Arg Leu Gln Ala Val Gln Ala Arg Leu His Ala Ile Ser Ile Leu Val
        275                 280                 285

Tyr Ser Asn Ala Leu Gln Glu Ser Ala Asn Ser Ile Leu Tyr Asn Gly
    290                 295                 300

Leu Ile Glu Glu Leu Val Asp Val Leu Gln Ile Thr Asp Lys Gln Leu
305                 310                 315                 320

Met Glu Ile Lys Ala Ala Ser Leu Arg Thr Leu Thr Ser Ile Val His
                325                 330                 335

Leu Glu Arg Thr Pro Lys Leu Ser Ser Ile Ile Asp Cys Thr Gly Thr
            340                 345                 350
```

-continued

```
Ala Ser Tyr His Gly Phe Leu Pro Val Leu Val Arg Asn Cys Ile Gln
            355                 360                 365

Ala Met Ile Asp Pro Ser Met Asp Pro Tyr Pro His Gln Phe Ala Thr
370                 375                 380

Ala Leu Phe Ser Phe Leu Tyr His Leu Ala Ser Tyr Asp Ala Gly Gly
385                 390                 395                 400

Glu Ala Leu Val Ser Cys Gly Met Met Glu Ala Leu Leu Lys Val Ile
                405                 410                 415

Lys Phe Leu Gly Asp Glu Gln Asp Gln Ile Thr Phe Val Thr Arg Ala
            420                 425                 430

Val Arg Val Asp Leu Ile Thr Asn Leu Asp Met Ala Ala Phe Gln
        435                 440                 445

Ser His Ser Gly Leu Ser Ile Phe Ile Tyr Arg Leu Glu His Glu Val
    450                 455                 460

Asp Leu Cys Arg Lys Glu Cys Pro Phe Val Ile Lys Pro Lys Ile Gln
465                 470                 475                 480

Arg Pro Asn Thr Thr Gln Glu Gly Glu Met Glu Thr Asp Met Asp
                485                 490                 495

Gly Val Gln Cys Ile Pro Gln Arg Ala Ala Leu Leu Lys Ser Met Leu
            500                 505                 510

Asn Phe Leu Lys Lys Ala Ile Gln Asp Pro Ala Phe Ser Asp Gly Ile
            515                 520                 525

Arg His Val Met Asp Gly Ser Leu Pro Thr Ser Leu Lys His Ile Ile
    530                 535                 540

Ser Asn Ala Glu Tyr Tyr Gly Pro Ser Leu Phe Leu Leu Ala Thr Glu
545                 550                 555                 560

Val Val Thr Val Phe Val Phe Gln Glu Pro Ser Leu Leu Ser Ser Leu
                565                 570                 575

Gln Asp Asn Gly Leu Thr Asp Val Met Leu His Ala Leu Leu Ile Lys
            580                 585                 590

Asp Val Pro Ala Thr Arg Glu Val Leu Gly Ser Leu Pro Asn Val Phe
        595                 600                 605

Ser Ala Leu Cys Leu Asn Ala Arg Gly Leu Gln Ser Phe Val Gln Cys
    610                 615                 620

Gln Pro Phe Glu Arg Leu Phe Lys Val Leu Leu Ser Pro Asp Tyr Leu
625                 630                 635                 640

Pro Ala Met Arg Arg Arg Ser Ser Asp Pro Leu Gly Asp Thr Ala
                645                 650                 655

Ser Asn Leu Gly Ser Ala Val Asp Glu Leu Met Arg His Gln Pro Thr
            660                 665                 670

Leu Lys Thr Asp Ala Thr Thr Ala Ile Ile Lys Leu Leu Glu Glu Ile
            675                 680                 685

Cys Asn Leu Gly Arg Asp Pro Lys Tyr Ile Cys Gln Lys Pro Ser Ile
    690                 695                 700

Gln Lys Ala Asp Gly Thr Ala Thr Ala Pro Pro Arg Ser Asn His
705                 710                 715                 720

Ala Ala Glu Glu Ala Ser Ser Glu Asp Glu Glu Glu Val Gln
                725                 730                 735

Ala Met Gln Ser Phe Asn Ser Thr Gln Gln Asn Glu Thr Glu Pro Asn
            740                 745                 750

Gln Gln Val Val Gly Thr Glu Glu Arg Ile Pro Ile Pro Leu Met Asp
        755                 760                 765

Tyr Ile Leu Asn Val Met Lys Phe Val Glu Ser Ile Leu Ser Asn Asn
```

```
                770             775             780
Thr Thr Asp Asp His Cys Gln Glu Phe Val Asn Gln Lys Gly Leu Leu
785             790             795             800

Pro Leu Val Thr Ile Leu Gly Leu Pro Asn Leu Pro Ile Asp Phe Pro
                805             810             815

Thr Ser Ala Ala Cys Gln Ala Val Ala Gly Val Cys Lys Ser Ile Leu
                820             825             830

Thr Leu Ser His Glu Pro Lys Val Leu Gln Glu Gly Leu Leu Gln Leu
                835             840             845

Asp Ser Ile Leu Ser Ser Leu Glu Pro Leu His Arg Pro Ile Glu Ser
850             855             860

Pro Gly Gly Ser Val Leu Leu Arg Glu Leu Ala Cys Ala Gly Asn Val
865             870             875             880

Ala Asp Ala Thr Leu Ser Ala Gln Ala Thr Pro Leu Leu His Ala Leu
                885             890             895

Thr Ala Ala His Ala Tyr Ile Met Met Phe Val His Thr Cys Arg Val
                900             905             910

Gly Gln Ser Glu Ile Arg Ser Ile Ser Val Asn Gln Trp Gly Ser Gln
                915             920             925

Leu Gly Leu Ser Val Leu Ser Lys Leu Ser Gln Leu Tyr Cys Ser Leu
930             935             940

Val Trp Glu Ser Thr Val Leu Leu Ser Leu Cys Thr Pro Asn Ser Leu
945             950             955             960

Pro Ser Gly Cys Glu Phe Gly Gln Ala Asp Met Gln Lys Leu Val Pro
                965             970             975

Lys Asp Glu Lys Ala Gly Thr Thr Gln Gly Gly Lys Arg Ser Asp Gly
                980             985             990

Glu Gln Asp Gly Ala Ala Gly Ser Met Asp Ala Ser Thr Gln Gly Leu
                995             1000            1005

Leu Glu Gly Ile Gly Leu Asp Gly Asp Thr Leu Ala Pro Met Glu
    1010            1015            1020

Thr Asp Glu Pro Thr Ala Ser Asp Ser Lys Gly Lys Ser Lys Ile
    1025            1030            1035

Thr Pro Ala Met Ala Ala Arg Ile Lys Gln Ile Lys Pro Leu Leu
    1040            1045            1050

Ser Ala Ser Ser Arg Leu Gly Arg Ala Leu Ala Glu Leu Phe Gly
    1055            1060            1065

Leu Leu Val Lys Leu Cys Val Gly Ser Pro Val Arg Gln Arg Arg
    1070            1075            1080

Ser His His Ala Ala Ser Thr Thr Thr Ala Pro Thr Pro Ala Ala
    1085            1090            1095

Arg Ser Thr Ala Ser Ala Leu Thr Lys Leu Leu Thr Lys Gly Leu
    1100            1105            1110

Ser Trp Gln Pro Pro Pro Tyr Thr Pro Thr Pro Arg Phe Arg Leu
    1115            1120            1125

Thr Phe Phe Ile Cys Ser Val Gly Phe Thr Ser Pro Met Leu Phe
    1130            1135            1140

Asp Glu Arg Lys Tyr Pro Tyr His Leu Met Leu Gln Lys Phe Leu
    1145            1150            1155

Cys Ser Gly Gly His Asn Ala Leu Phe Glu Thr Phe Asn Trp Ala
    1160            1165            1170

Leu Ser Met Gly Gly Lys Val Pro Val Ser Glu Gly Leu Glu His
    1175            1180            1185
```

-continued

Ser Asp Leu Pro Asp Gly Thr Gly Glu Phe Leu Asp Ala Trp Leu
    1190            1195                1200

Met Leu Val Glu Lys Met Val Asn Pro Thr Thr Val Leu Glu Ser
    1205            1210                1215

Pro His Ser Leu Pro Ala Lys Leu Pro Gly Gly Val Gln Asn Phe
    1220            1225                1230

Pro Gln Phe Ser Ala Leu Arg Phe Leu Val Val Thr Gln Lys Ala
    1235            1240                1245

Ala Phe Thr Cys Ile Lys Asn Leu Trp Asn Arg Lys Pro Leu Lys
    1250            1255                1260

Val Tyr Gly Gly Arg Met Ala Glu Ser Met Leu Ala Ile Leu Cys
    1265            1270                1275

His Ile Leu Arg Gly Glu Pro Val Ile Arg Glu Arg Leu Ser Lys
    1280            1285                1290

Glu Lys Glu Gly Ser Arg Gly Glu Glu Asp Thr Gly Gln Glu Glu
    1295            1300                1305

Gly Gly Ser Arg Arg Glu Pro Gln Val Asn Gln Gln Leu Gln
    1310            1315                1320

Gln Leu Met Asp Met Gly Phe Thr Arg Glu His Ala Met Glu Ala
    1325            1330                1335

Leu Leu Asn Thr Ser Thr Met Glu Gln Ala Thr Glu Tyr Leu Leu
    1340            1345                1350

Thr His Pro Pro Pro Ile Met Gly Gly Val Val Arg Asp Leu Ser
    1355            1360                1365

Met Ser Glu Glu Asp Gln Met Met Arg Ala Ile Ala Met Ser Leu
    1370            1375                1380

Gly Gln Asp Ile Pro Met Asp Gln Arg Ala Glu Ser Pro Glu Glu
    1385            1390                1395

Val Ala Cys Arg Lys Glu Glu Glu Arg Lys Ala Arg Glu Lys
    1400            1405                1410

Gln Glu Glu Glu Glu Ala Lys Cys Leu Glu Lys Phe Gln Asp Ala
    1415            1420                1425

Asp Pro Leu Glu Gln Asp Glu Leu His Thr Phe Thr Asp Thr Met
    1430            1435                1440

Leu Pro Gly Cys Phe His Leu Leu Asp Glu Leu Pro Asp Thr Val
    1445            1450                1455

Tyr Arg Val Cys Asp Leu Ile Met Thr Ala Ile Lys Arg Asn Gly
    1460            1465                1470

Ala Asp Tyr Arg Asp Met Ile Leu Lys Gln Val Val Asn Gln Val
    1475            1480                1485

Trp Glu Ala Ala Asp Val Leu Ile Lys Ala Ala Leu Pro Leu Thr
    1490            1495                1500

Thr Ser Asp Thr Lys Thr Val Ser Glu Trp Ile Ser Gln Met Ala
    1505            1510                1515

Thr Leu Pro Gln Ala Ser Asn Leu Ala Thr Arg Ile Leu Leu Leu
    1520            1525                1530

Thr Leu Leu Phe Glu Glu Leu Lys Leu Pro Cys Ala Trp Val Val
    1535            1540                1545

Glu Ser Ser Gly Ile Leu Asn Val Leu Ile Lys Leu Leu Glu Val
    1550            1555                1560

Val Gln Pro Cys Leu Gln Ala Ala Lys Glu Gln Lys Glu Val Gln
    1565            1570                1575

```
Thr Pro Lys Trp Ile Thr Pro Val Leu Leu Leu Ile Asp Phe Tyr
    1580            1585            1590

Glu Lys Thr Ala Ile Ser Ser Lys Arg Arg Ala Gln Met Thr Lys
    1595            1600            1605

Tyr Leu Gln Ser Asn Ser Asn Asn Trp Arg Trp Phe Asp Asp Arg
    1610            1615            1620

Ser Gly Arg Trp Cys Ser Tyr Ser Ala Ser Asn Asn Ser Thr Ile
    1625            1630            1635

Asp Ser Ala Trp Lys Ser Gly Glu Thr Ser Val Arg Phe Thr Ala
    1640            1645            1650

Gly Arg Arg Arg Tyr Thr Val Gln Phe Thr Thr Met Val Gln Val
    1655            1660            1665

Asn Glu Glu Thr Gly Asn Arg Arg Pro Val Met Leu Thr Leu Leu
    1670            1675            1680

Arg Val Pro Arg Leu Asn Lys Asn Ser Lys Asn Ser Asn Gly Gln
    1685            1690            1695

Glu Leu Glu Lys Thr Leu Glu Glu Ser Lys Glu Met Asp Ile Lys
    1700            1705            1710

Arg Lys Glu Asn Lys Gly Asn Asp Thr Pro Leu Ala Leu Glu Ser
    1715            1720            1725

Thr Asn Thr Glu Lys Glu Thr Ser Leu Glu Glu Thr Lys Ile Gly
    1730            1735            1740

Glu Ile Leu Ile Gln Gly Leu Thr Glu Asp Met Val Thr Val Leu
    1745            1750            1755

Ile Arg Ala Cys Val Ser Met Leu Gly Val Pro Val Asp Pro Asp
    1760            1765            1770

Thr Leu His Ala Thr Leu Arg Leu Cys Leu Arg Leu Thr Arg Asp
    1775            1780            1785

His Lys Tyr Ala Met Met Phe Ala Glu Leu Lys Ser Thr Arg Met
    1790            1795            1800

Ile Leu Asn Leu Thr Gln Ser Ser Gly Phe Asn Gly Phe Thr Pro
    1805            1810            1815

Leu Val Thr Leu Leu Leu Arg His Ile Ile Glu Asp Pro Cys Thr
    1820            1825            1830

Leu Arg His Thr Met Glu Lys Val Val Arg Ser Ala Ala Thr Ser
    1835            1840            1845

Gly Ala Gly Ser Thr Thr Ser Gly Val Val Ser Gly Ser Leu Gly
    1850            1855            1860

Ser Arg Glu Ile Asn Tyr Ile Leu Arg Val Leu Gly Pro Ala Ala
    1865            1870            1875

Cys Arg Asn Pro Asp Ile Phe Thr Glu Val Ala Asn Cys Cys Ile
    1880            1885            1890

Arg Ile Ala Leu Pro Ala Pro Arg Gly Ser Gly Thr Ala Ser Asp
    1895            1900            1905

Asp Glu Phe Glu Asn Leu Arg Ile Lys Gly Pro Asn Ala Val Gln
    1910            1915            1920

Leu Val Lys Thr Thr Pro Leu Lys Pro Ser Pro Leu Pro Val Ile
    1925            1930            1935

Pro Asp Thr Ile Lys Glu Val Ile Tyr Asp Met Leu Asn Ala Leu
    1940            1945            1950

Ala Ala Tyr His Ala Pro Glu Glu Ala Asp Lys Ser Asp Pro Lys
    1955            1960            1965

Pro Gly Val Met Thr Gln Glu Val Gly Gln Leu Leu Gln Asp Met
```

-continued

```
              1970                1975                1980

Gly  Asp  Asp  Val  Tyr  Gln  Gln  Tyr  Arg  Ser  Leu  Thr  Arg  Gln  Ser
              1985                1990                1995

Ser  Asp  Phe  Asp  Thr  Gln  Ser  Gly  Phe  Ser  Ile  Asn  Ser  Gln  Val
              2000                2005                2010

Phe  Ala  Ala  Asp  Gly  Ala  Ser  Thr  Glu  Thr  Ser  Ala  Ser  Gly  Thr
              2015                2020                2025

Ser  Gln  Gly  Glu  Ala  Ser  Thr  Pro  Glu  Glu  Ser  Arg  Asp  Gly  Lys
              2030                2035                2040

Lys  Asp  Lys  Glu  Gly  Asp  Arg  Ala  Ser  Glu  Glu  Gly  Lys  Gln  Lys
              2045                2050                2055

Gly  Lys  Gly  Ser  Lys  Pro  Leu  Met  Pro  Thr  Ser  Thr  Ile  Leu  Arg
              2060                2065                2070

Leu  Leu  Ala  Glu  Leu  Val  Arg  Ser  Tyr  Val  Gly  Ile  Ala  Thr  Leu
              2075                2080                2085

Ile  Ala  Asn  Tyr  Ser  Tyr  Thr  Val  Gly  Gln  Ser  Glu  Leu  Ile  Lys
              2090                2095                2100

Glu  Asp  Cys  Ser  Val  Leu  Ala  Phe  Val  Leu  Asp  His  Leu  Leu  Pro
              2105                2110                2115

His  Thr  Gln  Asn  Ala  Glu  Asp  Lys  Asp  Thr  Pro  Ala  Leu  Ala  Arg
              2120                2125                2130

Leu  Phe  Leu  Ala  Ser  Leu  Ala  Ala  Ala  Gly  Ser  Gly  Thr  Asp  Ala
              2135                2140                2145

Gln  Val  Ala  Leu  Val  Asn  Glu  Val  Lys  Ala  Ala  Leu  Gly  Arg  Ala
              2150                2155                2160

Leu  Ala  Met  Ala  Glu  Ser  Thr  Glu  Lys  His  Ala  Arg  Leu  Gln  Ala
              2165                2170                2175

Val  Met  Cys  Ile  Ile  Ser  Thr  Ile  Met  Glu  Ser  Cys  Pro  Ser  Thr
              2180                2185                2190

Ser  Ser  Phe  Tyr  Ser  Ser  Ala  Thr  Ala  Lys  Thr  Gln  His  Asn  Gly
              2195                2200                2205

Met  Asn  Asn  Ile  Ile  Arg  Leu  Phe  Leu  Lys  Lys  Gly  Leu  Val  Asn
              2210                2215                2220

Asp  Leu  Ala  Arg  Val  Pro  His  Ser  Leu  Asp  Leu  Ser  Ser  Pro  Asn
              2225                2230                2235

Met  Ala  Asn  Thr  Val  Asn  Ala  Ala  Leu  Lys  Pro  Leu  Glu  Thr  Leu
              2240                2245                2250

Ser  Arg  Ile  Val  Asn  Gln  Pro  Ser  Ser  Leu  Phe  Gly  Ser  Lys  Ser
              2255                2260                2265

Ala  Ser  Ser  Lys  Asn  Lys  Ser  Glu  Gln  Asp  Ala  Gln  Gly  Ala  Ser
              2270                2275                2280

Gln  Asp  Ser  Ser  Ser  Asn  Gln  Gln  Asp  Pro  Gly  Glu  Pro  Gly  Glu
              2285                2290                2295

Ala  Glu  Val  Gln  Glu  Glu  Asp  His  Asp  Val  Thr  Gln  Thr  Glu  Val
              2300                2305                2310

Ala  Asp  Gly  Asp  Ile  Met  Asp  Gly  Glu  Ala  Glu  Thr  Asp  Ser  Val
              2315                2320                2325

Val  Ile  Ala  Gly  Gln  Pro  Glu  Val  Leu  Ser  Ser  Gln  Glu  Met  Gln
              2330                2335                2340

Val  Glu  Asn  Glu  Leu  Glu  Asp  Leu  Ile  Asp  Glu  Leu  Leu  Glu  Arg
              2345                2350                2355

Asp  Gly  Gly  Ser  Gly  Asn  Ser  Thr  Ile  Ile  Val  Ser  Arg  Ser  Gly
              2360                2365                2370
```

-continued

```
Glu Asp Glu Ser Gln Glu Asp Val Leu Met Asp Glu Ala Pro Ser
    2375            2380                2385
Asn Leu Ser Gln Ala Ser Thr Leu Gln Ala Asn Arg Glu Asp Ser
    2390            2395                2400
Met Asn Ile Leu Asp Pro Glu Asp Glu Glu His Thr Gln Glu
    2405            2410                2415
Glu Asp Ser Ser Gly Ser Asn Glu Asp Glu Asp Ser Gln Asp
    2420            2425                2430
Glu Glu Glu Glu Glu Glu Asp Glu Asp Gln Glu Asp
    2435            2440                2445
Asp Glu Gly Glu Glu Gly Glu Asp Asp Asp Asp Gly Ser
    2450            2455                2460
Glu Met Glu Leu Asp Glu Asp Tyr Pro Asp Met Asn Ala Ser Pro
    2465            2470                2475
Leu Val Arg Phe Glu Arg Phe Asp Arg Glu Asp Asp Leu Ile Ile
    2480            2485                2490
Glu Phe Asp Asn Met Phe Ser Ser Ala Thr Asp Ile Pro Pro Ser
    2495            2500                2505
Pro Gly Asn Ile Pro Thr Thr His Pro Leu Met Val Arg His Ala
    2510            2515                2520
Asp His Ser Ser Leu Thr Leu Gly Ser Gly Ser Ser Thr Thr Arg
    2525            2530                2535
Leu Thr Gln Gly Ile Gly Arg Ser Gln Arg Thr Leu Arg Gln Leu
    2540            2545                2550
Thr Ala Asn Thr Gly His Thr Ile His Val His Tyr Pro Gly Asn
    2555            2560                2565
Arg Gln Pro Asn Pro Pro Leu Ile Leu Gln Arg Leu Leu Gly Pro
    2570            2575                2580
Ser Ala Ala Ala Asp Ile Leu Gln Leu Ser Ser Ser Leu Pro Leu
    2585            2590                2595
Gln Ser Arg Gly Arg Ala Arg Leu Leu Val Gly Asn Asp Asp Val
    2600            2605                2610
His Ile Ile Ala Arg Ser Asp Asp Glu Leu Leu Asp Asp Phe Phe
    2615            2620                2625
His Asp Gln Ser Thr Ala Thr Ser Gln Ala Gly Thr Leu Ser Ser
    2630            2635                2640
Ile Pro Thr Ala Leu Thr Arg Trp Thr Glu Glu Cys Lys Val Leu
    2645            2650                2655
Asp Ala Glu Ser Met His Asp Cys Val Ser Val Val Lys Val Ser
    2660            2665                2670
Ile Val Asn His Leu Glu Phe Leu Arg Asp Glu Glu Leu Glu Glu
    2675            2680                2685
Arg Arg Glu Lys Arg Arg Lys Gln Leu Ala Glu Glu Glu Thr Lys
    2690            2695                2700
Ile Thr Asp Lys Gly Lys Glu Asp Lys Glu Asn Arg Asp Gln Ser
    2705            2710                2715
Ala Gln Cys Thr Ala Ser Lys Ser Asn Asp Ser Thr Glu Gln Asn
    2720            2725                2730
Leu Ser Asp Gly Thr Pro Met Pro Asp Ser Tyr Pro Thr Thr Pro
    2735            2740                2745
Ser Ser Thr Asp Ala Ala Thr Ser Glu Ser Lys Glu Thr Leu Gly
    2750            2755                2760
```

```
Thr Leu Gln Ser Ser Gln Gln Pro Thr Leu Pro Thr Pro Pro
2765                2770            2775

Ala Leu Gly Glu Val Pro Gln Glu Leu Gln Ser Pro Ala Gly Glu
    2780                2785            2790

Gly Gly Ser Ser Thr Gln Leu Leu Met Pro Val Glu Pro Glu Glu
    2795                2800            2805

Leu Gly Pro Thr Arg Pro Ser Gly Glu Ala Glu Thr Thr Gln Met
    2810                2815            2820

Glu Leu Ser Pro Ala Pro Thr Ile Thr Ser Leu Ser Pro Glu Arg
    2825                2830            2835

Ala Glu Asp Ser Asp Ala Leu Thr Ala Val Ser Ser Gln Leu Glu
    2840                2845            2850

Gly Ser Pro Met Asp Thr Ser Ser Leu Ala Ser Cys Thr Leu Glu
    2855                2860            2865

Glu Ala Val Gly Asp Thr Ser Ala Ala Gly Ser Ser Glu Gln Pro
    2870                2875            2880

Arg Ala Gly Ser Ser Thr Pro Gly Asp Ala Pro Pro Ala Val Ala
    2885                2890            2895

Glu Val Gln Gly Arg Ser Asp Gly Ser Gly Glu Ser Ala Gln Pro
    2900                2905            2910

Pro Glu Asp Ser Ser Pro Pro Ala Ser Ser Glu Ser Ser Ser Thr
    2915                2920            2925

Arg Asp Ser Ala Val Ala Ile Ser Gly Ala Asp Ser Arg Gly Ile
    2930                2935            2940

Leu Glu Glu Pro Leu Pro Ser Thr Ser Ser Glu Glu Glu Asp Pro
    2945                2950            2955

Leu Ala Gly Ile Ser Leu Pro Glu Gly Val Asp Pro Ser Phe Leu
    2960                2965            2970

Ala Ala Leu Pro Asp Asp Ile Arg Arg Glu Val Leu Gln Asn Gln
    2975                2980            2985

Leu Gly Ile Arg Pro Pro Thr Arg Thr Ala Pro Ser Thr Asn Ser
    2990                2995            3000

Ser Ala Pro Ala Val Val Gly Asn Pro Gly Val Thr Glu Val Ser
    3005                3010            3015

Pro Glu Phe Leu Ala Ala Leu Pro Pro Ala Ile Gln Glu Glu Val
    3020                3025            3030

Leu Ala Gln Gln Arg Ala Glu Gln Gln Arg Arg Glu Leu Ala Gln
    3035                3040            3045

Asn Ala Ser Ser Asp Thr Pro Met Asp Pro Val Thr Phe Ile Gln
    3050                3055            3060

Thr Leu Pro Ser Asp Leu Arg Arg Ser Val Leu Glu Asp Met Glu
    3065                3070            3075

Asp Ser Val Leu Ala Val Met Pro Pro Asp Ile Ala Ala Glu Ala
    3080                3085            3090

Gln Ala Leu Arg Arg Glu Gln Glu Ala Arg Gln Arg Gln Leu Met
    3095                3100            3105

His Glu Arg Leu Phe Gly His Ser Ser Thr Ser Ala Leu Ser Ala
    3110                3115            3120

Ile Leu Arg Ser Pro Ala Phe Thr Ser Arg Leu Ser Gly Asn Arg
    3125                3130            3135

Gly Val Gln Tyr Thr Arg Leu Ala Val Gln Arg Gly Gly Thr Phe
    3140                3145            3150

Gln Met Gly Gly Ser Ser Ser His Asn Arg Pro Ser Gly Ser Asn
```

```
            3155                3160                3165

Val Asp Thr Leu Leu Arg Leu Arg Gly Arg Leu Leu Asp His
    3170                3175                3180

Glu Ala Leu Ser Cys Leu Leu Val Leu Leu Phe Val Asp Glu Pro
    3185                3190                3195

Lys Leu Asn Thr Ser Arg Leu His Arg Val Leu Arg Asn Leu Cys
    3200                3205                3210

Tyr His Ala Gln Thr Arg His Trp Val Ile Arg Ser Leu Leu Ser
    3215                3220                3225

Ile Leu Gln Arg Ser Ser Glu Ser Glu Leu Cys Ile Glu Thr Pro
    3230                3235                3240

Lys Leu Thr Thr Ser Glu Glu Lys Gly Lys Lys Ser Ser Lys Ser
    3245                3250                3255

Cys Gly Ser Ser Ser His Glu Asn Arg Pro Leu Asp Leu Leu His
    3260                3265                3270

Lys Met Glu Ser Lys Ser Ser Asn Gln Leu Ser Trp Leu Ser Val
    3275                3280                3285

Ser Met Asp Ala Ala Leu Gly Cys Arg Thr Asn Ile Phe Gln Ile
    3290                3295                3300

Gln Arg Ser Gly Gly Arg Lys His Thr Glu Lys His Ala Ser Gly
    3305                3310                3315

Gly Ser Thr Val His Ile His Pro Gln Ala Ala Pro Val Val Cys
    3320                3325                3330

Arg His Val Leu Asp Thr Leu Ile Gln Leu Ala Lys Val Phe Pro
    3335                3340                3345

Ser His Phe Thr Gln Gln Arg Thr Lys Glu Thr Asn Cys Glu Ser
    3350                3355                3360

Asp Arg Glu Arg Gly Asn Lys Ala Cys Ser Pro Cys Ser Ser Gln
    3365                3370                3375

Ser Ser Ser Ser Gly Ile Cys Thr Asp Phe Trp Asp Leu Leu Val
    3380                3385                3390

Lys Leu Asp Asn Met Asn Val Ser Arg Lys Gly Lys Asn Ser Val
    3395                3400                3405

Lys Ser Val Pro Val Ser Ala Gly Gly Glu Gly Glu Thr Ser Pro
    3410                3415                3420

Tyr Ser Leu Glu Ala Ser Pro Leu Gly Gln Leu Met Asn Met Leu
    3425                3430                3435

Ser His Pro Val Ile Arg Arg Ser Ser Leu Leu Thr Glu Lys Leu
    3440                3445                3450

Leu Arg Leu Leu Ser Leu Ile Ser Ile Ala Leu Pro Glu Asn Lys
    3455                3460                3465

Val Ser Glu Ala Gln Ala Asn Ser Gly Ser Gly Ala Ser Ser Thr
    3470                3475                3480

Thr Thr Ala Thr Ser Thr Thr Ser Thr Thr Thr Thr Ala Ala
    3485                3490                3495

Ser Thr Thr Pro Thr Pro Pro Thr Ala Pro Thr Pro Val Thr Ser
    3500                3505                3510

Ala Pro Ala Leu Val Ala Ala Thr Ala Ile Ser Thr Ile Val Val
    3515                3520                3525

Ala Ala Ser Thr Thr Val Thr Thr Pro Thr Thr Ala Thr Thr Thr
    3530                3535                3540

Val Ser Ile Ser Pro Thr Thr Lys Gly Ser Lys Ser Pro Ala Lys
    3545                3550                3555
```

```
Val Ser Asp Gly Gly Ser Ser Thr Asp Phe Lys Met Val Ser
    3560            3565                3570

Ser Gly Leu Thr Glu Asn Gln Leu Gln Leu Ser Val Glu Val Leu
    3575            3580                3585

Thr Ser His Ser Cys Ser Glu Glu Gly Leu Glu Asp Ala Ala Asn
    3590            3595                3600

Val Leu Leu Gln Leu Ser Arg Gly Asp Ser Gly Thr Arg Asp Thr
    3605            3610                3615

Val Leu Lys Leu Leu Leu Asn Gly Ala Arg His Leu Gly Tyr Thr
    3620            3625                3630

Leu Cys Lys Gln Ile Gly Thr Leu Leu Ala Glu Leu Arg Glu Tyr
    3635            3640                3645

Asn Leu Glu Gln Gln Arg Arg Ala Gln Cys Glu Thr Leu Ser Pro
    3650            3655                3660

Asp Gly Leu Pro Glu Glu Gln Pro Gln Thr Thr Lys Leu Lys Gly
    3665            3670                3675

Lys Met Gln Ser Arg Phe Asp Met Ala Glu Asn Val Val Ile Val
    3680            3685                3690

Ala Ser Gln Lys Arg Pro Leu Gly Gly Arg Glu Leu Gln Leu Pro
    3695            3700                3705

Ser Met Ser Met Leu Thr Ser Lys Thr Ser Thr Gln Lys Phe Phe
    3710            3715                3720

Leu Arg Val Leu Gln Val Ile Ile Gln Leu Arg Asp Asp Thr Arg
    3725            3730                3735

Arg Ala Asn Lys Lys Ala Lys Gln Thr Gly Arg Leu Gly Ser Ser
    3740            3745                3750

Gly Leu Gly Ser Ala Ser Ser Ile Gln Ala Ala Val Arg Gln Leu
    3755            3760                3765

Glu Ala Glu Ala Asp Ala Ile Ile Gln Met Val Arg Glu Gly Gln
    3770            3775                3780

Arg Ala Arg Arg Gln Gln Gln Ala Ala Thr Ser Glu Ser Ser Gln
    3785            3790                3795

Ser Glu Ala Ser Val Arg Arg Glu Glu Ser Pro Met Asp Val Asp
    3800            3805                3810

Gln Pro Ser Pro Ser Ala Gln Asp Thr Gln Ser Ile Ala Ser Asp
    3815            3820                3825

Gly Thr Pro Gln Gly Glu Lys Glu Lys Glu Glu Arg Pro Pro Glu
    3830            3835                3840

Leu Pro Leu Leu Ser Glu Gln Leu Ser Leu Asp Glu Leu Trp Asp
    3845            3850                3855

Met Leu Gly Glu Cys Leu Lys Glu Leu Glu Glu Ser His Asp Gln
    3860            3865                3870

His Ala Val Leu Val Leu Gln Pro Ala Val Glu Ala Phe Phe Leu
    3875            3880                3885

Val His Ala Thr Glu Arg Glu Ser Lys Pro Pro Val Arg Asp Thr
    3890            3895                3900

Arg Glu Ser Gln Leu Ala His Ile Lys Asp Glu Pro Pro Pro Leu
    3905            3910                3915

Ser Pro Ala Pro Leu Thr Pro Ala Thr Pro Ser Ser Leu Asp Pro
    3920            3925                3930

Phe Phe Ser Arg Glu Pro Ser Ser Met His Ile Ser Ser Ser Leu
    3935            3940                3945
```

-continued

Pro Pro Asp Thr Gln Lys Phe Leu Arg Phe Ala Glu Thr His Arg
        3950            3955            3960

Thr Val Leu Asn Gln Ile Leu Arg Gln Ser Thr Thr His Leu Ala
        3965            3970            3975

Asp Gly Pro Phe Ala Val Leu Val Asp Tyr Ile Arg Val Leu Asp
        3980            3985            3990

Phe Asp Val Lys Arg Lys Tyr Phe Arg Gln Glu Leu Glu Arg Leu
        3995            4000            4005

Asp Glu Gly Leu Arg Lys Glu Asp Met Ala Val His Val Arg Arg
        4010            4015            4020

Asp His Val Phe Glu Asp Ser Tyr Arg Glu Leu His Arg Lys Ser
        4025            4030            4035

Pro Glu Glu Met Lys Asn Arg Leu Tyr Ile Val Phe Glu Gly Glu
        4040            4045            4050

Glu Gly Gln Asp Ala Gly Gly Leu Leu Arg Glu Trp Tyr Met Ile
        4055            4060            4065

Ile Ser Arg Glu Met Phe Asn Pro Met Tyr Ala Leu Phe Arg Thr
        4070            4075            4080

Ser Pro Gly Asp Arg Val Thr Tyr Thr Ile Asn Pro Ser Ser His
        4085            4090            4095

Cys Asn Pro Asn His Leu Ser Tyr Phe Lys Phe Val Gly Arg Ile
        4100            4105            4110

Val Ala Lys Ala Val Tyr Asp Asn Arg Leu Leu Glu Cys Tyr Phe
        4115            4120            4125

Thr Arg Ser Phe Tyr Lys His Ile Leu Gly Lys Ser Val Arg Tyr
        4130            4135            4140

Thr Asp Met Glu Ser Glu Asp Tyr His Phe Tyr Gln Gly Leu Val
        4145            4150            4155

Tyr Leu Leu Glu Asn Asp Val Ser Thr Leu Gly Tyr Asp Leu Thr
        4160            4165            4170

Phe Ser Thr Glu Val Gln Glu Phe Gly Val Cys Glu Val Arg Asp
        4175            4180            4185

Leu Lys Pro Asn Gly Ala Asn Ile Leu Val Thr Glu Glu Asn Lys
        4190            4195            4200

Lys Glu Tyr Val His Leu Val Cys Gln Met Arg Met Thr Gly Ala
        4205            4210            4215

Ile Arg Lys Gln Leu Ala Ala Phe Leu Glu Gly Phe Tyr Glu Ile
        4220            4225            4230

Ile Pro Lys Arg Leu Ile Ser Ile Phe Thr Glu Gln Glu Leu Glu
        4235            4240            4245

Leu Leu Ile Ser Gly Leu Pro Thr Ile Asp Ile Asp Asp Leu Lys
        4250            4255            4260

Ser Asn Thr Glu Tyr His Lys Tyr Gln Ser Asn Ser Ile Gln Ile
        4265            4270            4275

Gln Trp Phe Trp Arg Ala Leu Arg Ser Phe Asp Gln Ala Asp Arg
        4280            4285            4290

Ala Lys Phe Leu Gln Phe Val Thr Gly Thr Ser Lys Val Pro Leu
        4295            4300            4305

Gln Gly Phe Ala Ala Leu Glu Gly Met Asn Gly Ile Gln Lys Phe
        4310            4315            4320

Gln Ile His Arg Asp Asp Arg Ser Thr Asp Arg Leu Pro Ser Ala
        4325            4330            4335

His Thr Cys Phe Asn Gln Leu Asp Leu Pro Ala Tyr Glu Ser Phe

```
                4340            4345            4350
     Glu Lys Leu Arg His Met Leu Leu Leu Ala Ile Gln Glu Cys Ser
         4355            4360            4365
     Glu Gly Phe Gly Leu Ala
         4370
```

<210> SEQ ID NO 16
<211> LENGTH: 195
<212> TYPE: PRT
<213> ORGANISM: Homo sapiens

<400> SEQUENCE: 16

```
Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190

Gly Met Asp
        195
```

<210> SEQ ID NO 17
<211> LENGTH: 198
<212> TYPE: PRT
<213> ORGANISM: Homo sapiens

<400> SEQUENCE: 17

```
Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
```

|  |  |  |  | 85 |  |  |  | 90 |  |  |  | 95 |  |
| --- | --- | --- | --- | --- | --- | --- | --- | --- | --- | --- | --- | --- | --- |
| Phe | Ser | Phe | Asp | Thr | Asp | Arg | Ser | Pro | Ala | Pro | Met | Ser | Cys | Asp | Lys |

Phe Ser Phe Asp Thr Asp Arg Ser Pro Ala Pro Met Ser Cys Asp Lys
                        100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
                180                 185                 190

Leu Val Trp Arg Met His
            195

<210> SEQ ID NO 18
<211> LENGTH: 8460
<212> TYPE: DNA
<213> ORGANISM: Homo sapiens

<400> SEQUENCE: 18

```
gctggggcca agccgcagag cggagttggc atttccagat tggggctcgg gccgcgcctc      60
ctccgggacc ctcccttgg accgagccga tcgccgcggg gcagttcggg ccggctgtcc      120
tggcgcgaaa aggtggacaa gtcctatttt caagagaaga tgactttaa cagttttgaa      180
ggatctaaaa cttgtgtacc tgcagacatc aataaggaag aagaatttgt agaagagttt      240
aatagattaa aaacttttgc taattttcca agtggtagtc ctgtttcagc atcaacactg      300
gcacgagcag ggtttcttta tactggtgaa ggagataccg tgcggtgctt tagttgtcat      360
gcagctgtag atagatggca atatggagac tcagcagttg aagacacag gaaagtatcc      420
ccaaattgca gatttatcaa cggcttttat cttgaaaata gtgccacgca gtctacaaat      480
tctggtatcc agaatggtca gtacaaagtt gaaaactatc tgggaagcag agatcatttt      540
gccttagaca ggccatctga cacacatgca gactatcttt tgagaactgg gcaggttgta      600
gatatatcag acaccatata cccgaggaac cctgccatgt atagtgaaga agctagatta      660
aagtcctttc agaactggcc agactatgct cacctaaccc caagagagtt agcaagtgct      720
ggactctact acacaggtat tggtgaccaa gtgcagtgct tttgttgtgg tggaaaactg      780
aaaaattggg aaccttgtga tcgtgcctgg tcagaacaca gcgacactt cctaattgc      840
ttctttgttt tgggccggaa tcttaatatt cgaagtgaat ctgatgctgt gagttctgat      900
aggaatttcc caaattcaac aaatcttcca agaaatccat ccatggcaga ttatgaagca      960
cggatcttta cttttgggac atggatatac tcagttaaca aggagcagct tgcaagagct      1020
ggattttatg cttaggtga aggtgataaa gtaaagtgct tcactgtgg aggagggcta      1080
actgattgga agcccagtga agacccttgg gaacaacatg ctaaatggta tccagggtgc      1140
aaatatctgt tagaacagaa gggacaagaa tatataaaca atattcattt aactcattca      1200
cttgaggagt gtctggtaag aactactgag aaaacaccat cactaactag aagaattgat      1260
gataccatct tccaaaatcc tatggtacaa gaagctatac gaatggggtt cagtttcaag      1320
gacattaaga aaataatgga ggaaaaaatt cagatatctg ggagcaacta taatcactt      1380
gaggttctgg ttgcagatct agtgaatgct cagaaagaca gtatgcaaga tgagtcaagt      1440
```

| | |
|---|---|
| cagacttcat tacagaaaga gattagtact gaagagcagc taaggcgcct gcaagaggag | 1500 |
| aagctttgca aaatctgtat ggatagaaat attgctatcg tttttgttcc ttgtggacat | 1560 |
| ctagtcactt gtaaacaatg tgctgaagca gttgacaagt gtcccatgtg ctacacagtc | 1620 |
| attactttca agcaaaaaat ttttatgtct taatctaact ctatagtagg catgttatgt | 1680 |
| tgttcttatt accctgattg aatgtgtgat gtgaactgac tttaagtaat caggattgaa | 1740 |
| ttccattagc atttgctacc aagtaggaaa aaaatgtac atggcagtgt tttagttggc | 1800 |
| aatataatct ttgaatttct tgattttca gggtattagc tgtattatcc atttttttta | 1860 |
| ctgttattta attgaaacca tagactaaga ataagaagca tcatactata actgaacaca | 1920 |
| atgtgtattc atagtatact gatttaattt ctaagtgtaa gtgaattaat catctggatt | 1980 |
| ttttattctt ttcagatagg cttaacaaat ggagctttct gtatataaat gtggagatta | 2040 |
| gagttaatct ccccaatcac ataatttgtt ttgtgtgaaa aaggaataaa ttgttccatg | 2100 |
| ctggtggaaa gatagagatt gttttagag gttggttgtt gtgttttagg attctgtcca | 2160 |
| ttttctttta aagttataaa cacgtacttg tgcgaattat ttttttaaag tgatttgcca | 2220 |
| tttttgaaag cgtatttaat gatagaatac tatcgagcca acatgtactg acatggaaag | 2280 |
| atgtcaaaga tatgttaagt gtaaaatgca agtggcaaaa cactatgtat agtctgagcc | 2340 |
| agatcaaagt atgtatgttt taatatgca tagaacaaaa gatttggaaa gatatacacc | 2400 |
| aaactgttaa atgtggtttc tcttcgggga gggggggatt gggggagggg ccccagaggg | 2460 |
| gttttatagg ggccttttca ctttctactt ttttcatttt gttctgttcg aatttttat | 2520 |
| aagtatgtat tactttttgta atcagaattt ttagaaagta ttttgctgat ttaaaggctt | 2580 |
| aggcatgttc aaacgcctgc aaaactactt atcactcagc tttagttttt ctaatccaag | 2640 |
| aaggcagggc agttaacctt tttggtgcca atgtgaaatg taaatgattt tatgtttttc | 2700 |
| ctgctttgtg gatgaaaaat atttctgagt ggtagttttt tgacaggtag accatgtctt | 2760 |
| atcttgtttc aaaataagta tttctgattt tgtaaaatga aatataaaat atgtctcaga | 2820 |
| tcttccaatt aattagtaag gattcatcct taatccttgc tagtttaagc ctgcctaagt | 2880 |
| cactttacta aaagatcttt gttaactcag tattttaaac atctgtcagc ttatgtaggt | 2940 |
| aaaagtagaa gcatgtttgt acactgcttg tagttatagt gacagctttc catgttgaga | 3000 |
| ttctcatatc atcttgtatc ttaaagtttc atgtgagttt ttaccgttag gatgattaag | 3060 |
| atgtatatag gacaaaatgt taagtctttc ctctacctac atttgttttc ttggctagta | 3120 |
| atagtagtag atacttctga aataaatgtt ctctcaagat ccttaaaacc tcttggaaat | 3180 |
| tataaaaata ttggcaagaa aagaagaata gttgtttaaa tatttttaa aaaacacttg | 3240 |
| aataagaatc gtagggtat aaactagaag tttaaaatg cttcatagaa cgtccagggt | 3300 |
| ttacattaca agattctcac aacaaaccta tgtagaggt gagtaaggca tgttactaca | 3360 |
| gaggaaagtt tgagagtaaa actgtaaaaa attatatttt tgttgtactt tctaagagaa | 3420 |
| agagtattgt tatgttctcc taacttctgt tgattactac tttaagtgat attcatttaa | 3480 |
| aacattgcaa atttatttta ttatttaat tttctttttg agatggagtc ttgcttgtca | 3540 |
| cccaggctgg agtgcagtgg agtgatctct gctcactgca acctccgcct tctgggttca | 3600 |
| agcgattctc gtgcctcagc ttcctgagta gctggaatta caggcaggtg ccaccatgcc | 3660 |
| cgactaattt tttttatt ttagtagaga cggggtttca ccatgttggc caggctggta | 3720 |
| tcaaactcct gacctcaaga gatccactcg ccttgccctc ccaaagtgct gggattacag | 3780 |
| gcttgagcca ccacgcccgg ctaaaacatt gcaaatttaa atgagagttt taaaaattaa | 3840 |

```
ataatgactg ccctgtttct gttttagtat gtaaatcctc agttcttcac ctttgcactg    3900
tctgccactt agtttggtta tatagtcatt aacttgaatt tggtctgtat agtctagact    3960
ttaaatttaa agttttctac aaggggagaa aagtgttaaa attttaaaa tatgttttcc     4020 aggacacttc acttccaagt caggtaggta gttcaatcta gttgttagcc aaggactcaa    4080
ggactgaatt gttttaacat aaggcttttc ctgttctggg agccgcactt cattaaaatt    4140
cttctaaaac ttgtatgttt agagttaagc aagactttt tcttcctct ccatgagttg      4200 tgaaatttaa tgcacaacgc tgatgtggct aacaagttta ttttaagaat tgtttagaaa    4260
tgctgttgct tcaggttctt aaaatcactc agcactccaa cttctaatca aattttggga    4320
gacttaacag catttgtctg tgtttgaact ataaaaagca ccggatcttt tccatctaat    4380
tccgcaaaaa ttgatcattt gcaaagtcaa aactatagcc atatccaaat cttttccccc    4440
tcccaagagt tctcagtgtc tacatgtaga ctattccttt tctgtataaa gttcactcta    4500
ggatttcaag tcaccactta ttttacattt tagtcatgca aagattcaag tagttttgca    4560
ataagtactt atctttattt gtaataattt agtctgctga tcaaaagcat tgtcttaatt    4620
tttgagaact ggttttagca tttacaaact aaattccagt taattaatta atagctttat    4680
attgcctttc ctgctacatt tggttttttc ccctgtccct ttgattacgg gctaaggtag    4740
ggtagagtgg gtgtagtgag tgtatataat gtgatttggc cctgtgtatt atgatatttt    4800 gttattttg ttgttatatt atttacattt cagtagttgt tttttgtgtt tccattttag     4860
tggataaaat ttgtattttg aactatgaat ggagactacc gccccagcat tagtttcaca    4920
tgatataccc tttaaacccg aatcattgtt ttatttcctg attacacagg tgttgaatgg    4980
ggaaaggggc tagtatatca gtaggatata ctatgggatg tatatatc attgctgtta     5040 gagaaatgaa ataaatggg gctgggctca gtggctcacg cctgtaatcc cagcactttg    5100
ggaggctgag gcaggtggat cacgaggtca ggagatcgag accatcctgg ctaacacggt    5160
gaaaccccgt ctctactaaa aacagaaaaa ttagccgggc gtggtggcgg gcgcctgtag    5220
tcccagctac tcgggaggct gaggcaggag aatggtgtga acccgggagg cagagcttgc    5280
agtgagccga gatctcgcca ctgcactcca gcctgggcaa cagagcaaga ctctgtctca    5340
aaaaaaaaaa aaaagaaat aagaaatgg gaagcaatat ttgacatagt tctttttagt     5400
caaatctact tgttaaaaaa agggtagcag tttattcatc tgtgaaagga aataatact     5460 tatcttacaa ggttgcaaga gctcaaggag accatgtatg taaagttcct gctgtaaata    5520
tgaactccca tcctaatacc cttttacctc tctgtgggtt tgtcttgacc tggaaatttg    5580
ggctaaaact tagaaaaat tcttacatga taactcagtg atgcttactc atagttttg      5640 gtgtttctca tagataagat ataaatcagc tgggcgcggt ggctcatgcc tgtaatccca    5700
gcactttggg aggccgaggc gggcagatca cctgaggtcg ggaggtcgag accagcctga    5760
ccaacatgga gaaccccgt ctctactaaa aatacaaaat tagctgggcg tggtggctca     5820
tgcctgtaat cccagctact gggaggctg aggcaggaga tcgcttgaa cccaggaggc      5880 ggaggttgtg gtgagcgaag atcgtgccat tgcactccag cctgggcaac aagagcaaaa    5940
ctctgtctca aaaaaaaaa aagatataaa tcacaataaa taaataggtc aatacaaatg     6000
ttagccaggc gtggtggcac atgcccatag tcgcagctac tctggaggca gaggcaggag    6060
gatcacttga gccatgaat ttgaggcagc agtgagctat gattgtgcca ctgtactcca     6120
gtctgggtga cagagtgaga ccccatctct aaataaatag gtcaaaccct taaaatatt     6180
```

```
taaattctta aaaaattgaa aagattattc ttctcaaatt tagttgagct ttctaagaga    6240
agcaattggc ttttccccac ttcaataatc attttcagtt tgactcatac agttaacaca    6300
atgtgaattt cttcctcagc ataacagagt tatagaatga cagggctgga agtgacctta    6360
gagagtatcc agttctttca ttttacaggt gaggcaactg agactcaaag gtgatgtaat    6420
ttgtgcaaag attatagcta attagtagca gagccctgac tgggacatag tttgaaggtg    6480
aaaaacttca ccaagctacc tttcttgaaa ggtccaaatg tttatgtttt caactactct    6540
ttccactgta ccataacttt cactacatat taaatgacac tttataacta atataatagg    6600
acaatcatca atgcatatat agccagccct tcatatctgt gggttttgca tccatggatt    6660
caaccaagga ggaattgaaa acactgagaa aaaaaaaaaa gaccacacaa taaaaaaaaa    6720
aaatacaaaa taatacaaag aaaaagccaa aattgtcata ctgttgttaa gcaacagtat    6780
aacaactatt tacatagcat taaggttggt gcaaaaatgc aaaaaaaaaa aaagcaatta    6840
tttttaaacc aacctaatat attgtattag gtattaaagt catctggaca tgaattaaag    6900
tatatgatgc cagcctggac aaaaggcaaa accctgtctc tacaaaaaat acaaaaatta    6960
gctgggcatg gtggtgtgtg cctgtagtcc tggctactcc ggagcctgag gtgggaggat    7020
cgcttgagtc tgggaggcag aggctgcatt gagctatgat catggcactg cattccagcc    7080
tgggtgacag tgcaagacct tgtctcagaa taaataaagt atgtgatgaa gatgtgcata    7140
cattatatgc aaatactgtt ttttttttt taatttaaa cagtctcact gtgttgccca    7200
ggatggagtg caatggcaca atcttggctc atggcaaact ctgcctcgca agcagctggg    7260
actacaggca tgctccacgg tgcccagtta atttttttg tattcttagt agagacaggg    7320
tttcaccatg ttggccaggc tagtcttgaa tttctgacct caagtgattc atctcccaaa    7380
gtgctgggat tacaggcgtg agccaccacg gccggctaat ttttgtattt tttagtagtg    7440
actggtttcg cggtgttgac caggctggtc tcgaactcct gatctcaggt gatctgcctg    7500
cctcggcctc acaaagtgct gggattacag gtgtgaacca ctgctcccgg ccttgtgtga    7560
ttttatctaa gggacttaag cgtcctcagg tcctaggggg tcgtgaaacc aaaaccccag    7620
ggatagcaag ggacaattgt atcttcaaag tagacaaatg gcgccgggca cggtggctca    7680
cgcctgtaat cccagcagtt tccgaggctg aggcaggcgg ctcacctgag gtcaggagtt    7740
ggagaccagc ctggccaaca tgctgaaacc ctgtctgtac aaaaatacaa aaatagctgg    7800
gcatggtggc gcatgcctgt agtcccagct actagagcga ctgaggcagg agaattgctt    7860
gaacctggga ggcggaggtt gcagggagcc aagatggcgc caccgcactc cagcctaggt    7920
gatagagtga gactccctct caaaaacaaa acaaaacaaa aaaattagac aaatgctaca    7980
ttaatgtttg ggtggtcaga ttctactttg aatctgaagt ttgcagatat gcctatagat    8040
ttttggagtt taccactttc ttattctgta tcattaatgt aatatttaa attactatat    8100 atgttaccat ttttctggat ttagtaagaa atttgcagtt ttggtttgat gtaacaaggg    8160
ttttaatgta atttatgtta gattttgcat tttttccatt actgttatat tttaacctga    8220
ctgactgatc taattgtatt agtattgtga ataatcatgt gaaatgtttt gagacagagt    8280
actatatttg tgaatataat tttatggttt ttttcactta gaacctttct gtgtggaaaa    8340
ctaagaaaat tgctttctgc tgtataatct ggcattcatt gtagattaaa gcttattttt    8400
ctgtgaataa aacgtattca ataaaatact attctttaaa attatatcat aaaaaaaaaa    8460
```

<210> SEQ ID NO 19
<211> LENGTH: 3813

<212> TYPE: DNA
<213> ORGANISM: Homo sapiens

<400> SEQUENCE: 19

```
aacgctggtc ctcggccggg cgcgctgacg tcatcgtgcg tcagagtgag cccggatggg      60
gcggcgggct tcgggagcgc ccgggctgat ccgagccgag cgggccgtat ctccttgtcg     120
gcgccgctga ttcccggctc tgcggaggcc tctaggcagc cgcgcagctt ccgtgtttgc     180
tgcgcccgca ctgcgattta caaccctgaa gaatctccct atccctattt tgtcccctg      240
cagtaataaa tcccattatg gagatctcga aactttataa agggatatag tttgaattct     300
atggagtgta attttgtgta tgaattatat ttttaaaaca ttgaagagtt ttcagaaaga     360
aggctagtag agttgattac tgatacttta tgctaagcag tacttttttg gtagtacaat     420
attttgttag gcgtttctga taacactaga aaggacaagt tttatcttgt gataaattga     480
ttaatgttta caacatgact gataattata gctgaatagt ccttaaatga tgaacaggtt     540
atttagtttt taaatgcagt gtaaaaagtg tgctgtggaa attttatggc taactaagtt     600
tatggagaaa ataccttcag ttgatcaaga ataatagtgg tatacaaagt taggaagaaa     660
gtcaacatga tgctgcagga aatggaaaca aatacaaatg atatttaaca aagatagagt     720
ttacagtttt tgaactttaa gccaaattca tttgacatca agcactatag caggcacagg     780
ttcaacaaag cttgtgggta ttgacttccc ccaaaagttg tcagctgaag taatttagcc     840
cacttaagta aatactatga tgataagctg tgtgaactta gcttttaaat agtgtgacca     900
tatgaaggtt ttaattactt ttgtttattg gaataaaatg agatttttg ggttgtcatg      960
ttaaagtgct tatagggaaa gaagcctgca tataattttt taccttgtgg cataatcagt    1020
aattggtctg ttattcaggc ttcatagctt gtaaccaaat ataaataaaa ggcataattt    1080
aggtattcta tagttgctta gaattttgtt aatataaatc tctgtgaaaa atcaaggagt    1140
tttaatattt tcagaagtgc atccacctt cagggcttta agttagtatt actcaagatt     1200
atgaacaaat agcacttagg ttacctgaaa gagttactac aaccccaaag agttgtgttc    1260
taagtagtat cttggtaatt cagagagata ctcatcctac ctgaatataa actgagataa    1320
atccagtaaa gaaagtgtag taaattctac ataagagtct atcattgatt tcttttttgtg   1380
gtaaaaatct tagttcatgt gaagaaattt catgtgaatg ttttagctat caaacagtac    1440
tgtcacctac tcatgcacaa aactgcctcc caaagacttt tcccaggtcc ctcgtatcaa    1500
aacattaaga gtataatgga agatagcacg atcttgtcag attggacaaa cagcaacaaa    1560
caaaaaatga agtatgactt ttcctgtgaa ctctacagaa tgtctacata ttcaactttc    1620
cccgccgggg tgcctgtctc agaaaggagt cttgctcgtg ctggttttta ttatactggt    1680
gtgaatgaca aggtcaaatg cttctgttgt ggcctgatgc tggataactg gaaactagga    1740
gacagtccta ttcaaaagca taaacagcta tatcctagct gtagctttat tcagaatctg    1800
gtttcagcta gtctgggatc cacctctaag aatacgtctc caatgagaaa cagttttgca    1860
cattcattat ctcccacctt ggaacatagt agcttgttca gtggttctta ctccagcctt    1920
tctccaaacc ctcttaattc tagagcagtt gaagacatct cttcatcgag gactaacccc    1980
tacagttatg caatgagtac tgaagaagcc agatttctta cctaccatat gtggccatta    2040
acttttttgt caccatcaga attggcaaga gctggttttt attatatagg acctggagat    2100
agggtagcct gctttgcctg tggtgggaag ctcagtaact gggaaccaaa ggatgatgct    2160
atgtcagaac accggaggca ttttcccaac tgtccatttt tggaaaattc tctagaaact    2220
```

```
ctgaggttta gcatttcaaa tctgagcatg cagacacatg cagctcgaat gagaacattt     2280
atgtactggc catctagtgt tccagttcag cctgagcagc ttgcaagtgc tggtttttat     2340
tatgtgggtc gcaatgatga tgtcaaatgc ttttgttgtg atggtggctt gaggtgttgg     2400
gaatctggag atgatccatg ggtagaacat gccaagtggt ttccaaggtg tgagttcttg     2460
atacgaatga aaggccaaga gtttgttgat gagattcaag gtagatatcc tcatcttctt     2520
gaacagctgt tgtcaacttc agataccact ggagaagaaa atgctgaccc accaattatt     2580
cattttggac ctggagaaag ttcttcagaa gatgctgtca tgatgaatac acctgtggtt     2640
aaatctgcct tggaaatggg ctttaataga gacctggtga acaaacagt tcaaagtaaa      2700
atcctgacaa ctggagagaa ctataaaaca gttaatgata ttgtgtcagc acttcttaat     2760
gctgaagatg aaaaaagaga gaggagaag gaaaaacaag ctgaagaaat ggcatcagat      2820
gatttgtcat taattcggaa gaacagaatg gctctctttc aacaattgac atgtgtgctt     2880
cctatcctgg ataatctttt aaaggccaat gtaattaata acaggaaca tgatattatt     2940
aaacaaaaaa cacagatacc tttacaagcg agagaactga ttgataccat tttggttaaa    3000
ggaaatgctg cggccaacat cttcaaaaac tgtctaaaag aaattgactc tacattgtat    3060
aagaacttat ttgtggataa gaatatgaag tatattccaa cagaagatgt ttcaggtctg    3120
tcactggaag aacaattgag gaggttgcaa gaagaacgaa cttgtaaagt gtgtatggac    3180
aaagaagttt ctgttgtatt tattccttgt ggtcatctgg tagtatgcca ggaatgtgcc    3240
ccttctctaa gaaaatgccc tatttgcagg ggtataatca agggtactgt tcgtacattt    3300
ctctcttaaa gaaaaatagt ctatatttta acctgcataa aaaggtcttt aaaatattgt    3360
tgaacacttg aagccatcta agtaaaaag ggaattatga gttttttcaat tagtaacatt     3420
catgttctag tctgctttgg tactaataat cttgttctg aaaagatggt atcatatatt      3480
taatcttaat ctgtttattt acaagggaag atttatgttt ggtgaactat attagtatgt    3540
atgtgtacct aagggagtag tgtcactgct tgttatgcat catttcagga gttactggat    3600
ttgttgttct ttcagaaagc tttgaatact aaattatagt gtagaaaaga actggaaacc    3660
aggaactctg gagttcatca gagttatggt gccgaattgt ctttggtgct tttcacttgt    3720
gttttaaaat aaggattttt ctcttatttc tcccctagt ttgtgagaaa catctcaata     3780
aagtgcttta aaagaaaaa aaaaaaaaa aaa                                    3813
```

<210> SEQ ID NO 20
<211> LENGTH: 6932
<212> TYPE: DNA
<213> ORGANISM: Homo sapiens

<400> SEQUENCE: 20

```
gcatttaaaa gacagcgtga gactcgcgcc ctccggcacg gaaaaggcca ggcgacaggt       60
gtcgcttgaa aagactgggc ttgtccttgc tggtgcatgc gtcgtcggcc tctgggcagc      120
aggtttacaa aggaggaaaa cgacttcttc tagattttt tttcagtttc ttctataaat       180
caaaacatct caaaatggag acctaaaatc cttaagggga cttagtctaa tctcgggagg      240
tagttttgtg catgggtaaa caaattaagt attaactggt gttttactat ccaaagaatg      300
ctaatttat aaacatgatc gagttatata aggtatacca taatgagttt gattttgaat       360
ttgatttgtg gaaataaagg aaaagtgatt ctagctgggg catattgtta aagcattttt      420
ttcagagttg gccaggcagt ctcctactgg cacattctcc cattatgtag aatagaaata      480
gtacctgtgt ttgggaaaga ttttaaaatg agtgacagtt atttggaaca aagagctaat      540
```

```
aatcaatcca ctgcaaatta aagaaacatg cagatgaaag ttttgacaca ttaaaatact    600
tctacagtga caaagaaaaa tcaagaacaa agcttttga tatgtgcaac aaatttagag    660
gaagtaaaaa gataaatgtg atgattggtc aagaaattat ccagttattt acaaggccac    720
tgatatttta aacgtccaaa agtttgttta aatgggctgt taccgctgag aatgatgagg    780
atgagaatga tggttgaagg ttacatttta ggaaatgaag aaacttagaa aattaatata    840
aagacagtga tgaatacaaa gaagatttt ataacaatgt gtaaaatttt tggccaggga    900
aaggaatatt gaagttagat acaattactt acctttgagg gaataattg ttggtaatga    960 gatgtgatgt ttctcctgcc acctggaaac aaagcattga agtctgcagt tgaaaagccc   1020
aacgtctgtg agatccagga accatgctt gcaaaccact ggtaaaaaaa aaaaaaaaa    1080 aaaaaaaag ccacagtgac ttgcttattg gtcattgcta gtattatcga ctcagaacct   1140
ctttactaat ggctagtaaa tcataattga gaaattctga attttgacaa ggtctctgct   1200
gttgaaatgg taaatttatt attttttttg tcatgataaa ttctggttca aggtatgcta   1260
tccatgaaat aatttctgac caaaactaaa ttgatgcaat ttgattatcc atcttagcct   1320
acagatggca tctggtaact tttgactgtt ttaaaaata aatccactat cagagtagat   1380
ttgatgttgg cttcagaaac atttagaaaa acaaaagttc aaaaatgttt tcaggaggtg   1440
ataagttgaa taactctaca atgttagttc tttgaggggg acaaaaaatt taaaatcttt   1500
gaaaggtctt attttacagc catatctaaa ttatcttaag aaaatttta acaaagggaa   1560 tgaaatatat atcatgattc tgttttcca aaagtaacct gaatatagca atgaagttca   1620
gttttgttat tggtagtttg ggcagagtct cttttgcag cacctgttgt ctaccataat   1680
tacagaggac atttccatgt tctagccaag tatactatta gaataaaaaa acttaacatt   1740
gagttgcttc aacagcatga aactgagtcc aaaagaccaa atgaacaaac acattaatct   1800
ctgattattt atttaaata gaatatttaa ttgtgtaaga tctaaatgta tcattatact   1860
taagcaatca tattcctgat gatctatggg aaataactat tatttaatta atattgaaac   1920
caggttttaa gatgtgttag ccagtcctgt tactagtaaa tctctttatt tggagagaaa   1980
ttttagattg ttttgttctc cttattagaa ggattgtaga aagaaaaaa tgactaattg   2040 gagaaaaatt ggggatatat catatttcac tgaattcaaa atgtcttcag ttgtaaatct   2100
taccattatt ttacgtacct ctaagaaata aaagtgcttc taattaaaat atgatgtcat   2160
taattatgaa atacttcttg ataacagaag ttttaaaata gccatcttag aatcagtgaa   2220
atatggtaat gtattatttt cctcctttga gttaggtctt gtgcttttt ttcctggcca   2280 ctaaatttca caatttccaa aaagcaaaat aaacatattc tgaatatttt tgctgtgaaa   2340
cacttgacag cagagctttc caccatgaaa agaagcttca tgagtcacac attacatctt   2400
tgggttgatt gaatgccact gaaacattct agtagcctgg agaagttgac ctacctgtgg   2460
agatgcctgc cattaaatgg catcctgatg gcttaataca catcactctt ctgtgaaggg   2520
ttttaatttt caacacagct tactctgtag catcatgttt acattgtatg tataaagatt   2580
atacaaaggt gcaattgtgt atttcttcct taaaatgtat cagtatagga tttagaatct   2640
ccatgttgaa actctaaatg catagaaata aaaataataa aaaattttc attttggctt   2700 ttcagcctag tattaaaact gataaaagca aagccatgca caaaactacc tccctagaga   2760
aaggctagtc ccttttcttc cccattcatt tcattatgaa catagtagaa aacagcatat   2820
tcttatcaaa tttgatgaaa agcgccaaca cgtttgaact gaaatacgac ttgtcatgtg   2880
```

```
aactgtaccg aatgtctacg tattccactt ttcctgctgg ggttcctgtc tcagaaagga    2940
gtcttgctcg tgctggtttc tattacactg gtgtgaatga caaggtcaaa tgcttctgtt    3000
gtggcctgat gctggataac tggaaaagag gagacagtcc tactgaaaag cataaaaagt    3060
tgtatcctag ctgcagattc gttcagagtc taaattccgt taacaacttg gaagctacct    3120
ctcagcctac ttttccttct tcagtaacaa attccacaca ctcattactt ccgggtacag    3180
aaaacagtgg atatttccgt ggctcttatt caaactctcc atcaaatcct gtaaactcca    3240
gagcaaatca agatttttct gccttgatga gaagttccta ccactgtgca atgaataacg    3300
aaaatgccag attacttact tttcagacat ggccattgac ttttctgtcg ccaacagatc    3360
tggcaaaagc aggcttttac tacataggac ctggagacag agtggcttgc tttgcctgtg    3420
gtggaaaatt gagcaattgg gaaccgaagg ataatgctat gtcagaacac ctgagacatt    3480
ttcccaaatg cccatttata gaaaatcagc ttcaagacac ttcaagatac acagtttcta    3540
atctgagcat gcagacacat gcagcccgct ttaaaacatt cttttaactgg ccctctagtg    3600 ttctagttaa tcctgagcag cttgcaagtg cgggttttta ttatgtgggt aacagtgatg    3660
atgtcaaatg cttttgctgt gatggtggac tcaggtgttg ggaatctgga gatgatccat    3720
gggttcaaca tgccaagtgg tttccaaggt gtgagtactt gataagaatt aaaggacagg    3780
agttcatccg tcaagttcaa gccagttacc ctcatctact gaacagctg ctatccacat    3840 cagacagccc aggagatgaa aatgcagagt catcaattat ccattttgaa cctggagaag    3900
accattcaga agatgcaatc atgatgaata ctcctgtgat taatgctgcc gtggaaatgg    3960
gctttagtag aagcctggta aaacagacag ttcagagaaa atcctagca actggagaga    4020 attatagact agtcaatgat cttgtgttag acttactcaa tgcagaagat gaaataaggg    4080
aagaggagag agaaagagca actgaggaaa aagaatcaaa tgatttatta ttaatccgga    4140
agaatagaat ggcactttt caacatttga cttgtgtaat tccaatcctg gatagtctac    4200
taactgccgg aattattaat gaacaagaac atgatgttat taaacagaag acacagacgt    4260 cttttacaagc aagagaactg attgatacga ttttagtaaa aggaaatatt gcagccactg    4320
tattcagaaa ctctctgcaa gaagctgaag ctgtgttata tgagcattta tttgtgcaac    4380
aggacataaa atatattccc acagaagatg tttcagatct accagtggaa gaacaattgc    4440
ggagactaca agaagaaga acatgtaaag tgtgtatgga caagaagtg tccatagtgt    4500 ttattccttg tggtcatcta gtagtatgca aagattgtgc tccttcttta agaaagtgtc    4560
ctatttgtag gagtacaatc aagggtacag ttcgtacatt tctttcatga agaagaacca    4620
aaacatcgtc taaactttag aattaattta ttaaatgtat tataactta acttttatcc    4680 taatttggtt tccttaaaat ttttatttat ttacaactca aaaacattg ttttgtgtaa    4740 catatttata tatgtatcta aaccatatga acatatattt tttagaaact aagagaatga    4800
taggcttttg ttcttatgaa cgaaaaagag gtagcactac aaaacacaata ttcaatcaaa    4860 atttcagcat tattgaaatt gtaagtgaag taaaacttaa gatatttgag ttaacccttta    4920 agaattttaa atattttggc attgtactaa taccgggaac atgaagccag gtgtggtggt    4980
atgtgcctgt agtcccaggc tgaggcaaga gaattacttg agcccaggag tttgaatcca    5040
tcctgggcag catactgaga ccctgccttt aaaaacaaac agaacaaaaa caaaacacca    5100
gggacacatt tctctgtctt ttttgatcag tgtcctatac atcgaaggtg tgcatatatg    5160
ttgaatgaca ttttagggac atggtgtttt tataaagaat tctgtgagaa aaatttaat    5220 aaagcaacaa aaattactct tattcttcat tgctttattt caatgacatt ggatagttta    5280
```

```
gtcactccca gactctttcc ataccttctt aaagcctctc aaatattgaa ctacagttta    5340
tactccttcc cataagatgc ttcttcattg acacttgtag aacacggggt caacacatca    5400
taaaatctat tatggaatgc ctgagacaag aatcaaacag tcccctttagt aagtttgttt    5460 attcacttct ctattgattc attcaagaag tctcatgcca gccccaccta ttggaagaag    5520
gtctgagttt tattcttatc tctttggtat taattctgaa acttagaaag tacactggtt    5580
agcaatgctt gggaccaaca ggttgttctg gtaaataaat ctgtttcata ttgtcagtgc    5640
aacaaaatgt cccccctctgc attatgttat tggtactcaa cacgtccgag tcataactct    5700
gtcctttgct tcttatagag gtattaggtc ttcaagagca gaagtaagac tgtaataggg    5760
aatactcagg ggaaggcagg caaaggctag tcatctaaac cagttctaga tgtctgtata    5820
ggggcagatg gctctgtaag ggcagaaggg aaagacccct tcataagggt cacagctgac    5880
aatcctataa caaaagacag gttaacaaga gaaaaactta acaaatttat ttaatcacag    5940
atttacatca ccggggagcc ttcgtaatga agatccaaaa ttacagggga aactgtgcat    6000
ttttatgctt aggtttgata tgaatggac  agccctgaag aatagtgatt ggaaaaaaag    6060
gatatgatct aatgggaata gacacaggtt ggggacccag caaggcctgt ctgttcagat    6120
tattcttggt ctctgtgcag cattccttcc tcctggatat agggcagggc ctgtatggga    6180
tggggatatt ataacctgct atcaagcaag gtaggtcaga gaatttattt atggccagct    6240
cttacatagt taggtgagga aagattagag tactatcttt aagatgtaag tctggcattg    6300
tggaaagatg gttccagttt ctatgaccta ccttggggaa gaggaattca agtttctgtg    6360
gcttgccttc agggagaatg aggctgagac aggagggcag gataacatca gagaaaaact    6420
ttgcttctga ggccttcact ttgggttttc tgagccccaa catctgctag tgttgtaaag    6480
agaacaatta gggaccaagt gaggggagga aagaatccat ctctgcattc tgatgctggg    6540
agacttattt ccttgaaatg caattgattt tgcctctgct aagaggctct gctggctacc    6600
catgtactag ccagtgtcct gcatgggtgc taggctgaat tatttgtaat tgtgcttagg    6660
tgatttgtaa ctcaggtata gggtatttaa atagtaggca ccctttttgc accatgtgtt    6720
ttttttttta tctagttctt gtatactaca gataatattt gaactttgtc atctcactgt    6780 aaaactttg ttcatttctc attatggtaa taaatagcta ttataaccaa cccatttatt    6840
caaatatgtt atttccctaa gtgttatttt gacattttgt tttggaaaaa ataaatcacc    6900
atagataata aaaaaaaaaa aaaaaaaaaa aa                                  6932
```

<210> SEQ ID NO 21
<211> LENGTH: 14796
<212> TYPE: DNA
<213> ORGANISM: Homo sapiens

<400> SEQUENCE: 21

```
tctagacatg cggatatatt caagctgggc acagcacagc agccccaccc caggcagctt      60
gaaatcagag ctggggtcca aagggaccac accccgaggg actgtgtggg ggtcggggca     120
cacaggccac tgcttccccc cgtctttctc agccattcct gaagtcagcc tcactctgct     180
tctcagggat ttcaaatgtg cagagactct ggcacttttg tagaagcccc ttctggtcct     240
aacttacacc tggatgctgt ggggctgcag ctgctgctcg ggctcgggag gatgctgggg     300
gcccggtgcc catgagcttt tgaagctcct ggaactcggt tttgagggtg ttcaggtcca     360
ggtggacacc tgggctgtcc ttgtccatgc atttgatgac attgtgtgca gaagtgaaaa     420
```

```
ggagttaggc cgggcatgct ggcttatgcc tgtaatccca gcactttggg aggctgaggc    480
gggtggatca cgaggtcagg agttcaatac cagcctggcc aagatggtga aaccccgtct    540
ctactaaaaa tacaaaaaaa ttagccgggc atggtggcgg gcgcatgtaa tcccagctac    600
tgggggggct gaggcagaga attgctggaa cccaggagat ggaggttgca gtgagccaag    660
attgtgccac tgcactgcac tccagcctgg cgacagagca agactctgtc tcaaaaaaaa    720
aaaaaaaaag tgaaaggag ttgttccttt cctccctcct gagggcaggc aactgctgcg     780
gttgccagtg gaggtggtgc gtccttggtc tgtgcctggg ggccacccca gcagaggcca    840
tggtggtgcc agggcccggt tagcgagcca atcagcagga cccaggggcg acctgccaaa    900
gtcaactgga tttgataact gcagcgaagt taagtttcct gattttgatg attgtgttgt    960
ggttgtgtaa gagaatgaag tatttcgggg tagtatggta atgccttcaa cttacaaacg   1020
gttcaggtaa accacccata tacatacata tacatgcatg tgatatatac acatacaggg   1080
atgtgtgtgt gttcacatat atgaggggag agagactagg ggagagaaag taggttgggg   1140
agagggagag agaaaggaaa acaggagaca gagagagagc ggggagtaga gagagggaag   1200
gggtaagaga gggagaggag gagagaaagg gaggaagaag cagagagtga atgttaaagg   1260
aaacaggcaa aacataaaca gaaaatctgg gtgaagggta tatgagtatt ctttgtacta   1320
ttcttgcaat tatcttttat ttaaattgac atcgggccgg gcgcagtggc tcacatctgt   1380
aatcccagca ctttgggagg ccgaggcagg cagatcactt gaggtcagga gtttgagacc   1440
agcctggcaa acatggtgaa accccatctc tactaaaaat acaaaaatta gcctggtgtg   1500
gtggtgcatg cctttaatct cagctactcg ggaggctgag gcaggagaat cgcttgaacc   1560
cgtggcgggg aggaggttgc agtgagctga gatcatgcca ctgcactcca gcctgggcga   1620
tagagcgaga ctcagtttca aataaataaa taaacatcaa aataaaaagt tactgtatta   1680
aagaatgggg gcggggtggg aggggtgggg agaggttgca aaaataaata aataaataaa   1740
taaaccccaa aatgaaaaag acagtggagg caccaggcct gcgtggggct ggagggctaa   1800
taaggccagg cctcttatct ctggccatag aaccagagaa gtgagtggat gtgatgccca   1860
gctccagaag tgactccaga acaccctgtt ccaaagcaga ggacacactg attttttttt   1920
taataggctg caggacttac tgttggtggg acgccctgct ttgcgaaggg aaaggaggag   1980
tttgccctga gcacaggccc ccaccctcca ctgggctttc cccagctccc ttgtcttctt   2040
atcacggtag tggcccagtc cctggcccct gactccagaa ggtggccctc ctggaaaccc   2100
aggtcgtgca gtcaacgatg tactcgccgg gacagcgatg tctgctgcac tccatccctc   2160
ccctgttcat ttgtccttca tgcccgtctg gagtagatgc ttttttgcaga ggtggcaccc   2220 tgtaaagctc tcctgtctga cttttttttt tttttttagac tgagttttgc tcttgttgcc   2280
taggctggag tgcaatggca caatctcagc tcactgcacc ctctgcctcc cgggttcaag   2340
cgattctcct gcctcagcct cccgagtagt tgggattaca ggcatgcacc accacgccca   2400 gctaatttttt gtatttttag tagagacaag gtttcaccgt gatggccagg ctggtcttga   2460
actccaggac tcaagtgatg ctcctgccta ggcctctcaa agtgttggga ttacaggcgt   2520
gagccactgc acccggcctg cacgcgttct ttgaaagcag tcgaggggc gctaggtgtg    2580 ggcagggacg agctggcgcg gcgtcgctgg gtgcaccgcg accacgggca gagccacgcg   2640
gcgggaggac tacaactccc ggcacacccc gcgccgcccc gcctctactc ccagaaggcc   2700 gcgggggtg gaccgcctaa gagggcgtgc gctcccgaca tgccccgcgg cgcgccatta    2760
accgccagat ttgaatcgcg ggacccgttg gcagaggtgg cggcggcggc atgggtgccc   2820
```

```
cgacgttgcc ccctgcctgg cagcccttc tcaaggacca ccgcatctct acattcaaga    2880 actggcccctt cttggagggc tgcgcctgca ccccggagcg ggtgagactg cccggcctcc    2940
tggggtcccc cacgcccgcc ttgccctgtc cctagcgagg ccactgtgac tgggcctcgg    3000
gggtacaagc cgccctcccc tccccgtcct gtccccagcg aggccactgt ggctgggccc    3060
cttgggtcca ggccggcctc ccctcccctgc tttgtcccca tcgaggcctt tgtggctggg    3120 cctcgggggtt ccgggctgcc acgtccactc acgagctgtg ctgtcccttg cagatggccg    3180
aggctggctt catccactgc cccactgaga acgagccaga cttggcccag tgtttcttct    3240
gcttcaagga gctggaaggc tgggagccag atgacgaccc catgtaagtc ttctctggcc    3300
agcctcgatg ggctttgttt tgaactgagt tgtcaaaaga tttgagttgc aaagacactt    3360
agtatgggag ggttgctttc caccctcatt gcttcttaaa cagctgttgt gaacggatac    3420
ctctctatat gctggtgcct tggtgatgct tacaacctaa ttaaatctca tttgaccaaa    3480
atgccttggg gtggacgtaa gatgcctgat gcctttcatg ttcaacagaa tacatcagca    3540
gaccctgttg ttgtgaactc ccaggaatgt ccaagtgctt tttttgagat tttttaaaaa    3600
acagtttaat tgaaatataa cctacacagc acaaaaatta cccttttgaaa gtgtgcactt    3660 cacactttcg gaggctgagg cgggcggatc acctgaggtc aggagttcaa gacctgcctg    3720
gccaacttgg cgaaaccccg tctctactaa aaatacaaaa attagccggg catggtagcg    3780
cacgcccgta atcccagcta ctcgggaggc taaggcagga gaatcgcttg aacctgggag    3840
gcggaggttg cagtgagccg agattgtgcc aatgcactcc agcctcggcg acagagcgag    3900
actccgtcat aaaaataaaa aattgaaaaa aaaaaagaa agaaagcata tacttcagtg    3960
ttgttctgga ttttttttctt caagatgcct agttaatgac aatgaaattc tgtactcgga    4020
tggtatctgt cttccacac tgtaatgcca tattcttttc tcaccttttt ttctgtcgga    4080
ttcagttgct tccacagctt taattttttt cccctggaga atcacccag ttgttttttct    4140 ttttggccag aagagagtag ctgttttttt tcttagtatg tttgctatgg tggttatact    4200
gcatccccgt aatcactggg aaagatcag tggtattctt cttgaaaatg aataagtgtt    4260 atgatattt cagattagag ttacaactgg ctgtcttttt ggactttgtg tggccatgtt    4320
ttcattgtaa tgcagttctg gtaacggtga tagtcagtta tacagggaga ctcccctagc    4380
agaaaatgag agtgtgagct aggggtgtccc ttggggaacc cggggcaata atgcccttct    4440
ctgcccttaa tccttacagt gggccgggca cggtggctta cgcctgtaat accagcactt    4500
tgggaggccg aggcgggcgg atcacgaggt caggagatcg agaccatctt ggctaatacg    4560
gtgaaacccc gtctccacta aaaatacaaa aaattagccg ggcgtggtgg tgggcgcctg    4620
tagtcccagc tactcgggag gctgaggcag gagaatggcg tgaacccagg aggcggagct    4680
tgcagtgagc cgagattgca ccactgcact ccagcctggg cgacagaatg agactccgtc    4740
tcaaaaaaaa aaaaaaaga aaaaaatctt tacagtggat tacataacaa ttccagtgaa    4800
atgaaattac ttcaaacagt tccttgagaa tgttggaggg atttgacatg taattccttt    4860
ggacatatac catgtaacac ttttccaact aattgctaag gaagtccaga taaaatagat    4920
acattagcca cacagatgtg gggggagatg tccacaggga gagagaaggt gctaagaggt    4980
gccatatggg aatgtggctt gggcaaagca ctgatgccat caacttcaga cttgacgtct    5040
tactcctgag gcagagcagg gtgtgcctgt ggagggcgtg gggaggtggc ccgtggggag    5100
tggactgccg cttaatccc ttcagctgcc tttccgctgt tgttttgatt tttctagaga    5160
```

-continued

| | | | | |
|---|---|---|---|---|
| ggaacataaa | aagcattcgt | ccggttgcgc | tttccttctt | gtcaagaagc | agtttgaaga | 5220 |
| attaacccctt | ggtgaatttt | tgaaactgga | cagagaaaga | gccaagaaca | aaattgtatg | 5280 |
| tattgggaat | aagaactgct | caaaccctgt | tcaatgtctt | tagcactaaa | ctacctagtc | 5340 |
| cctcaaaggg | actctgtgtt | ttcctcagga | agcattttt | tttttttct | gagatagagt | 5400 |
| ttcactcttg | ttgcccaggc | tggagtgcaa | tggtgcaatc | ttggctcact | gcaacctctg | 5460 |
| cctctcgggt | tcaagtgatt | ctcctgcctc | agcctcccaa | gtaactggga | ttacagggaa | 5520 |
| gtgccaccac | acccagctaa | tttttgtatt | tttagtagag | atggggtttc | accacattgc | 5580 |
| ccaggctggt | cttgaactcc | tgacctcgtg | attcgcccac | cttggcctcc | caaagtgctg | 5640 |
| ggattacagg | cgtgaaccac | cacgcctggc | tttttttttt | ttgttctgag | acacagtttc | 5700 |
| actctgttac | ccaggctgga | gtagggtggc | ctgatctcgg | atcactgcaa | cctccgcctc | 5760 |
| ctgggctcaa | gtgatttgcc | tgcttcagcc | tcccaagtag | ccgagattac | aggcatgtgc | 5820 |
| caccacaccc | aggtaatttt | tgtatttttg | gtagagacga | ggtttcacca | tgttggccag | 5880 |
| gctggttttg | aactcctgac | ctcaggtgat | ccacccgcct | cagcctccca | aagtgctgag | 5940 |
| attataggtg | tgagccacca | cacctggcct | caggaagtat | ttttattttt | aaatttattt | 6000 |
| atttatttga | gatggagtct | tgctctgtcg | cccaggctag | agtgcagcga | cgggatctcg | 6060 |
| gctcactgca | agctccgccc | cccaggttca | agccattctc | ctgcctcagc | ctcccgagta | 6120 |
| gctgggacta | caggcgcccg | ccaccacacc | cggctaattt | ttttgtattt | ttagtagaga | 6180 |
| cgggttttca | ccgtgttagc | caggagggtc | ttgatctcct | gacctcgtga | tctgcctgcc | 6240 |
| tcggcctccc | aaagtgctgg | gattacaggt | gtgagccacc | acaccggct | atttttattt | 6300 |
| ttttgagaca | gggactcact | ctgtcacctg | gctgcagtg | cagtggtaca | ccatagctca | 6360 |
| ctgcagcctc | gaactcctga | gctcaagtga | tcctcccacc | tcatcctcac | aagtaattgg | 6420 |
| gactacaggt | gcaccccacc | atgcccacct | aatttattta | tttatttatt | tatttatttt | 6480 |
| catagagatg | agggttccct | gtgttgtcca | ggctggtctt | gaactcctga | gctcacggga | 6540 |
| tccttttgcc | tgggcctccc | aaagtgctga | gattacaggc | atgagccacc | gtgcccagct | 6600 |
| aggaatcatt | tttaaagccc | ctaggatgtc | tgtgtgattt | taaagctcct | ggagtgtggc | 6660 |
| cggtataagt | atataccggt | ataagtaaat | cccacatttt | gtgtcagtat | ttactagaaa | 6720 |
| cttagtcatt | tatctgaagt | tgaaatgtaa | ctgggcttta | tttatttatt | tatttattta | 6780 |
| tttattttta | atttttttt | ttgagacgag | tctcactttg | tcacccaggc | tggagtgcag | 6840 |
| tggcacgatc | tcggctcact | gcaacctctg | cctcccgggg | tcaagcgatt | ctcctgcctt | 6900 |
| agcctcccga | gtagctggga | ctacaggcac | gcaccaccat | gcctggctaa | tttttgtatt | 6960 |
| tttagtagac | ggggtttcac | catgctggcc | aagctggtct | caaactcctg | accttgtgat | 7020 |
| ctgcccgctt | tagcctccca | gagtgctggg | attacaggca | tgagccacca | tgcgtggtct | 7080 |
| ttttaaaatt | ttttgatttt | ttttttttt | gagacagagc | cttgctctgt | cgcccaggct | 7140 |
| ggagtgcagt | ggcacgatct | cagctcacta | caagctccgc | ctcccgggtt | cacgccattc | 7200 |
| ttctgcctca | gcctcctgag | tagctgggac | tacaggtgcc | caccaccacg | cctggctaat | 7260 |
| ttttttggt | atttttatta | gagacaaggt | ttcatcatgt | tggccaggct | ggtctcaaac | 7320 |
| tcctgacctc | aagtgatctg | cctgcctcgg | cctcccaaag | cgctgagatt | acaggtgtga | 7380 |
| tctactgcgc | caggcctggg | cgtcatatat | tcttatttgc | taagtctggc | agccccacac | 7440 |
| agaataagta | ctgggggatt | ccatatcctt | gtagcaaagc | cctgggtgga | gagtcaggag | 7500 |
| atgttgtagt | tctgtctctg | ccacttgcag | actttgagtt | taagccagtc | gtgctcatgc | 7560 |

```
tttccttgct aaatagaggt tagacccct atcccatggt ttctcaggtt gctttcagc    7620
ttgaaaattg tattcctttg tagagatcag cgtaaaataa ttctgtcctt atatgtggct  7680
ttattttaat ttgagacaga gtgtcactca gtcgcccagg ctggagtgtg gtggtgcgat  7740
cttggctcac tgcgacctcc acctcccagg ttcaagcgat tctcgtgcct caggctccca  7800
agtagctgag attataggtg tgtgccacca ggcccagcta acttttgtat ttttagtaga  7860
gacagggttt tgccatgttg gctaagctgg tctcgaactc ctggcctcaa gtgatctgcc  7920
cgccttggca tcccaaagtg ctgggattac aggtgtgaac caccacacct ggcctcaata  7980
tagtggcttt taagtgctaa ggactgagat tgtgttttgt caggaagagg ccagttgtgg  8040
gtgaagcatg ctgtgagaga gcttgtcacc tggttgaggt tgtgggagct gcagcgtggg  8100
aactggaaag tgggctgggg atcatctttt tccaggtcag gggtcagcca gcttttctgc  8160
agcgtgccat agaccatctc ttagccctcg tgggtcagag tctctgttgc atattgtctt  8220
ttgttgtttt tcacaacctt ttagaaacat aaaaagcatt cttagcccgt gggctggaca  8280
aaaaaaggcc atgacgggct gtatggattt ggcccagcag gcccttgctt gccaagccct  8340
gttttagaca aggagcagct tgtgtgcctg gaaccatcat gggcacaggg gaggagcaga  8400
gtggatgtgg aggtgtgagc tggaaaccag gtcccagagc gctgagaaag acagagggtt  8460
tttgcccttg caagtagagc aactgaaatc tgacaccatc cagttccaga aagccctgaa  8520
gtgctggtgg acgctgcggg gtgctccgct ctagggttac agggatgaag atgcagtctg  8580
gtaggggga tccactcacc tgttggaaga tgtgattaag aaaagtagac tttcagggcc  8640
gggcatggtg gctcacgcct gtaatcccag cactttggga ggccgaggcg ggtggatcac  8700
gaggtcagga gatcgagacc atcctggcta acatggtgaa accccgtctt tactaaaaat  8760
acaaaaaatt agctgggcgt ggtggcgggc gcctgtagtc ccagctactc gggaggctga  8820
ggcaggagaa tggcgtgaac ctgggaggtg gagcttgctg tgagccgaga tcgcgccact  8880
gcactccagc ctgggcgaca gagcgagact ccgtctcaaa aaaaaaaaa aagtaggct   8940
ttcatgatgt gtgagctgaa ggcgcagtag gcagaagtag aggcctcagt ccctgcagga  9000
gaccctcgg tctctatctc ctgatagtca gacccagcca cactggaaag aggggagaca   9060
ttacagcctg cgagaaaagt agggagattt aaaaactgct tggcttttat tttgaactgt  9120
tttttttgtt tgtttgtttt ccccaattca gaatacagaa tacttttatg gatttgtttt  9180
tattacttta attttgaaac aatataatct tttttttgtt gttttttga cagggtct    9240
tactctgtca cccaggctga gtgcagtggt gtgatcttgg ctcacctcag cctcgacccc  9300
ctgggctcaa atgattctcc cacctcagct tcccaagtag ctgggaccac aggtgcgtgt  9360
gttgcgctat acaaatcctg aagacaagga tgctgttgct ggtgatgctg gggattccca  9420
agatcccaga tttgatggca ggatgcccct gtctgctgcc ttgccagggt gccaggaggg  9480
cgctgctgtg gaagctgagg cccggccatc cagggcgatg cattgggcgc tgattcttgt  9540
tcctgctgct gcctcggtgc ttagcttttg aaacaatgaa ataaattaga accagtgtga  9600
aaatcgatca gggaataaat ttaatgtgga aataaactga caacttagt tcttcataag   9660
agtttacttg gtaaatactt gtgatgagga caaaacgaag cactgaaagg agaggcgagt  9720
tgtagacctg ggtggcagga gtgttttgtt tgttttcttt ggcagggtct tgctctgttg  9780
ctcaggctgg agtacagtgg cacaatcaca gctcactata gcctcgacct cctgactca   9840
agcaatcctc ctgcctcagc ctcccagtag ctgggactac aggcgcatgc caccatgcct  9900
```

```
ggctaatttt aaattttttt ttttctcttt tttgagatgg aatctcactc tgtcgcccag    9960
gctggagtgc agtggcgtga tctcggctga cggcaagctc cgcctcccag gttcactcca   10020
ttcgcctgcc tcagcctccc aagtagctgg gactacaggc gctgggatta caaacccaaa   10080
cccaaagtgc tgggattaca ggcgtgagcc actgcacccg gcctgttttg tctttcaata   10140
gcaagagttg tgtttgcttc gcccctacct ttagtggaaa aatgtataaa atggagatat   10200
tgacctccac attggggtgg ttaaattata gcatgtatgc aaaggagctt cgctaattta   10260
aggctttttt gaaagagaag aaactgaata atccatgtgt gtatatatat tttaaaagcc   10320
atggtcatct ttccatatca gtaaagctga ggctccctgg gactgcagag ttgtccatca   10380
cagtccatta taagtgcgct gctgggccag gtgcagtggc ttgtgcctga atcccagcac   10440
tttgggaggc caaggcagga ggattcattg agcccaggag ttttgaggcg agcctgggca   10500
atgtggccag acctcatctc ttcaaaaaat acacaaaaaa ttagccaggc atggtggcac   10560
gtgcctgtag tctcagctac tcaggaggct gaggtgggag gatcactttg agccttgcag   10620
gtcaaagctg cagtaagcca tgatcttgcc actgcattcc agcctggatg acagagcgag   10680
accctgtctc taaaaaaaaa aaaaaccaaa cggtgcactg ttttctttt tcttatcaat   10740
ttattatttt taaattaaat tttcttttaa taatttataa attataaatt tatattaaaa   10800
aatgacaaat tttattact tatacatgag gtaaaactta ggatatataa agtacatatt   10860
gaaaagtaat ttttggctg gcacagtggc tcacacctgt aatcccagca ctttgggagg   10920
ccgtggcggg cagatcacat gagatcatga gttcgagacc aacctgacca acatggagag   10980
accccatctc tactaaaaat acaaaattag ccggggtggt ggcgcatgcc tgtaatccca   11040
gctactcggg aggctgaggc aggagaatct cttgaacccg ggaggcagag gttgcggtga   11100
gccaagatcg tgccttttgca caccagccta ggcaacaaga gcgaaagtcc gtctcaaaaa   11160
aaaagtaatt ttttttaagt taacctctgt cagcaaacaa atttaaccca ataaaggtct   11220
ttgtttttta atgtagtaga ggagttaggg tttataaaaa atatggtagg aaggggggtc   11280
cctggatttg ctaatgtgat tgtcatttgc cccttaggag agagctctgt tagcagaatg   11340
aaaaaattgg aagccagatt cagggaggga ctggaagcaa aagaatttct gttcgaggaa   11400
gagcctgatg tttgccaggg tctgtttaac tggacatgaa gaggaaggct ctggactttc   11460
ctccaggagt ttcaggagaa aggtagggca gtggttaaga gcagagctct gcctagacta   11520
gctggggtgc ctagactagc tggggtgccc agactagctg gggtgcctag actagctggg   11580
tactttgagt ggctccttca gcctggacct cggtttcctc acctgtatag tagagatatg   11640
ggagcaccca gcgcaggatc actgtgaaca taaatcagtt aatggaggaa gcaggtagag   11700
tggtgctggg tgcataccaa gcactccgtc agtgtttcct gttattcgat gattaggagg   11760
cagcttaaac tagagggagt tgagctgaat caggatgttt gtcccaggta gctgggaatc   11820
tgcctagccc agtgcccagt ttatttaggt gctctctcag tgttccctga ttgttttttc   11880
ctttgtcatc ttatctacag gatgtgactg ggaagctctg gtttcagtgt catgtgtcta   11940
ttctttattt ccaggcaaag gaaccaaca ataagaagaa agaatttgag gaaactgcga   12000
agaaagtgcg ccgtgccatc gagcagctgg ctgccatgaa ttgaggcctc tggccggagc   12060
tgcctggtcc cagagtggct gcaccacttc cagggtttat tccctggtgc caccagcctt   12120
cctgtgggcc ccttagcaat gtcttaggaa aggagatcaa catttttcaaa ttagatgttt   12180
caactgtgct cctgttttgt cttgaaagtg gcaccagagg tgcttctgcc tgtgcagcgg   12240
gtgctgctgg taacagtggc tgcttctctc tctctctctc ttttttgggg gctcattttt   12300
```

```
gctgttttga ttcccgggct taccaggtga gaagtgaggg aggaagaagg cagtgtccct    12360
tttgctagag ctgacagctt tgttcgcgtg ggcagagcct tccacagtga atgtgtctgg    12420
acctcatgtt gttgaggctg tcacagtcct gagtgtggac ttggcaggtg cctgttgaat    12480
ctgagctgca ggttccttat ctgtcacacc tgtgcctcct cagaggacag ttttttttgtt  12540 gttgtgtttt tttgttttttt tttttggta gatgcatgac ttgtgtgtga tgagagaatg   12600
gagacagagt ccctggctcc tctactgttt aacaacatgg ctttcttatt ttgtttgaat   12660
tgttaattca cagaatagca caaactacaa ttaaaactaa gcacaaagcc attctaagtc   12720 attgggaaa cggggtgaac ttcaggtgga tgaggagaca gaatagagtg ataggaagcg    12780
tctggcagat actccttttg ccactgctgt gtgattagac aggcccagtg agccgcgggg   12840
cacatgctgg ccgctcctcc ctcagaaaaa ggcagtggcc taaatccttt ttaaatgact   12900
tggctcgatg ctgtggggga ctggctgggc tgctgcaggc cgtgtgtctg tcagcccaac   12960
cttcacatct gtcacgttct ccacacgggg gagagacgca gtccgcccag gtccccgctt   13020
tctttggagg cagcagctcc cgcagggctg aagtctggcg taagatgatg gatttgattc   13080
gccctcctcc ctgtcataga gctgcagggt ggattgttac agcttcgctg gaaacctctg   13140
gaggtcatct cggctgttcc tgagaaataa aaagcctgtc atttcaaaca ctgctgtgga   13200
ccctactggg ttttttaaaat attgtcagtt tttcatcgtc gtccctagcc tgccaacagc   13260
catctgccca gacagccgca gtgaggatga gcgtcctggc agagacgcag ttgtctctgg   13320
gcgcttgcca gagccacgaa ccccagacct gtttgtatca tccgggctcc ttccgggcag   13380
aaacaactga aaatgcactt cagacccact tatttatgcc acatctgagt cggcctgaga   13440 tagactttc cctctaaact gggagaatat cacagtggtt tttgttagca gaaaatgcac    13500
tccagcctct gtactcatct aagctgctta ttttttgatat ttgtgtcagt ctgtaaatgg  13560
atacttcact ttaataactg ttgcttagta attggctttg tagagaagct ggaaaaaaat   13620
ggttttgtct tcaactcctt tgcatgccag gcggtgatgt ggatctcggc ttctgtgagc   13680
ctgtgctgtg ggcagggctg agctggagcc gcccctctca gcccgcctgc cacggccttt   13740
ccttaaaggc catccttaaa accagaccct catggctgcc agcacctgaa agcttcctcg   13800
acatctgtta ataaagccgt aggcccttgt ctaagcgcaa ccgcctagac tttcttcag    13860 atacatgtcc acatgtccat ttttcaggtt ctctaagttg gagtggagtc tgggaagggt   13920
tgtgaatgag gcttctgggc tatgggtgag gttccaatgg caggttagag cccctcgggc   13980
caactgccat cctggaaagt agagacagca gtgcccgctg cccagaagag accagcaagc   14040
caaactggag cccccattgc aggctgtcgc catgtggaaa gagtaactca caattgccaa   14100
taaagtctca tgtggtttta tctacttttt ttttctttttt ctttttttttt gagacaaggc 14160 cttgccctcc caggctggag tgcagtggaa tgaccacagc tcaccgcaac ctcaaattct   14220
tgcgttcaag tgaacctccc actttagcct cccaagtagc tgggactaca ggcgcacgcc   14280
atcacacccg gctaattgaa aatttttttt ttttgtttag atggaatctc actttgttgc   14340
ccaggctggt ctcaaactcc tgggctcaag tgatcatcct gcttcagcgt ccgacttgtt   14400
ggtattatag gcgtgagcca ctgggcctga cctagctacc atttttttaat gcagaaatga   14460 agacttgtag aaatgaaata acttgtccag gatagtcgaa taagtaactt ttagagctgg   14520
gatttgaacc caggcaatct ggctccagag ctgggccctc actgctgaag gacactgtca   14580
gcttgggagg gtggctatgg tcggctgtct gattctaggg agtgagggct gtctttaaag   14640
```

| | |
|---|---:|
| cacccccattc cattttcaga cagctttgtc agaaaggctg tcatatggag ctgacacctg | 14700 |
| cctcccccaag gcttccatag atcctctctg tacattgtaa ccttttattt tgaaatgaaa | 14760 |
| attcacagga agttgtaagg ctagtacagg ggatcc | 14796 |

<210> SEQ ID NO 22
<211> LENGTH: 4242
<212> TYPE: DNA
<213> ORGANISM: Homo sapiens

<400> SEQUENCE: 22

| | |
|---|---:|
| cttttgtctg tccgccgagc accccacttc accccattgg accgcgcggc cgccgctaga | 60 |
| gctctgcgcc tgcgcacgca ccgggccggg gactgggtgg cctggtgtgt gggcgcggca | 120 |
| gggcgcaggc gcaggcgcag tgtgcgtccg cgtctgaggg gagggatgtg ggggaagcga | 180 |
| cggccccccgg tttgtttggg ctgtgggcgg tgcgcagcgg agagcccggg aaaagcggga | 240 |
| aatggcggcg ccgagcgcgg ggtcttggtc caccttccag cacaaggagc tgatggccgc | 300 |
| tgacagggga cgcaggatat tgggagtgtg tggcatgcat cctcatcatc aggaaactct | 360 |
| aaaaaagaac cgagtggtgc tagccaaaca gctgttgttg agcgaattgt tagaacatct | 420 |
| tctggagaag gacatcatca ccttggaaat gagggagctc atccaggcca agtgggcag | 480 |
| tttcagccag aatgtggaac tcctcaactt gctgcctaag aggggtcccc aagcttttga | 540 |
| tgccttctgt gaagcactga gggagaccaa gcaaggccac ctggaggata tgttgctcac | 600 |
| cacccttcct gggcttcagc atgtactccc accgttgagc tgtgactacg acttgagtct | 660 |
| cccttttccg gtgtgtgagt cctgtcccct ttacaagaag ctccgcctgt cgacagatac | 720 |
| tgtggaacac tccctagaca ataaagatgg tcctgtctgc cttcaggtga agccttgcac | 780 |
| tcctgaattt tatcaaacac acttccagct ggcatatagg ttgcagtctc ggcctcgtgg | 840 |
| cctagcactg gtgttgagca atgtgcactt cactggagag aaagaactgg aatttcgctc | 900 |
| tggaggggat gtggaccaca gtactctagt cacccctcttc aagcttttgg gctatgacgt | 960 |
| ccatgttcta tgtgaccaga ctgcacagga aatgcaagag aaactgcaga attttgcaca | 1020 |
| gttacctgca caccgagtca cggactcctg catcgtggca ctcctctcgc atggtgtgga | 1080 |
| gggcgccatc tatggtgtgg atgggaaact gctccagctc aagaggtttt ttcagctctt | 1140 |
| tgacaacgcc aactgcccaa gcctacagaa caaaccaaaa atgttcttca tccaggcctg | 1200 |
| ccgtggagat gagactgatc gtgggggttga ccaacaagat ggaaagaacc acgcaggatc | 1260 |
| ccctgggtgc gaggagagtg atgccggtaa agaaaagttg ccgaagatga gactgcccac | 1320 |
| gcgctcagac atgatatgcg gctatgcctg cctcaaaggg actgccgcca tgcggaacac | 1380 |
| caaacgaggt tcctggtaca tcgaggctct tgctcaagtg tttctgagc gggcttgtga | 1440 |
| tatgcacgtg gccgacatgc tggttaaggt gaacgcactt atcaaggatc gggaaggtta | 1500 |
| tgctcctggc acagaattcc accggtgcaa ggagatgtct gaatactgca gcactctgtg | 1560 |
| ccgccacctc tacctgttcc caggacaccc tcccacatga tgtcacctcc ccatcatcca | 1620 |
| cgccaagtgg aagccactgg accacaggag gtgtgataga gcctttgatc ttcaggatgc | 1680 |
| acggtttctg ttctgccccc tcagggatgt gggaatctcc cagacttgtt tcctgtgccc | 1740 |
| atcatctctg cctttgagtg tgggactcca ggccagctcc ttttctgtga agccctttgc | 1800 |
| ctgtagagcc agccttggtt ggacctattg ccaggaatgt tcagctgca gttgaagagc | 1860 |
| ctgacaagtg aagttgtaaa cacagtgtgg ttatggggga agggcatata aattcccccat | 1920 |
| atttgtgttc agttccagct tttgtagatg gcactttagt gattgctttt attacattag | 1980 |

```
ttaagatgtc tgagagacca tctcctatct tttatttcat tcatatcctc cgcccttttt    2040
gtcctagagt gagagtttgg aaggtgtcca aatttaatgt agacattatc ttttggctct    2100
gaagaagcaa acatgactag agacgcacct tgctgcagtg tccagaagcg gcctgtgcgt    2160
tcccttcagt actgcagcgc cacccagtgg aaggacactc ttggctcgtt tgggctcaag    2220
gcaccgcagc ctgtcagcca acattgcctt gcatttgtac cttattgatc tttgcccatg    2280
gaagtctcaa agatctttcg ttggttgttt ctctgagctt tgttactgaa atgagcctcg    2340
tggggagcat cagagaaggc caggaagaat ggtgtgtttc cctagactct gtaaccacct    2400
ctctgtcttt ttccttcctg agaaacgtcc atctctctcc cttactattc ccactttcat    2460
tcaatcaacc tgcacttcat atctagattt ctagaaaagc ttcctagctt atctccctgc    2520
ttcatatctc tcccttcttt accttcattt catcctgttg gctgctgcca ccaaatctgt    2580
ctagaatcct gctttacagg atcatgtaaa tgctcaaaga tgtaatgtag ttctttgttc    2640
ctgctttctc tttcagtatt aaactctcct ttgatattat gtggctttta tttcagtgcc    2700
atacatgtta ttgttttcaa cctagaaacc tttatccctg cttatctgaa acttcccaac    2760
ttccctgttc tttaagactt tttttttttt tttttttttt tttgagacag agtctcgctc    2820
tgtcgcccag gctggagggc agtggcacga tctcagctca ctgcaagctc caactcccgg    2880
gttcacgcca ttctcctgcc tcagccttcc aagtagctgg gactacaggt gcccgccacc    2940
gtgcccggct aatttttttg tattttttagt agagacaggg tttcaccatg ttagccggga    3000
tggtcttgat ctcctgacct catgatccac ccacctcagc ctcccaaagt gttgggatta    3060
caggcgtgag ccactgcgcc cgggcaagac ctttttttaa aaaaaaaaa aaaaaaactt    3120 ccattctttc ttcctccagt ctgttctcac ataacagagt agttttggtt tttaattttt    3180
tttggttgtt tgctgttttt tgttttttaa ggtgagttct cactatgttt ctcagactgg    3240
tctcgaactc ctggcctcaa gccatcttcc cgcctcagcc tctcaaatag ctgggcttac    3300
aggcatgagc caccacacct ggccaggatt tggttgttta aatataaatc tgatcacccc    3360
cctgcttaga accctctgc tttctattac ccctcattta aaatgtaaac tcttcacctt    3420
ggtttatgag aactggttct tgccttcccc ttgaacctca ttaaatggtg atttcttgct    3480
aagctccagc ccgagtggtc tcctctcagc ttctaatttt gtgctctttc ctgccctttt    3540
cctgggcctt ctcagctctc cacccccacc actcttgact caggtggtgt ccttcttcct    3600
caagtcttga caattcccgg gcccttcagt ccctgagcag tctacttctg tgtctgtcac    3660
cacatcttgt cttttcccct cattgcattt attgcagttt atatatatgc tacttttact    3720
tgttcatttc tgtctcccct accaggctgt aaatgagggc agaaaccttg tttgttttat    3780
tcaccatcat gtaccaagtg cttggcacat agtgggcctt cattaaatgt tgttgaata    3840 aaagagggaa gaaggcaagc caaccttagc tacaatccta ccttttgata aaatgttcct    3900
tttgacaata tacacggatt attatttgta ctttgttttt ccatgtgttt tgcttttatc    3960
cactggcatt tttagctcct tgaagacata tcatgtgtga gataacttcc ttcacatctc    4020
ccatggtccc tagcaaaatg ctaggcctgt agtagtcaag gtgctcaata aatatttgtt    4080
tgggtggttt gtgagccttg ctgccaagtc ctgcctttgg gtcgacatag tatgaagta    4140 tttgagagag agaacctttc cactcccact gccaggattt tgtattgcca tcgggtgcca    4200
aataaatgct catatttatt actgaaaaaa aaaaaaaaaa aa                      4242
```

<210> SEQ ID NO 23

<211> LENGTH: 2689
<212> TYPE: DNA
<213> ORGANISM: Homo sapiens

<400> SEQUENCE: 23

| | | | | | |
|---|---|---|---|---|---|
| acatctcccg | gcggcgggcc | gcggaagcag | tgcagacgcg | gctcctagcg | gatgggtgct | 60 |
| attgtgaggc | ggttgtagaa | gagtttcgtg | agtgctcgca | gctcatacct | gtggctgtgt | 120 |
| atccgtggcc | acagctggtt | ggcgtcgcct | tgaaatccca | ggccgtgagg | agttagcgag | 180 |
| ccctgctcac | actcggcgct | ctggttttcg | gtgggtgtgc | cctgcacctg | cctcttcccc | 240 |
| cattctcatt | aataaaggta | tccatggaga | acactgaaaa | ctcagtggat | tcaaaatcca | 300 |
| ttaaaaattt | ggaaccaaag | atcatacatg | gaagcgaatc | aatggactct | ggaatatccc | 360 |
| tggacaacag | ttataaaatg | gattatcctg | agatgggttt | atgtataata | attaataata | 420 |
| agaattttca | taaaagcact | ggaatgacat | ctcggtctgg | tacagatgtc | gatgcagcaa | 480 |
| acctcaggga | acattcaga | aacttgaaat | atgaagtcag | gaataaaaat | gatcttacac | 540 |
| gtgaagaaat | tgtggaattg | atgcgtgatg | tttctaaaga | agatcacagc | aaaaggagca | 600 |
| gttttgtttg | tgtgcttctg | agccatggtg | aagaaggaat | aattttttgga | acaaatggac | 660 |
| ctgttgacct | gaaaaaaata | acaaactttt | tcagagggga | tcgttgtaga | agtctaactg | 720 |
| gaaaacccaa | acttttcatt | attcaggcct | gccgtggtac | agaactggac | tgtggcattg | 780 |
| agacagacag | tggtgttgat | gatgacatgg | cgtgtcataa | ataccagtg | gaggccgact | 840 |
| tcttgtatgc | atactccaca | gcacctggtt | attattcttg | gcgaaattca | aaggatggct | 900 |
| cctggttcat | ccagtcgctt | tgtgccatgc | tgaaacagta | tgccgacaag | cttgaattta | 960 |
| tgcacattct | tacccgggtt | aaccgaaagg | tggcaacaga | atttgagtcc | ttttcctttg | 1020 |
| acgctacttt | tcatgcaaag | aaacagattc | catgtattgt | ttccatgctc | acaaaagaac | 1080 |
| tctatttta | tcactaaaga | aatggttggt | tggtggtttt | ttttagtttg | tatgccaagt | 1140 |
| gagaagatgg | tatatttggt | actgtatttc | cctctcattt | tgacctactc | tcatgctgca | 1200 |
| gagggtactt | taagacatac | tccttccatc | aaatagaacc | actatgaagc | tacctcaaac | 1260 |
| ttccagtcag | gtagttgcaa | ttgaattaaa | ttaggaataa | ataaaaatgg | atactggtgc | 1320 |
| agtcattatg | agaggcaatg | attgttaatt | tacagctttc | atgattagca | agttacagtg | 1380 |
| atgctgtgct | atgaattttc | aagtaattgt | gaaaagtta | acattgaag | taatgaattt | 1440 |
| ttatgatatt | ccccccactt | aagactgtgt | attctagttt | tgtcaaactg | tagaaatgat | 1500 |
| gatgtggaag | aacttaggca | tctgtgggca | tggtcaaagg | ctcaaacctt | tattttagaa | 1560 |
| ttgatataca | cggatgactt | aactgcattt | ttagaccatt | tatctgggat | tatggttttg | 1620 |
| tgatgtttgt | cctgaacact | tttgttgtaa | aaaaataata | ataatgttta | atattgagaa | 1680 |
| agaaactaat | attttatgtg | agagaaagtg | tgagcaaact | aacttgactt | ttaaggctaa | 1740 |
| aacttaacat | tcatagaggg | gtggagtttt | aactgtaagg | tgctacaatg | ccctggatc | 1800 |
| taccagcata | aatatcttct | gatttgtccc | tatgcatatc | agttgagctt | catataccag | 1860 |
| caatatatct | gaagagctat | tatataaaaa | ccccaaactg | ttgattatta | gccaggtaat | 1920 |
| gtgaataaat | tctataggaa | catatgaaaa | tacaacttaa | ataataaaca | gtggaatata | 1980 |
| aggaaagcaa | taaatgaatg | ggctgagctg | cctgtaactt | gagagtagat | ggtttgagcc | 2040 |
| tgagcagaga | catgactcag | cctgttccat | gaaggcagag | ccatggacca | cgcaggaagg | 2100 |
| gcctacagcc | catttctcca | tacgcactgg | tatgtgtgga | tgatgctgcc | agggcgccat | 2160 |
| cgccaagtaa | gaaagtgaag | caaatcagaa | acttgtgaag | tggaaatgtt | ctaaaggtgg | 2220 |

-continued

| | |
|---|---|
| tgaggcaata aaaatcatag tactctttgt agcaaaattc ttaagtatgt tattttctgt | 2280 |
| tgaagtttac aatcaaagga aaatagtaat gttttatact gtttactgaa agaaaaagac | 2340 |
| ctatgagcac ataggactct agacggcatc cagccggagg ccagagctga ccctcagcc | 2400 |
| cgggaggcag gctccaggcc tcagcaggtg cggagccgtc actgcaccaa gtctcactgg | 2460 |
| ctgtcagtat gacatttcac gggagatttc ttgttgctca aaaaatgagc tcgcatttgt | 2520 |
| caatgacagt ttcttttttc ttactagacc tgtaactttt gtaaatacac atagcatgta | 2580 |
| atggtatctt aaagtgtgtt tctatgtgac aattttgtac aaatttgtta ttttccattt | 2640 |
| ttatttcaaa atatacattc aaacttaaaa ttaaaaaaaa aaaaaaaa | 2689 |

<210> SEQ ID NO 24
<211> LENGTH: 2607
<212> TYPE: DNA
<213> ORGANISM: Homo sapiens

<400> SEQUENCE: 24

| | |
|---|---|
| cccgcgcgcg ggctcaactt tgtagagcga ggggccaact ggcagagcg cgcggccagc | 60 |
| tttgcagaga gcgccctcca gggactatgc gtgcggggac acgggtcgct ttgggctctt | 120 |
| ccaccctgc ggagcgcact accccgagcc aggggcggtg caagcccgc ccggccctac | 180 |
| ccagggcggt cctccctcc gcagcgccga gactttagt ttcgctttcg ctaaaggggc | 240 |
| cccagaccct tgctgcggag cgacggagag agactgtgcc agtcccagcc gccctaccgc | 300 |
| cgtgggaacg atgcagatg atcagggctg tattgaagag cagggggttg aggattcagc | 360 |
| aaatgaagat tcagtggatg ctaagccaga ccggtcctcg tttgtaccgt ccctcttcag | 420 |
| taagaagaag aaaaatgtca ccatgcgatc catcaagacc acccgggacc gagtgcctac | 480 |
| atatcagtac aacatgaatt tgaaaagct gggcaaatgc atcataataa acaacaagaa | 540 |
| ctttgataaa gtgacaggta tgggcgttcg aaacggaaca gacaaagatg ccgaggcgct | 600 |
| cttcaagtgc ttccgaagcc tgggttttga cgtgattgtc tataatgact gctcttgtgc | 660 |
| caagatgcaa gatctgctta aaaaagcttc tgaagaggac catacaaatg ccgcctgctt | 720 |
| cgcctgcatc ctcttaagcc atggagaaga aaatgtaatt tatgggaaag atggtgtcac | 780 |
| accaataaag gatttgacag cccactttag gggggataga tgcaaaaccc ttttagagaa | 840 |
| acccaaactc ttcttcattc aggcttgccg agggaccgag cttgatgatg catccaggc | 900 |
| cgactcgggg cccatcaatg acacagatgc taatcctcga tacaagatcc cagtggaagc | 960 |
| tgacttcctc ttcgcctatt ccacggttcc aggctattac tcgtggagga gcccaggaag | 1020 |
| aggctcctgg tttgtgcaag ccctctgctc catcctggag gagcacggaa aagacctgga | 1080 |
| aatcatgcag atcctcacca gggtgaatga cagagttgcc aggcactttg agtctcagtc | 1140 |
| tgatgaccca cacttccatg agaagaagca gatccctgt gtggtctcca tgctcaccaa | 1200 |
| ggaactctac ttcagtcaat agccatatca ggggtacatt ctagctgaga agcaatgggt | 1260 |
| cactcattaa tgaatcacat ttttttatgc tcttgaaata ttcagaaatt ctccaggatt | 1320 |
| ttaatttcag gaaatgtat tgattcaaca gggaagaaac tttctggtgc tgtcttttgt | 1380 |
| tctctgaatt ttcagagact ttttttataa tgttattcat ttggtgactg tgtaactttc | 1440 |
| tcttaagatt aattttctct ttgtatgtct gttaccttgt taatagactt aatacatgca | 1500 |
| acagaagtga cttctggaga aagctcatgg ctgtgtccac tgcaattggt ggtaacagtg | 1560 |
| gtagagtcat gtttgcactt ggcaaaaaga atcccaatgt ttgacaaaac acagccaagg | 1620 |

```
ggatatttac tgctctttat tgcagaatgt gggtattgag tgtgatttga atgattttc      1680 attggcttag ggcagatttt catgcaaaag ttctcatatg agttagagga gaaaaagctt      1740
aatgattctg atatgtatcc atcaggatcc agtctggaaa acagaaacca ttctaggtgt      1800
ttcaacagag ggagtttaat acaggaaatt gacttacata gatgataaaa gagaagccaa      1860
acagcaagaa gctgttacca cacccagggc tatgaggata atgggaagag gtttggtttc      1920
ctgtgtccag tagtgggatc atccagagga gctggaacca tggtgggggc tgcctagtgg      1980
gagttaggac caccaatgga ttgtggaaaa tggagccatg acaagaacaa agccactgac      2040
tgagatggga tgagctgaga cagataagag aataccttgg tctcacctat cctgccctca      2100
catcttccac cagcacctta ctgcccaggc ctatctggaa gccacctcac caaggacctt      2160
ggaagagcaa gggacagtga ggcaggagaa gaacaagaaa tggatgtaag cctggcccat      2220
aatgtgaaca taagtaatca ctaatgctca acaatttatc cattcaatca tttattcatt      2280
gggttgtcag atagtctatg tatgtgtaaa acaatctgtt ttggctttat gtgcaaaatc      2340
tgttatagct ttaaaatata tctggaactt tttagattat ccaagccttt attttgagta      2400
aatatttgtt acttttagtt ctataagtga ggaagagttt atggcaaaga tttttggcac      2460
tttgttttca agatggtgtt atcttttgaa ttcttgataa atgactgttt ttttctgcct      2520
aatagtaact ggttaaaaaa caaatgttca tatttattga ttaaaaatgt ggttgcttaa      2580
ttcctaacca gaaaaaaaaa aaaaaaa                                          2607
```

<210> SEQ ID NO 25
<211> LENGTH: 496
<212> TYPE: PRT
<213> ORGANISM: Homo sapiens

<400> SEQUENCE: 25

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Phe His Phe Cys Arg Met Ser Trp Ala Glu
            100                 105                 110

Ala Asn Ser Gln Cys Gln Thr Gln Ser Val Pro Phe Trp Arg Arg Val
        115                 120                 125

Asp His Leu Leu Ile Arg Val Met Leu Tyr Gln Ile Ser Glu Glu Val
    130                 135                 140

Ser Arg Ser Glu Leu Arg Ser Phe Lys Phe Leu Leu Gln Glu Glu Ile
145                 150                 155                 160

Ser Lys Cys Lys Leu Asp Asp Asp Met Asn Leu Leu Asp Ile Phe Ile
                165                 170                 175

Glu Met Glu Lys Arg Val Ile Leu Gly Glu Gly Lys Leu Asp Ile Leu
            180                 185                 190

Lys Arg Val Cys Ala Gln Ile Asn Lys Ser Leu Leu Lys Ile Ile Asn
```

195                 200                 205
Asp Tyr Glu Glu Phe Ser Lys Gly Glu Glu Leu Cys Gly Val Met Thr
210                 215                 220

Ile Ser Asp Ser Pro Arg Glu Gln Asp Ser Glu Ser Gln Thr Leu Asp
225                 230                 235                 240

Lys Val Tyr Gln Met Lys Ser Lys Pro Arg Gly Tyr Cys Leu Ile Ile
            245                 250                 255

Asn Asn His Asn Phe Ala Lys Ala Arg Glu Lys Val Pro Lys Leu His
            260                 265                 270

Ser Ile Arg Asp Arg Asn Gly Thr His Leu Asp Ala Gly Ala Leu Thr
            275                 280                 285

Thr Thr Phe Glu Glu Leu His Phe Glu Ile Lys Pro His His Asp Cys
290                 295                 300

Thr Val Glu Gln Ile Tyr Glu Ile Leu Lys Ile Tyr Gln Leu Met Asp
305                 310                 315                 320

His Ser Asn Met Asp Cys Phe Ile Cys Cys Ile Leu Ser His Gly Asp
            325                 330                 335

Lys Gly Ile Ile Tyr Gly Thr Asp Gly Gln Glu Ala Pro Ile Tyr Glu
            340                 345                 350

Leu Thr Ser Gln Phe Thr Gly Leu Lys Cys Pro Ser Leu Ala Gly Lys
            355                 360                 365

Pro Lys Val Phe Phe Ile Gln Ala Cys Gln Gly Asp Asn Tyr Gln Lys
            370                 375                 380

Gly Ile Pro Val Glu Thr Asp Ser Glu Glu Gln Pro Tyr Leu Glu Met
385                 390                 395                 400

Asp Leu Ser Ser Pro Gln Thr Arg Tyr Ile Pro Asp Glu Ala Asp Phe
            405                 410                 415

Leu Leu Gly Met Ala Thr Val Asn Asn Cys Val Ser Tyr Arg Asn Pro
            420                 425                 430

Ala Glu Gly Thr Trp Tyr Ile Gln Ser Leu Cys Gln Ser Leu Arg Glu
            435                 440                 445

Arg Cys Pro Arg Gly Asp Asp Ile Leu Thr Ile Leu Thr Glu Val Asn
450                 455                 460

Tyr Glu Val Ser Asn Lys Asp Lys Lys Asn Met Gly Lys Gln Met
465                 470                 475                 480

Pro Gln Pro Thr Phe Thr Leu Arg Lys Lys Leu Val Phe Pro Ser Asp
            485                 490                 495

<210> SEQ ID NO 26
<211> LENGTH: 416
<212> TYPE: PRT
<213> ORGANISM: Homo sapiens

<400> SEQUENCE: 26

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Ser
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

-continued

```
Gly Gln Asp Met Leu Ala Ser Phe Leu Arg Thr Asn Arg Gln Ala Ala
            85                  90                  95
Lys Leu Ser Lys Pro Thr Leu Glu Asn Leu Thr Pro Val Val Leu Arg
            100                 105                 110
Pro Glu Ile Arg Lys Pro Glu Val Leu Arg Pro Glu Thr Pro Arg Pro
            115                 120                 125
Val Asp Ile Gly Ser Gly Gly Phe Gly Asp Val Gly Ala Leu Glu Ser
            130                 135                 140
Leu Arg Gly Asn Ala Asp Leu Ala Tyr Ile Leu Ser Met Glu Pro Cys
145                 150                 155                 160
Gly His Cys Leu Ile Ile Asn Asn Val Asn Phe Cys Arg Glu Ser Gly
                165                 170                 175
Leu Arg Thr Arg Thr Gly Ser Asn Ile Asp Cys Glu Lys Leu Arg Arg
                180                 185                 190
Arg Phe Ser Ser Pro His Phe Met Val Glu Val Lys Gly Asp Leu Thr
            195                 200                 205
Ala Lys Lys Met Val Leu Ala Leu Leu Glu Leu Ala Gln Gln Asp His
            210                 215                 220
Gly Ala Leu Asp Cys Cys Val Val Val Ile Leu Ser His Gly Cys Gln
225                 230                 235                 240
Ala Ser His Leu Gln Phe Pro Gly Ala Val Tyr Gly Thr Asp Gly Cys
                245                 250                 255
Pro Val Ser Val Glu Lys Ile Val Asn Ile Phe Asn Gly Thr Ser Cys
                260                 265                 270
Pro Ser Leu Gly Gly Lys Pro Lys Leu Phe Phe Ile Gln Ala Cys Gly
            275                 280                 285
Gly Glu Gln Lys Asp His Gly Phe Glu Val Ala Ser Thr Ser Pro Glu
            290                 295                 300
Asp Glu Ser Pro Gly Ser Asn Pro Glu Pro Asp Ala Thr Pro Phe Gln
305                 310                 315                 320
Glu Gly Leu Arg Thr Phe Asp Gln Leu Asp Ala Ile Ser Ser Leu Pro
                325                 330                 335
Thr Pro Ser Asp Ile Phe Val Ser Tyr Ser Thr Phe Pro Gly Phe Val
                340                 345                 350
Ser Trp Arg Asp Pro Lys Ser Gly Ser Trp Tyr Val Glu Thr Leu Asp
            355                 360                 365
Asp Ile Phe Glu Gln Trp Ala His Ser Glu Asp Leu Gln Ser Leu Leu
            370                 375                 380
Leu Arg Val Ala Asn Ala Val Ser Val Lys Gly Ile Tyr Lys Gln Met
385                 390                 395                 400
Pro Gly Cys Phe Asn Phe Leu Arg Lys Lys Leu Phe Phe Lys Thr Ser
                405                 410                 415
```

METHOD FOR PREDICTING CANCER SENSITIVITY

PRIORITY

This application is a continuation of U.S. patent application Ser. No. 14/909,373, filed on Feb. 1, 2016, now U.S. Pat. No. 10,732,182, which is the National Phase application of PCT/US2014/049420, filed Aug. 1, 2014, and claims the benefit of U.S. Provisional Application No. 61/861,009 filed Aug. 1, 2013, each which is hereby incorporated by reference herein in its entirety. The contents of the text file submitted electronically herewith are incorporated herein by reference in their entirety: A computer readable format copy of the Sequence Listing (filename: EUTR-014_01WO_Seqlist_ST25.txt, date recorded: Feb. 1, 2016; file size: 128 kilobytes).

FIELD OF THE INVENTION

The present disclosure relates to methods that are useful in evaluating tumors in human samples.

BACKGROUND

The use of predictive and prognostic biomarkers paired with targeted cancer therapies may hold the key to reducing drug development time, improving drug efficacy, and guiding clinical decision making. While there are advances in cancer treatment, chemotherapy remains largely inefficient and ineffective. One reason for the generally poor performance of chemotherapy is that the selected treatment is often not closely matched to the individual patient's disease. A personalized medicine approach that couples precision diagnostics with therapeutics, especially targeted therapeutics, is considered a highly promising method for enhancement of the effectiveness of current and future drugs. Biomarkers can facilitate the development and use of such targeted therapeutics as well as standard of care therapies.

To date there are only a handful of biomarkers that have added value to clinical oncology practice. In part this is because perceived markers often are correlative but not causal to drug mechanism. Even when the "biomarker" biology does line up with the pharmacology of the companion therapy there is still significant challenge to predicting how a drug will work in a patient. Beyond this, the path to clinical development requires the participation of physician-scientists who see the value of the test and believe it can bring benefit to their patients.

Chemotherapy used in the treatment of cancers can induce apoptosis of the tumor cells. Apoptosis is a process of programmed cell death mediated by a number of signaling pathways that converge at the mitochondria and is effected by caspases, a group of cytosolic proteins. These proteins are activated through a series of biochemical events and the terminal caspase activating event can be blocked by proteins called the inhibitors of apoptosis (IAPs) which can prevent apoptosis and block drug response in cancer patients. Inhibitor of apoptosis proteins (IAPs) suppress apoptosis through binding and inhibiting active caspases-3, -7 and -9 via its baculoviral IAP repeat (BIR) domains. Caspase inhibition by IAPs can be negatively regulated by a mitochondrial protein second mitochondrial-derived activator of caspase (SMAC). SMAC physically interacts with multiple IAPs and relieves their inhibitory effect on caspases-3, -7 and -9. A new class of treatment that mimics the function of the protein SMAC, perturbs the IAP function and activates the otherwise blocked caspase, thereby allowing apoptosis to be induced in a cell.

Further, apoptosis can be regulated by the Bcl-2 proteins, a group of mitochondrial proteins. The response to the Bcl-2 family members in a cell is in part regulated by dimerization domains within this family. More specifically, pro-apoptotic and anti-apoptotic Bcl-2 proteins form heterodimers with their cognate regulating Bcl-2 proteins (i.e., the BH3-only Bcl-2 proteins), thereby executing cell death or survival signals. For example, the ability of Bcl-2 to inhibit apoptosis is blocked by the formation of a heterodimer with Bax (Yang and Korsmeyer, 1996).

Essentially all effective cancer drugs induce apoptosis in target cancer cells. However, different cancer cells respond to an apoptosis-inducing drug in different manners. This can be due to the presence of different heterodimers between the caspases and the IAPs or the Bcl-2 heterodimers with their cognates. Determining the presence of these heterodimers in a cancer patient can then help in assessing that patient's responsiveness to an apoptosis-inducing cancer drug.

SUMMARY OF THE INVENTION

Here we provide methods for detecting the presence of a heterodimer complex that will provide a predictive tool to identify patients likely to respond to drugs that perturb heterodimer binding and induce apoptosis in a cancer cell. In one aspect of the invention, caspase-IAP heterodimers are detected. In a further aspect of the invention, Bcl-2 heterodimers are detected. The presence or absence of a particular heterodimer can be correlated to a patient's responsiveness to a particular treatment, thereby guiding the treatment regimen administered to the patient.

In one aspect, the invention provides a method for detecting a heterodimer in a patient sample, comprising: a) isolating a cancer cell or specimen from said patient; b) contacting said cancer cell or specimen with one or more antibodies that specifically bind to the heterodimer; c) detecting a signal that indicates binding of the antibody to the heterodimer; and d) determining the presence of the heterodimer based on the intensity of the signal.

Another aspect of this invention is a method for detecting the presence of a heterodimer of the Bcl-2 family using any of the antibodies described above. This method includes (i) providing a tissue sample suspected of having a heterodimer of the Bcl-2 family, (ii) contacting the sample with the antibody, (iii) detecting a signal indicative of binding of the antibody to the heterodimer, and (iv) determining the presence of the heterodimer in the sample based on the intensity of the signal. Examples of the heterodimer include Bim/Mcl-1 and Bim/Bcl-2. The tissue sample examined in this method can be a peripheral blood sample, a lymph-node sample, a bone marrow sample, or an organ tissue sample. Preferably, the specimen is a mitochondrial fraction.

In one aspect, the invention provides a method for determining a cancer treatment for a patient, comprising: a) isolating a cancer cell or specimen from said patient; b) contacting said cancer cell or specimen with one or more antibodies that specifically bind to a heterodimer; c) detecting a signal that indicates binding of the antibody to the heterodimer; d) determining the presence of the heterodimer based on the intensity of the signal; e) determining a correlation between the antibody binding to a heterodimer said cancer cell or specimen and the sensitivity of said cell or specimen to said treatment; and f) classifying the patient for likelihood of clinical response to one or more cancer treatments, wherein the presence of a heterodimer correlates with treatment efficacy.

In one aspect, the invention provides a method for predicting cancer sensitivity to treatment, comprising: a) isolating a cancer cell or specimen from said patient; b) contacting said cancer cell or specimen with one or more antibodies that specifically bind to a heterodimer; c) detecting a signal that indicates binding of the antibody to the heterodimer; d) determining the presence of the heterodimer based on the intensity of the signal; e) determining a correlation between the antibody binding to a heterodimer said cancer cell or specimen and the sensitivity of said cell or specimen to said treatment; and f) classifying the patient for likelihood of clinical response to one or more cancer treatments, wherein the presence of a heterodimer correlates with treatment efficacy.

In one embodiment, the heterodimer comprises a caspase and an inhibitor of apoptosis protein (IAP). In another embodiment, the heterodimer comprises an IAP and TRAF-2. In another embodiment, the caspase is selected from the group consisting of caspase 2, caspase 3, caspase 5, caspase 7, caspase 8, and caspase 9. In a further embodiment, the IAP is selected from the group of XIAP, IAP-1, cIAP-2, nIAP, and survivin.

In one embodiment, the heterodimer comprises different members of the Bcl-2 family. In another embodiment, the heterodimer of Bcl-2 family contains a first member of the Bcl-2 family selected from the group consisting of Bim, Bid, Bad, Puma, Noxa, Bak, Hrk, Bax, Bmf, and Mule, and a second member of the Bcl-2 family selected from the group consisting of Mcl-1, Bcl-2, Bcl-XL, Bfl-1, and Bcl-w. In another embodiment, the first member of the Bcl-2 family is Bim and the second member of the Bcl-2 family is Mcl-1, Bcl-XL, or Bcl-2.

In one embodiment, the heterodimer is an anti-apoptotic heterodimer and its presence indicates that the patient is sensitive to the drug. In another embodiment, the heterodimer is a pro-apoptotic heterodimer and its presence indicates that the patient is responsive to the drug.

In one embodiment of the invention, the cancer is a hematologic cancer. In another embodiment, the hematologic cancer is selected from acute myelogenous leukemia (AML), multiple myeloma, follicular lymphoma, acute lymphoblastic leukemia (ALL), chronic lymphocytic leukemia, and non-Hodgkin's lymphoma.

In one embodiment, the cancer is a solid tumor cancer. In a further embodiment, the solid tumor cancer is selected from non-small lung cell carcinoma, ovarian cancer, and melanoma.

In one embodiment, the cancer treatment is one or more of anti-cancer drugs, chemotherapy, antagonist of an anti-apoptotic protein, surgery, adjuvant therapy, and neoadjuvant therapy. In a further embodiment, the cancer treatment is one or more of a SMAC mimetic, BH3 mimetic, proteasome inhibitor, histone deacetylase inhibitor, glucocorticoid, steroid, monoclonal antibody, antibody-drug conjugate, or thalidomide derivative. In one embodiment, the treatment blocks formation of the particular heterodimer detected. In one embodiment, the treatment perturbs formation of the particular heterodimer detected.

In one embodiment, the specimen is a biopsy selected from a tissue sample, frozen tumor tissue specimen, cultured cells, circulating tumor cells, and a formalin-fixed paraffin-embedded tumor tissue specimen. In a further embodiment, the tissue sample is a peripheral blood sample, a lymph-node sample, a bone marrow sample, or an organ tissue sample.

In one embodiment, the sample is a mitochondrial fraction. In a further embodiment, the specimen is a human tumor-derived cell line. In another embodiment, the specimen is a cancer stem cell. In one embodiment, the specimen is derived from the biopsy of a non-solid tumor. In another embodiment, the specimen is derived from the biopsy of a patient with multiple myeloma, acute myelogenous leukemia, acute lymphocytic leukemia, chronic lymphogenous leukemia, mantle cell lymphoma, diffuse large B-cell lymphoma, and non-Hodgkin's lymphoma. In a further embodiment, the specimen is derived from a circulating tumor cell. In another embodiment, the specimen is derived from the biopsy of a solid tumor cancer. In a further embodiment, the specimen is derived from the biopsy of a patient with non-small lung cell carcinoma, ovarian cancer, and melanoma.

In one embodiment, the method further comprises determining one or more clinical factors of the patient. In another embodiment, the clinical factor is one or more of age, cytogenetic status, performance, histological subclass, gender, and disease stage.

In one embodiment, the method further comprises predicting a clinical response in the patient.

In another aspect, the invention provides an isolated antibody that specifically binds to the heterodimer. In one embodiment, the heterodimer comprises a caspase and an inhibitor of apoptosis protein (IAP). The caspase family proteins are found in inactive and active forms. In some cases IAP proteins bind to the inactive caspase (i.e., an xIAP inactive caspase 9 heterodimer). In other cases IAP proteins bind to and inactivate active caspases, (i.e., a caspase 7 and cIAP-1 heterodimer). In another embodiment, the heterodimer comprises an IAP and TRAF-2. In another embodiment, the caspase is selected from the group consisting of is selected from the group consisting of caspase 2, caspase 3, caspase 5, caspase 7, caspase 8, and caspase 9. In a further embodiment, the IAP is selected from the group of XIAP, IAP-1, cIAP-2, nIAP, and survivin. In one embodiment, the heterodimer comprises different members of the Bcl-2 family. In another embodiment, the heterodimer of Bcl-2 family contains a first member of the Bcl-2 family selected from the group consisting of Bim, Bid, Bad, Puma, Noxa, Bak, Hrk, Bax, Bmf, and Mule, and a second member of the Bcl-2 family selected from the group consisting of Mcl-1, Bcl-2, Bcl-XL, Bfl-1, and Bcl-w. In another embodiment, the first member of the Bcl-2 family is Bim and the second member of the Bcl-2 family is Mcl-1, Bcl-XL, or Bcl-2. In one embodiment, the heterodimer is an anti-apoptotic heterodimer and its presence indicates that the patient is sensitive to the drug. In another embodiment, the heterodimer is a pro-apoptotic heterodimer and its presence indicates that the patient is responsive to the drug.

The details of one or more examples of the invention are set forth in the description below. Other features or advantages of the present invention will be apparent from the following drawings, detailed description of several examples, and also from the appended claims. The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE FIGURES

FIG. 11A, FIG. 11B, FIG. 11C, and FIG. 11D show the heterodimer binding affinity ranked for all 31 IgG clones tested in this ELISA assay.

DETAILED DESCRIPTION OF THE INVENTION

Figure 1:
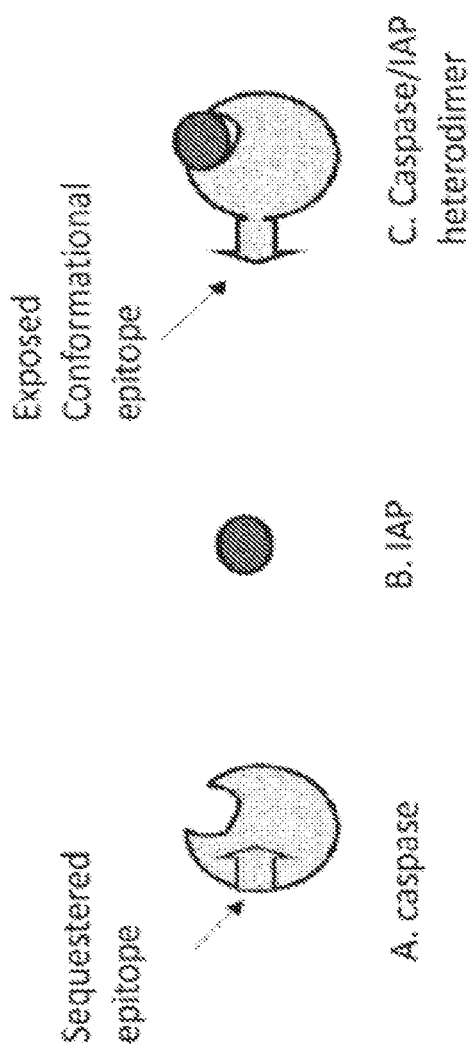
FIG. 1 is a schematic illustration depicting the conformational change of a caspase protein following binding of an IAP protein.

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

"About" includes all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±15%, ±10%, ±5%, ±4%, ±3%, ±2%, ±1%, or ±less than 1%. Importantly, all recitations of a reference value preceded by the term "about" are intended to also be a recitation of the reference value alone. Notwithstanding the preceding, in this application the term "about" has a special meaning with regard to pharmacokinetic parameters, such as area under the curve (including AUC, $AUC_t$, and $AUC_\infty$) $C_{max}$, $T_{max}$, and the like. When used in relationship to a value for a pharmacokinetic parameter, the term "about" means from 85% to 115% of the reference parameter.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

Apoptosis occurs through two main pathways: the extrinsic or cytoplasmic pathway, triggered through the Fas death receptor, a member of the tumor necrosis factor (TNF) receptor superfamily; and the intrinsic or mitochondrial pathway that when stimulated leads to the release of cytochrome-c from the mitochondria and activation of the death signal. Both pathways converge to a final common pathway involving the activation of a cascade of caspases, a family of proteases that cleave regulatory and structural molecules, culminating in the death of the cell.

Cancer cells, without wishing to be bound by theory, exhibit abnormalities, such as DNA damage, genetic instability, abnormal growth factor signaling, and abnormal or missing matrix interactions, any of which should typically induce apoptosis through the intrinsic (mitochondrial) apoptosis pathway. However, rather than respond to these apoptosis signals some cancer cells survive. Often, in doing so, these cells become highly dependent on selected blocks to chronic apoptosis signals. The formation of certain heterodimers can block the apoptotic signals.

One of the hallmarks of apoptosis is mitochondrial outer membrane permeabilization (MOMP), a process regulated by the Bcl-2 family of proteins. The activity of this family of proteins is linked to the onset of lymphoid and several solid tumor cancers and is believed in many cancers to be a key mediator of resistance to chemotherapy. Bcl-2 proteins are regulated by distinct protein-protein interactions between pro-survival (anti-apoptotic) and pro-apoptotic members. These interactions occur primarily through BH3 (Bcl-2 homology domain-3) mediated binding. Apoptosis-initiating signaling occurs for the most part upstream of the mitochondria and causes the translocation of short, BH3-only, Bcl-2 family members to the mitochondria where they either activate or sensitize MOMP. The activator BH3 only proteins, Bim and Bid, bind to and directly activate the effector, pro-apoptotic proteins Bax and Bak, and also bind to and inhibit the anti-apoptotic Bcl-2 family proteins, Bcl-2, Mcl-1, Bfl-1, Bcl-w and Bcl-xL. The sensitizer BH3 proteins, Bad, Bik, Noxa, Hrk, Bmf and Puma, bind only to the anti-apoptotic Bcl-2 family proteins, Bcl-2, Mcl-1, Bfl-1, Bcl-w and Bcl-xL, blocking their anti-apoptotic functions. Without wishing to be bound by theory, each sensitizer protein has a unique specificity profile. For example, Noxa (A and B) bind with high affinity to Mcl-1, Bad binds to Bcl-xL and Bcl-2 but only weakly to Mcl-1, and Puma binds well to all three targets. An anti-apoptotic function of these proteins is the sequestering of the activator BH3 protein Bim and Bid by binding to form heterodimers. Displacement of these activators by sensitizer peptides or treatments results in Bax/Bak-mediated apoptotic commitment. These interactions can have various outcomes, including, without limitation, homeostasis, cell death, sensitization to apoptosis, and blockade of apoptosis.

A feature of cancer cells in which apoptotic signaling is blocked is an accumulation of the BH3 only activator proteins at the mitochondrial surface, which results from these proteins being sequestered by the anti-apoptotic proteins. This accumulation and proximity to their effector target proteins accounts for increased sensitivity to antagonism of Bcl-2 family proteins in the "BH3 primed" state.

The value of Bcl-2 as a target in anti-tumor therapy has been well established. Briefly, without wishing to be bound by theory, as a result of aberrant phenotypes, cancer cells develop blocks in apoptosis pathways. These blocks make cancer cells both resistant to some therapies, and, surprisingly, make some cancer cells sensitive to other therapies. Bcl-2 promotes cell survival and normal cell growth, and is expressed in many types of cells including lymphocytes, neurons, and self-renewing cells, such as basal epithelial cells and hematopoietic progenitor cells in the bone marrow. Researchers have recognized that proteins in the Bcl-2 family regulate apoptosis and are key effectors of tumorigenesis (Reed, (2002) Nat Rev. Drug Discov. 1 (2): 111-21). It has also been reported that Mcl-1 is a target in treating NHL, CLL, and acute mylogenous leukemia (AML) (Derenne, et al. (2002) Blood, 100: 194-99; Kitada, et al. (2004) J. Nat. Canc. Inst. 96: 642-43; Petlickovski, et al. (3018) Blood 105: 4820-28).

In many cancers, anti-apoptotic Bcl-2 proteins, block the sensitivity of tumor cells to cytostatic or apoptosis inducing drugs, and these proteins have become targets for anti-tumor therapy. BH3 mimetic compounds comprise a recently described class of small molecules that inhibits Bcl-2 family proteins are the (reviewed in Bajwa, et al. (2013) Expert Opin Ther Pat. 2012 January; 22 (1): 37-55) These compounds function by inhibiting BH3 mediated protein/protein interactions among the Bcl-2 family proteins. Several studies have described BH3 mimetic small molecules that function as Bcl-2 inhibitors by blocking BH3 binding (reviewed in Billard, (2013) Mol Cancer Ther. 12 (9):1691-700). Compounds with BH3 mimic function include HA-14-1 (Wang, et al. (2000) Proc. Natl. Acad. Sci. USA 97: 7124-9), Antimycin-A (Tzung, et al. (2001) Nat. Cell. Biol. 3: 183-191), BH3I-1 and BH3I-2 (Degterev, et al. (2001) Nat. Cell. Biol. 3: 173-82), and seven un-named compounds (Enyedy, et al. (2001) J. Med Chem 44: 4313-24), as well as a series of terphenyl derivatives (Kutzki, et al. (2002) J. Am. Chem. Soc. 124: 11838-9), and two new classes of molecules (Rosenberg, et al. (2004) Anal. Biochem. 328: 131-8). Compounds with selective BH3 mimic function include Bcl-2 selective activity (Ng (2014) Clin Adv Hematol Oncol. 12 (4):224-9)—as well as selective Mcl-1 activity (Richard, et al. (2013) Bioorg Med Chem. 21 (21):6642-9) and are in various stages of clinical development. More recently, a BH3 mimic compound has been tested in a mouse tumor model (Oltersdorf, et al. (2005) Nature 435: 677-81).

Regardless of the initiating event or the path taken, the common final portion of the apoptotic program involves the activation of effector caspases which cause cell death. There may be an element of cross talk between death receptor-induced apoptotic signalling and the intrinsic apoptotic program. Evidence suggests that activated caspase-8 can cleave Bid (a pro-apoptotic BH3-only Bcl-2 family member) to a truncated form, which is then able to activate the intrinsic pathway and thus amplify the apoptotic program (Luo et al. Cell. 1998; 94:481-90; Li et al. Cell. 1998; 94:491-501; Gross et al. J Biol Chem. 1999; 274:1156-63). Bid-deficient mice show some resistance to Fas-induced hepatocyte apoptosis but their lymphocytes are normal and remain sensitive to Fas-induced killing (Yin et al. Nature. 1999; 400:886-91). Thus, Bid may play a role in amplifying the death receptor signal through the intrinsic Bcl-2 apoptotic pathway in some but not all cells. Indeed, since Bid can also be cleaved by caspases other than caspase-8 (Luo et al. Cell. 1998; 94:481-90; Li et al. Cell. 1998; 94:491-501; Yin et al. Nature. 1999; 400:886-91), it may play a more general role as an amplifier in apoptosis signalling.

Caspases are the central components of the execution phase of apoptosis. Caspases may interact with members of the TNF receptor superfamily which activates the caspases to effect cell death. For example, cell death signals, such as Fas ligand and tumor necrosis factor −2 can be specifically recognized by their corresponding receptors (e.g. Fas or TNFR-1) in the plasma membrane. This binding activates the death receptors which induces oligomerization of pro-caspases on the cytosolic side of the plasma membrane and activates them. These active caspases start a cascade resulting in cell death (see Fan et al. Acta Biochimica et Biophys Sinica, 37:719-727 (2005).

The activation and inactivation of caspases are regulated by various proteins, ions and other factors, such as IAP, Bcl-2 family proteins, calpain, Ca2+, Gran B and cytokine response modifier A (Crm A). In humans, the IAP family includes cIAP1, cIAP2, XIAP (X-linked mammalian inhibitor of apoptosis protein), NAIP (neuronal apoptosis inhibitory protein), survivin and livin. All members of the family contain 1-3 N-terminal baculovirus IAP repeat (BIR) domains and one conservative C-terminal RING (really interesting new gene) domain. The BIR domains are zinc finger-like structures that can chelate zinc ions. These zinc fingers can bind to the surface of caspases so that the amino acid sequences, or linkers, between BIR domains can block the catalyzing grooves of caspases. As a result, IAPs can protect a cell from apoptosis by inhibiting the activity of caspases. The activity of IAP can be inhibited by SMAC released from mitochondria, which can recognize and bind to the caspase-binding site of the IAP, thereby inactivating the IAP, and inhibiting its effect on caspases.

While the promise for using BH3 or SMAC mimetic compounds as anti-tumor therapeutics has been recognized, to date there are no conclusive clinical reports on the efficacy of any anti-cancer drug with these modes of action. For example, while pharmacological manipulation of the Bcl-2 family proteins is a feasible approach to achieving therapeutic benefit for cancer patients, the complexity of the network of proteins that comprise this family makes this prospect difficult. Therefore, with the large unmet medical need for treating hematological malignancies, new approaches to assessing and utilizing the detailed activity of the BH3 mimetic molecules will have value in developing this class of therapeutics.

Cetain methods disclosed herein involve the coupling of an oncology therapy and unique companion diagnostic test that is used to predict likely response to treatment. This information can be used to determine the appropriateness of administering a given treatment, and to then guide alternative treatment if required.

The heterodimer detection assays described herein provide a predictive test for cancer treatments that work through the apoptosis pathway. These assays detect the presence of heterodimers that are indicative of a cell's readiness to undergo apoptosis when exposed to an apoptotic-inducing compound or treatment. For example, some, not all, cancer cells are "pre-set" to undergo drug-induced apoptosis, which is induced by exposure to certain BH3 peptides, chemotherapeutics, or SMAC mimetics. The determination of the presence or absence of Bcl-2 or caspase-IAP heterodimers allows a determination of the cell or specimen's particular chemoresistance or chemosensitivity, and provides insight into the likelihood of a cancer cell to respond to treatment.

A critical area of focus in cancer treatment is understanding, detecting, and controlling cellular function in response to drugs and other treatments. Events occurring in the cell determine the ability of the cancer cell to respond to apoptosis-inducing cancer therapy. Cells can be evaluated to determine a cell's state using antibodies that bind to heterodimers comprising Bcl-2 proteins and their cognates and/or caspases and IAPs.

Bcl-2 Heterodimers

The present invention uses the determination of a cancer cell's predisposition to undergo apoptosis to elucidate the cancer's susceptibility to a particular treatment. One way this can be done is by using antibodies that bind to Bcl-2 heterodimers which regulate apoptosis. Formation of a heterodimer induces conformational changes in both members of the heterodimer, resulting in exposure of antigenic epitopes that are sequestered in both members before dimerization. The isolated antibody of this invention specifically recognizes such an epitope and only binds to a heterodimer of the Bcl-2 family, not to either non-dimerized member.

Bcl-2 proteins, found in mitochondria, are major regulators of the commitment to programmed cell death and executioners of death/survival signals. See Reed, Natural Clinical Practice Oncology, 3:388-398 (2006), Green et al., Cancer Cell 1:19-30 (2002), and Adams et al., Cold Spring Harb. Symp. Quant. Biol. 70:469-477 (2005). There are four sub-groups of Bcl-2 proteins: (i) multi-domain anti-apoptotic Bcl-2 proteins, (ii) multi-domain pro-apoptotic Bcl-2 proteins, (iii) activator BH3-only Bcl-2 proteins, and (iv) sensitizer BH3-only Bcl-2 proteins. Table 1 below lists major human Bcl-2 proteins and their GenBank® accession numbers:

TABLE 1

| Bcl-2 Proteins | | GenBank Accession Numbers |
| --- | --- | --- |
| Multi-domain | Bcl-2 | AAH27258 (Jul. 15, 2006) |
| Anti-Apoptotic | Bcl-XL | AAH19307 (Jul. 15, 2006) |
| Bcl-2 Proteins | Mcl-1 | AAF64255 (Jul. 17, 2000) |
| | BCL-w | AAB09055 (Sep. 29, 1996) |
| | BFL-1 | Q16548 (Mar. 3, 2009) |
| Multi-domain | BAX | Q07812 (Apr. 14, 2009) |
| Pro-Apoptotic | BAK | Q16611 (Apr. 14,2009) |
| Bcl-2 Proteins | | |
| Sensitizer BH3- | BAD | CAG46757 (Jun. 29, 2004) |
| only Bcl-2 | BIK | CAG30276 (Oct. 16, 2008) |
| Proteins | NOXA | Q13794 (Mar. 3, 2009) |
| | HRK | AAC34931 (Sep. 1998) |

TABLE 1-continued

| Bcl-2 Proteins | | GenBank Accession Numbers |
|---|---|---|
| | BMF | AAH69328 (Aug. 19, 2004); AAH60783 (Jan. 27, 2004) |
| | PUMA | Q9BXH1 (Apr. 14, 2009) |
| | Mule | Q7Z6Z7 (Apr. 14, 2009) |
| Activator BH3-only Bcl-2 Proteins | BID | P55957 (Mar. 3, 2009) |
| | BIM | O43521 (Apr. 14, 2009) |

Other Bcl-2 proteins, can be identified by homologous search using the amino acid sequence of a known Bcl-2 protein as a query. Polypeptides can be identified based on homology to the BH3 domain, and polypeptides can possess at least about 50%, about 60%, about 70%, about 80%, about 90%, about 95%, about 96%, about 97%, about 98%, about 99% sequence homology to the amino acid sequences of the polypeptides disclosed in Table 1. Preferred variants are those that have conservative amino acid substitutions made at one or more predicted non-essential amino acid residues. For example, a "conservative amino acid substitution" is one in which the amino acid residue is replaced with an amino acid residue having a similar side chain. In a further embodiment, the BH3 domain peptide is an activator or a sensitizer of apoptosis. In a preferred embodiment, the BH3 domain peptide is a sensitizer.

In one embodiment, the heterodimer comprises different members of the Bcl-2 family. In another embodiment, the heterodimer of Bcl-2 family contains a first member of the Bcl-2 family selected from the group consisting of Bim, Bid, Bad, Puma, Noxa, Bak, Hrk, Bax, Bmf, and Mule, and a second member of the Bcl-2 family selected from the group consisting of Mcl-1, Bcl-2, Bcl-XL, Bfl-1, and Bcl-w. In another embodiment, the first member of the Bcl-2 family is Bim and the second member of the Bcl-2 family is Mcl-1, Bcl-XL, or Bcl-2. In one embodiment, the heterodimer comprises Bcl-XL and Bim. In another embodiment, the heterodimer comprises Bim and Mcl-1. In another embodiment, the heterodimer comprises Bim and Bcl-2. In another embodiment, the heterodimer comprises Bid and Bcl-2.

If a cell is pre-set to undergo drug-induced apoptosis (e.g. the cell is dependent on Bcl-2 polypeptide activity for survival), the antibodies of the invention can be used to identify the specific Bcl-2 proteins that are responsible for apoptotic block.

Caspase-IAP Heterodimers

The present invention also provides an isolated antibody specific to a caspase-IAP heterodimer, i.e., a naturally-occurring heterodimer formed between any one of the caspases and any one of the IAP proteins.

Caspases, or cysteine-aspartic proteases or cysteine-dependent aspartate-directed proteases are a family of cysteine proteases that play essential roles in apoptosis (programmed cell death), necrosis, and inflammation. (Alnemri E S, Emad S; et al. (1996). Cell 87 (2): 171.) The inhibitor of apoptosis (IAP) proteins, found in cytosol of cells, are regulators of the commitment to programmed cell death and execution of death/survival signals. (Eckelman and Salvese, J. Biol. Chem. 2006, 281:3254-3260). They function to inhibit the activity of caspases by binding to a caspase polypeptide and forming a heterodimer, thereby preventing the caspase from effecting apoptosis.

Table 2 below lists major human caspases and the IAP proteins xIAP, Ciap1, cIAP2 and surviven, and their GenBank® accession numbers:

TABLE 2

| Polypeptide | Accession Number |
|---|---|
| XIAP | NM_001167.3 |
| CIAP1 | NM_001166.4 |
| CIAP2 | NM_001165.4 |
| Survivin | U75285.1 |
| caspase 2 | NM_032982.3 |
| caspase 3 | NM_004346.3 |
| caspase 7 | NM_001227.4 |
| caspase 8 | AB038985.2 |
| caspase 9 | AB019205.2 |

Figure 5:
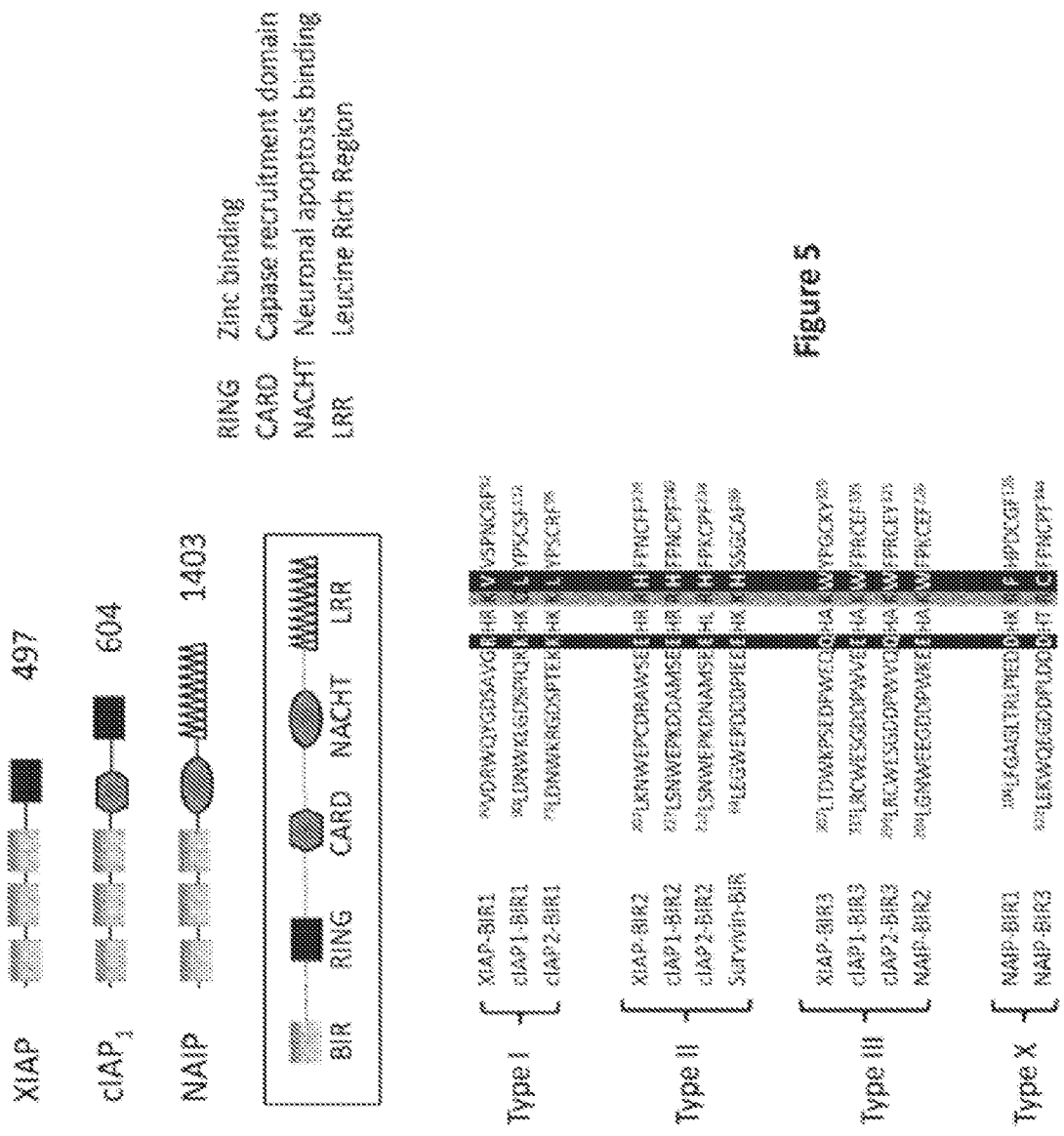
FIG. 5 is a schematic illustration depicting the structure of the IAP proteins and the sequences of the BIR domains.

IAPs comprise BIR domains which belong to the zinc-finger domain family and characteristically have a number of invariant amino acid residues, including 3 conserved cysteines and one conserved histidine, which coordinates a zinc ion. BIR domains are typically composed of 4-5 alpha helices and a three-stranded beta sheet and are approximately 70 amino acids in length. These domains bind to the caspases at the IAP binding motifs and are essential for the anti-apoptotic function of these proteins. The sequences within the BIR domains required for caspase binding have been identified. (Eckelman and Guy, J. Biol. Chem. 2006, 281:3254-3260). FIG. 5 shows the structure of the IAP proteins and the sequences of the BIR domains.

When IAPs and caspases bind to form heterodimers, conformational changes in both members of the heterodimer are induced, resulting in exposure of unique antigenic epitopes that are sequestered in both members before dimerization (FIG. 1). Antibodies that bind specifically to heterodimers of the caspase and IAP proteins, but not non-dimerized proteins, may be used to identify and measure heterodimers. In one embodiment, the disclosure provides antibodies that bind specifically to heterodimers of the caspase and IAP proteins, but not non-dimerized proteins.

Examples of the caspase-IAP heterodimer include caspase 2, 3, 5, 7, 8, or 9 binding with XIAP, IAP-1, cIAP-2, nIAP, or survivin.

Figure 3:
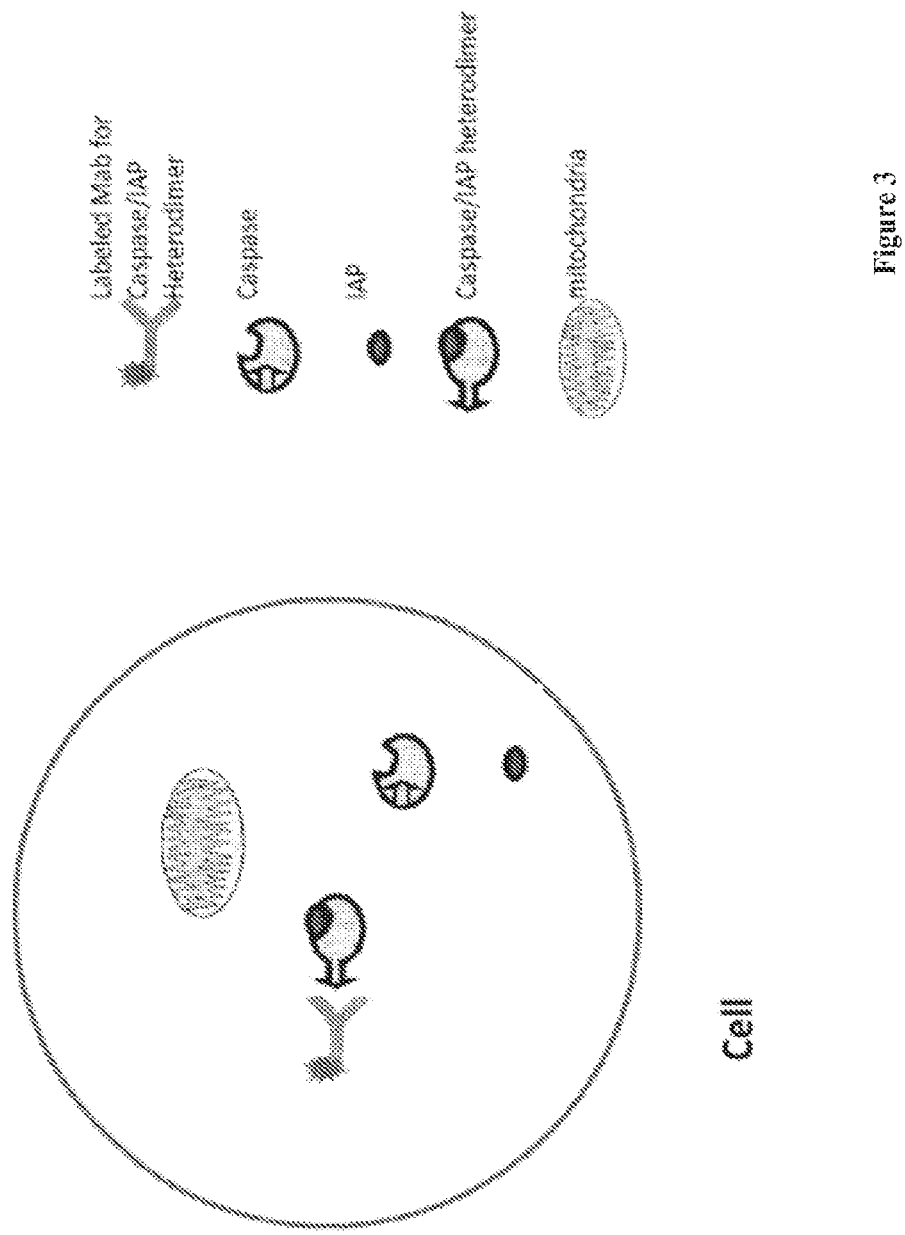
FIG. 3 is a schematic illustration depicting an immunoassay for profiling caspase-IAP heterodimers in cancer cells using the antibody of this invention, i.e., an antibody specifically recognizes caspase-IAP heterodimers.

Caspase-IAP heterodimer profiling (FIG. 3) can also be used to predict responsiveness to drugs targeting the apoptotic pathway in patients suffering from apoptosis-related diseases, e.g., autoimmune disease (see Adams et al., Cold Spring Harb Symp Quant Biol. 70:469-477; 2005) and/or cancer.

In one embodiment, the presence of a particular caspase-IAP heterodimer in a patient indicates that patient's responsiveness to a drug that blocks formation of the particular heterodimer and inhibits its function. In one embodiment, the presence of a particular caspase-IAP heterodimer in a cancer patient indicates that this patient is sensitive to a drug that interferes with formation of this anti-apoptotic IAP/caspase heterodimer.

Another aspect of this invention is a method for assessing whether a patient is sensitive or resistant to drug that works through the TNF receptor or other of the death domain family of receptors. The protein TNF receptor associated factors (TRAF1 and TRAF2) are required for TNF-alpha-mediated activation of MAPK8/JNK and NF-κB. The protein complex formed by TRAF2 and TRAF1 interacts with the IAP family members cIAP1 and cIAP2, and functions as a mediator of the anti-apoptotic signals from TNF receptors. The interaction of this protein with TRADD, a TNF receptor associated apoptotic signal transducer, ensures the recruitment of IAPs for the direct inhibition of caspase activation. Song and Donner (Biochem J. 309 (Pt 3): 825-9. 1995).

Antibodies

One aspect of this invention features an isolated antibody that specifically binds to a heterodimer of the Bcl-2 family (i.e., a Bcl-2 heterodimer). The Bcl-2 family includes both Bcl-2 proteins (monomers) and naturally-occurring heterodimers formed between two Bcl-2 proteins. The heterodimer contains a first Bcl-2 protein (e.g., Bim, Bid, Bad, Puma, Noxa, Bak, Hrk, Bax, or Mule) and a second Bcl-2 protein (e.g., Mcl-1, Bcl-2, Bcl-XL, Bfl-1 or Bcl-w). One aspect of this invention features an isolated antibody that specifically binds to a caspase-IAP heterodimer. Examples of the caspase-IAP heterodimer include caspase 2, 3, 5, 7, 8, or 9 binding with XIAP, IAP-1, cIAP-2, nIAP, or survivin.

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a F(ab)$_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are chimeric antibodies, isolated human or humanized antibodies, or functional fragments thereof. The term "isolated antibody" used herein refers to an antibody substantially free from naturally associated molecules, i.e., the naturally associated molecules constituting at most 20% by dry weight of a preparation containing the antibody.

The antibodies of the invention can be prepared by conventional methods. See, for example, Harlow and Lane, (1988) Antibodies: A Laboratory Manual, Cold Spring Harbor Laboratory, New York. In general, a heterodimer can be prepared by producing its two members separately by recombinant technology and then incubating both members under suitable conditions to allow formation of the heterodimer. To produce antibodies against the heterodimer, the heterodimer, optionally coupled to a carrier protein (e.g., KLH), can be mixed with an adjuvant, and injected into a host animal Antibodies produced in the animal can then be purified by heterodimer affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies, i.e., heterogeneous populations of antibody molecules, are present in the sera of the immunized animal.

Monoclonal antibodies, i.e., homogeneous populations of antibody molecules, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946, 778 and 4,704,692) can be adapted to produce a phage or yeast library of scFv antibodies. scFv antibodies are formed by linking the heavy and light chain fragments of the Fv region via an amino acid bridge.

Moreover, antibody fragments can be generated by known techniques. For example, such fragments include, but are not limited to, F(ab')2 fragments that can be produced by pepsin digestion of an antibody molecule, and Fab fragments that can be generated by reducing the disulfide bridges of F(ab')2 fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

The antibodies prepared by any of the methods described above are confirmed for their binding to a caspase-IAP heterodimer or a Bcl-2 heterodimer. They are further subjected to a negative selection to exclude those that also bind to either non-dimerized member of the heterodimer. For example, each of the two members, i.e., monomer A and monomer B, is labeled with a distinct fluorescent dye, i.e., dye x and dye y, respectively. Dyes x and y have different optimal emission wavelengths. The antibody is first incubated with labeled monomer A, labeled monomer B, or the A/B heterodimer (double labeled) for a suitable period and then captured by GamaBind Sepharose beads. Whether the antibody is capable of binding to either monomer or to the heterodimer can be determined based on the fluorescent signal released from the captured antibody. Antibodies that bind to the heterodimer and not to either non-dimerized member are selected.

In one embodiment, the antibodies that bind to Bcl-2 heterodimers are those disclosed in U.S. Pat. No. 8,168,755 and US 2012-0225794, the contents of which are incorporated by reference in its entirety for all purposes.

Heterodimer Binding Assay

In one aspect, the invention provides a method for detecting a heterodimer in a patient sample, comprising: a) isolating a cancer cell or specimen from said patient; b) contacting said cancer cell or specimen with one or more antibodies that specifically bind to the heterodimer; c) detecting a signal that indicates binding of the antibody to the heterodimer; and d) determining the presence of the heterodimer based on the intensity of the signal.

The assay comprises detecting the presence or absence of a Bcl-2 or caspase-IAP heterodimer in a sample, and associating the presence or absence of one or more of these heterodimers with patient classification (e.g. responder/non-responder). The heterodimers can be detected through any means commonly known in the art, including, but not limited to ELISA (as described for example in Certo et al. Cancer Cell 9 (5):351-365 (2006), immunofluorescence microscopy, immunohistochemical staining, western blotting, in cell western, immunofluorescent staining, ELISA, and fluorescent activating cell sorting (FACS), bioluminescence, or fluorescent marker detection.

Displacement of the components of the heterodimers may be assayed by first detecting whether such heterodimers are produced in the cell or sample of interest, treating with a therapeutic, compound, or treatment, and then assaying for the presence of the heterodimers in said sample. If the chosen treatment successfully disrupts the formation of heterodimers in the cell or sample, the number of heterodimers will decrease (as measured, for example, by amounts of fluorescent signal). A decrease in heterodimers in a sample after treatment indicates the cell or sample tested is sensitive to said tested treatment. Alternatively, if a decrease in heterodimers is not observed, this may be an indication that the cell or sample will not respond to said tested treatment, which may guide the decision to chose an alternative treatment for the patient from whom the sample was obtained.

Alternatively, sensitivity to a particular treatment may be measured by determining the predisposition of the cell to undergo apoptosis. In one embodiment, this can be determined by measuring the mitochondrial outer membrane permeabilization (MOMP), which increases when a cell is about to undergo apoptosis. Mitochondrial outer membrane permeabilization can be measured for example, using the potentiometric dye JC-1 or dihydrorhodamine. MOMP can be measured using standard techniques known in the art, including those described in Bogenberger et al. (Leukemia et al. (2014) which is herein incorporated by reference in its entirety). In a non-limiting example, cells are permeabilized and incubated with a mitochondrial dye (e.g. JC-1 or dihydrorhodamine 123) and BH3 peptides with dimethyl sulfoxide or carbonyl cyanide m-chlorophenyl hydrazone (CCCP) and the degree of staining is measured. In one embodiment, the predisposition of a cell to undergo apoptosis is determined by measuring the amount of cytochrome C released from the mitochondria. This can be measured using standard techniques known in the art (See for example, Current Protocols in Molecular Biology, Greene Publ. Assoc. Inc. & John Wiley & Sons, Inc., Boston, Mass., 1993).

In another embodiment, the method comprises conducting the heterodimer binding assay on a cell that comprising one or more of a cell surface marker CD33, a cell surface marker CD34, a FLT3 mutation status, a p53 mutation status, a phosphorylation state of MEK-1 kinase, and phosphorylation of serine at position 70 of Bcl-2; and correlating to efficacy in treating cancer patients with chemotherapy.

In one embodiment, the heterodimer binding assay is performed on patient samples taken before treatment begins (time "0"). In another embodiment, the heterodimer binding assay is performed on patient samples taken during the course of treatment. In a further embodiment, the heterodimer binding assay is performed on the patient's cell or sample taken before and at various time points during treatment. In another embodiment, the heterodimer binding assay is performed on the patient's cell or sample taken at various time points during treatment. In one embodiment, the decision to perform a subsequent heterodimer binding assay in a patient is made when the patient stops responding to a current course of treatment. In another embodiment, the decision to perform a subsequent heterodimer binding assay is made independently of the patient's response to treatment.

In one aspect, the heterodimer binding assay is performed in vitro. Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

Patient Evaluation and Treatment

In some embodiments, the methods described herein are useful in the evaluation of a patient, for example, for evaluating diagnosis, prognosis, and response to treatment. In various aspects, the present invention comprises evaluating a tumor or hematological cancer. In various embodiments, the evaluation may be selected from diagnosis, prognosis, and response to treatment.

Diagnosis refers to the process of attempting to determine or identify a possible disease or disorder, such as, for example, cancer. Prognosis refers to predicting a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and progression free survival, time to progression, probability of recurrence.

In various embodiments, the invention predicts the efficacy of a cancer treatment which can include one or more of anti-cancer drugs, chemotherapy, surgery, adjuvant therapy, and neoadjuvant therapy. In an exemplary embodiment, the present method will indicate a likelihood of response to a specific treatment. For example, in some embodiments, the present methods indicate a high or low likelihood of response to a pro-apoptotic agent and/or an agent that operates via apoptosis and/or an agent that operates via apoptosis driven by direct protein modulation. In an exemplary embodiment, the present method will indicate whether a patient is to receive a pro-apoptotic agent or an agent that operates via apoptosis for cancer treatment. In another exemplary embodiment, the present method will indicate whether a patient is to receive an agent that does not operate via apoptosis. In another exemplary embodiment, the present invention predicts a cancer patient's likelihood of response to chemotherapy and comprises an evaluation of the heterodimer binding, age profile and cytogenetic factors of the patient.

As used herein, the term "neoadjuvant therapy" refers to treatment given as a first step to shrink a tumor before the main treatment, which is usually surgery, is given. Examples of neoadjuvant therapy include chemotherapy, radiation therapy, and hormone therapy. In some embodiments, the present methods direct a patient's treatment to include neoadjuvant therapy. For example, a patient that is scored to be responsive to a specific treatment may receive such treatment as neoadjuvant therapy. In some embodiments, neoadjuvant therapy means chemotherapy administered to cancer patients prior to surgery. In some embodiments, neoadjuvant therapy means an agent, including those described herein, administered to cancer patients prior to surgery. Further, the present methods may direct the identity of a neoadjuvant therapy, by way of non-limiting example, as a treatment that induces and/or operates in a pro-apoptotic manner or one that does not. In one embodiment, the present methods may indicate that a patient will not be or will be less responsive to a specific treatment and therefore such a patient may not receive such treatment as neoadjuvant therapy. Accordingly, in some embodiments, the present methods provide for providing or withholding neoadjuvant therapy according to a patient's likely response. In this way, a patient's quality of life, and the cost of case, may be improved.

As used herein, the term "adjuvant therapy" refers to additional cancer treatment given after the primary treatment to lower the risk that the cancer will come back. Adjuvant therapy may include chemotherapy, radiation therapy, hormone therapy, targeted therapy, or biological therapy. In some embodiments, the present methods direct a patient's treatment to include adjuvant therapy. For example, a patient that is scored to be responsive to a specific treatment may receive such treatment as adjuvant therapy. Further, the present methods may direct the identity of an adjuvant therapy, by way of non-limiting example, as a treatment that induces and/or operates in a pro-apoptotic manner or one that does not. In one embodiment, the present methods may indicate that a patient will not be or will be less responsive to a specific treatment and therefore such a patient may not receive such treatment as adjuvant therapy. Accordingly, in some embodiments, the present methods provide for providing or withholding adjuvant therapy according to a patient's likely response. In this way, a patient's quality of life, and the cost of care, may be improved.

In various embodiments, the present methods direct a clinical decision regarding whether a patient is to receive a specific treatment. In one embodiment, the present methods are predictive of a positive response to neoadjuvant and/or adjuvant chemotherapy or non-responsiveness to neoadjuvant and/or adjuvant chemotherapy. In one embodiment, the present methods are predictive of a positive response to a pro-apoptotic agent or an agent that operates via apoptosis and/or an agent that does not operate via apoptosis or a non-responsiveness to apoptotic effector agent and/or an agent that does not operate via apoptosis. In various embodiments, the present invention directs the treatment of a cancer patient, including, for example, what type of treatment should be administered or withheld.

In some embodiments, the method comprises analysis of a patient's clinical factor. In various embodiments, the clinical factor is one or more of age, cytogenetic status, performance, histological subclass, gender, and disease stage. In another embodiment, the method further comprises a measurement of an additional biomarker selected from mutational status, single nucleotide polymorphisms, steady state protein levels, and dynamic protein levels, which can add further specificity and/or sensitivity to the test. In another embodiment, the method further comprises predicting a clinical response in the patient. In another embodiment, the clinical response is at least about 1, about 2, about 3, or about 5 year progression/event-free survival.

In one embodiment, the determination of the sensitivity or resistance of a patient's cancer cell to a particular therapeutic is used to classify the patient into a treatment or prognosis group. In some non-limiting examples, patients are classified into groups designated as cure, relapse, no complete response, complete response, refractory to initial therapy, responder, non-responder, high likelihood of response, or low likelihood of response. In further embodiments, analysis of the heterodimer binding and patient classification direct a clinical decision regarding treatment, such as, for example, switching from one therapeutic to another, a change in dose of therapeutic, or administration of a different type of treatment (e.g. surgery, radiation, allogenic bone marrow or stem cell transplant). In a further embodiment, the clinical decision is directed by the analysis of a change in cancer sensitivity, classification, and consideration of clinical factors, such as age and/or cytogenetic status. In various embodiments, a cancer treatment is administered or withheld based on the methods described herein. Exemplary treatments include surgical resection, radiation therapy (including the use of the compounds as described herein as, or in combination with, radiosensitizing agents), chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics).

In one embodiment, a comparison of the data generated in the heterodimer binding assay performed at various time points during treatment shows a change heterodimer production indicating a change in the cancer's sensitivity to a particular treatment. In one embodiment, the determination of a cancer's change in sensitivity to a particular treatment is used to re-classify the patient and to guide the course of future treatment.

Cancers

In some embodiments the invention provides a method for determining a cancer treatment and/or comprises a patient's tumor or cancer cell specimen. A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this invention are benign and malignant cancers, as well as dormant tumors or micrometastatses. Cancers which migrate from their original location and seed vital organs can eventually lead to the death of the subject through the functional deterioration of the affected organs.

In one aspect, the invention provides a method for determining a cancer treatment for a patient, comprising: a) isolating a cancer cell or specimen from said patient; b) contacting said cancer cell or specimen with one or more antibodies that specifically bind to a heterodimer; c) detecting a signal that indicates binding of the antibody to the heterodimer; d) determining the presence of the heterodimer based on the intensity of the signal; e) determining a correlation between the antibody binding to a heterodimer said cancer cell or specimen and the sensitivity of said cell or specimen to said treatment; and f) classifying the patient for likelihood of clinical response to one or more cancer treatments, wherein the presence of a heterodimer correlates with treatment efficacy.

In one aspect, the invention provides a method for predicting cancer sensitivity to treatment, comprising: a) isolating a cancer cell or specimen from said patient; b) contacting said cancer cell or specimen with one or more antibodies that specifically bind to a heterodimer; c) detecting a signal that indicates binding of the antibody to the heterodimer; d) determining the presence of the heterodimer based on the intensity of the signal; e) determining a correlation between the antibody binding to a heterodimer said cancer cell or specimen and the sensitivity of said cell or specimen to said treatment; and f) classifying the patient for likelihood of clinical response to one or more cancer treatments, wherein the presence of a heterodimer correlates with treatment efficacy.

In various embodiments, the invention is applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

The methods described herein are directed toward the prognosis of cancer, diagnosis of cancer, treatment of cancer, and/or the diagnosis, prognosis, treatment, prevention or amelioration of growth, progression, and/or metastases of malignancies and proliferative disorders associated with increased cell survival, or the inhibition of apoptosis. In some embodiments, the cancer is a hematologic cancer, including, but not limited to, acute myelogenous leukemia (AML), multiple myeloma, follicular lymphoma, acute lymphoblastic leukemia (ALL), chronic lymphocytic leukemia, and non-Hodgkin's lymphoma including, but not limited to, mantle cell lymphoma and diffuse large B-cell lymphoma. In some embodiments, the cancer is a solid tumor, including, but not limited to, non-small lung cell carcinoma, ovarian cancer, and melanoma.

In some embodiments, the invention relates to one or more of the following cancers: acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sézary syndrome, skin cancer (e.g. nonmelanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenström macroglobulinemia, and Wilms tumor.

In one embodiment, the cancer is multiple myeloma (MM). In one embodiment, the cancer is AML. AML is the second most common leukemia, with approximately 13,000 newly diagnosed cases and 9,000 deaths annually in the US. Although approved therapies exist, the prognosis of many leukemia patients is poor and the likelihood of successful treatment is low. The current standard of care for AML is induction cytosine arabinoside (ara-C) in combination with an anthracycline agent (such as, for example, daunarubicin, idarubicine or mitoxantrone). This therapeutic regimen is typically followed by administration of high dose cytarabine and/or stem cell transplantation. These treatments have improved outcome in young patients. Progress has also been made in the treatment of acute promyelocytic leukemia, where targeted therapy with all-trans retinoic acid (ATRA) or arsenic trioxide have resulted in excellent survival rates. However, patients over 60, a population which represents the vast majority of AML cases, remain a therapeutic enigma. Although 65-85% of patients initially respond to existing treatments, 65% of such responders undergo relapse, and many patients succumb to the disease. For at least this reason and because the afore-mentioned treatments may have severe side effects, the inventive predictive test can guide use of the treatment that mitigates these litigations. In some embodiments, the present invention improves the likelihood of successful treatment by matching the right patient to the right treatment. Further, there are currently no tests to predict AML patient response to treatment.

The term subject, as used herein unless otherwise defined, is a mammal, e.g., a human, mouse, rat, hamster, guinea pig, dog, cat, horse, cow, goat, sheep, pig, or non-human primate, such as a monkey, chimpanzee, or baboon. The terms "subject" and "patient" are used interchangeably.

Specimens

In some embodiments, the present invention includes the measurement of a tumor specimen, including biopsy or surgical specimen samples. In some embodiments, the biopsy is a human biopsy. In various embodiments, the biopsy is any one of a tissue sample, a frozen tumor tissue specimen, cultured cells, circulating tumor cells, and a formalin-fixed paraffin-embedded tumor tissue specimen. In some embodiments the tissue sample is a peripheral blood sample, a lymph-node sample, a bone marrow sample, or an organ tissue sample. In another embodiment, the specimen is a mitochondrial fraction.

In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about –20° C. to about –30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained.

In some embodiments, the tumor specimen may be a biopsy sample, such as cultured cells. These cells may be processed using the usual cell culture techniques that are known in the art. These cells may be circulating tumor cells.

In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue.

In certain embodiments, the tumor specimen (or biopsy) contains less than 100 mg of tissue, or in certain embodiments, contains about 50 mg of tissue or less. The tumor specimen (or biopsy) may contain from about 20 mg to about 50 mg of tissue, such as about 35 mg of tissue.

The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

In certain embodiments, the specimen is a human tumor-derived cell line. In certain embodiments, the specimen is a cancer stem cell. In other embodiments, the specimen is derived from the biopsy of a solid tumor, such as, for example, a biopsy of a colorectal, breast, prostate, lung, pancreatic, renal, or ovarian primary tumor.

In certain embodiments, the specimen is of epithelial origin. In some embodiments, the epithelial specimen is enriched by selection from a biopsy sample with an anti-epithelial cell adhesion molecule (EpCAM) or other epithelial cell binding antibody bound to solid matrix or bead.

In certain embodiments, the specimen is of mesenchymal origin. In some embodiments, the mesenchymal specimen is enriched by selection from a biopsy sample with a neural cell adhesion molecule (N-CAM) or neuropilin or other mesenchymal cell binding antibody bound to a solid matrix or bead.

In certain embodiments, the specimen is derived from the biopsy of a solid tumor. In certain embodiments, the specimen is derived from the biopsy of a non-solid tumor, such as, for example, any of the cancer described herein. In specific embodiments, the specimen is derived from the biopsy of a patient with multiple myeloma, acute myelogenous leukemia, acute lymphocytic leukemia, chronic lymphogenous leukemia, mantle cell lymphoma, diffuse large B-cell lymphoma, and non-Hodgkin's lymphoma. In a specific embodiment, the specimen is a multiple myeloma cell that is enriched by selection from a biopsy sample with an anti-CD138 antibody bound to a solid matrix or bead. In a specific embodiment, the specimen is an acute myelogenous leukemia cell that is enriched by binding to a CD45-directed antibody. In a specific embodiment, the specimen is a chronic lymphogenous leukemia or diffuse large B-cell lymphoma that is enriched by non-B cell depletion. In some embodiments, the specimen is derived from a circulating tumor cell.

Treatments

Also within the scope of this invention is a method for assessing whether a patient is sensitive or resistant to a drug that interferes with formation of a heterodimer based on the presence of that heterodimer in the patient. A cancer patient is sensitive to an apoptosis inducer that blocks formation of an anti-apoptotic heterodimer if this heterodimer is present in that patient. A neurodegenerative disease or cardiovascular disease patient, on the other hand, is responsive to an apoptosis inhibitor that blocks formation of a pro-apoptotic heterodimer if this heterodimer is present in that patient.

In exemplary embodiments, the invention selects a treatment agent. Examples of such agents include, but are not limited to, one or more of anti-cancer drugs, chemotherapy, surgery, adjuvant therapy, and neoadjuvant therapy.

In various embodiments, the invention pertains to cancer treatments including, without limitation, one or more of alkylating agents such as thiotepa and CYTOXAN cyclosphosphamide; kinesin-spindle protein stabilizing agent; proteasome inhibitor; modulator of cell cycle regulation (by way of non-limiting example, a cyclin dependent kinase inhibitor); a modulator of cellular epigenetic mechanistic (by way of non-limiting example, one or more of a histone deacetylase (HDAC) (e.g. one or more of vorinostat or entinostat), azacytidine, decitabine); a glucocorticoid; a steroid; a monoclonal antibody; an antibody-drug conjugate; a thalidomide derivative; an inhibitor of MCL1; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; an anthracycline or anthracenedione; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, a cytarabine-based chemotherapy, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chlorambucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor e.g. RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation, dacogen, velcade, and pharmaceutically acceptable salts, acids or derivatives of any of the above.

In various embodiments, cancer treatments include, without limitation, one or more BH3 mimetics. BH3 mimetics or analogs thereof, that may be used include, but are not limited to, Gossypol and its analogs (e.g. Ideker et al. Genome Res. 2008), ABT-199, ABT-737 (e.g. Petros et al. Protein Sci. 2000), ABT-263 (e.g. Letai et al. Cancer Cell 2002) and their analogues (e.g. WO2005049593, U.S. Pat. Nos. 7,767,684, 7,906,505), Obatoclax (e.g. WO2004106328, WO2005117908, U.S. Pat. No. 7,425,553), EU-5148, EU-5346, EU-4030, EU-51aa48 (Eutropics), compounds that selectively inhibit Mcl-1 (e.g. WO2008131000, WO2008130970, Richard, et al. (2013) Bioorg Med Chem. 21 (21):6642-9)), HA-14-1 (e.g. Wang, et al. (2000) Proc. Natl. Acad. Sci. USA 97: 7124-9), Antimycin-A (e.g. Tzung, et al. (2001) Nat. Cell. Biol. 3: 183-191), BH3I-1 and BH3I-2 (e.g. Degterev, et al. (2001) Nat. Cell. Biol. 3: 173-82), terphenyl derivatives (e.g. Kutzki, et al. (2002) J. Am. Chem. Soc. 124: 11838-9), and compounds with selective BH3 mimic function (e.g. Ng (2014) Clin Adv Hematol Oncol. 12 (4):224-9.

In various embodiments, cancer treatments include, without limitation, one or more SMAC mimetics or analogs thereof. SMAC mimetics mimetics or analogs thereof, that may be used include, but are not limited to, small molecule inhibitors, Smac-mimic (Li et al., Science 305: 1471-1474 (2004)), LBW242 (Petrucci et al. PLoS ONE 7 (4): e35073 (2012), TL32711 (TetraLogic Pharmaceuticals), LCL161 (Novartis), GDC-0917 (Genentech), AEG40826/HGS1029 (Aegera), AT-406 (Ascenta), and the SMAC mimetics disclosed in U.S. Pat. No. 7,807,699.

In various embodiments, the invention pertains to cancer treatments including, without limitation, those described in US Patent Publication No. US 2012-0225851 and International Patent Publication No. WO 2012/122370, the contents of which are hereby incorporated by reference in their entireties.

Clinical Factors and Additional Biomarkers

In some embodiments, the invention comprises the evaluation of clinical factors. In some embodiments, the invention comprises an evaluation of heterodimer binding and/or clinical factors to assess a patient response. In some embodiments, a clinical factor that provides patient response information in combination with a heterodimer binding study may not be linked to apoptosis. In some embodiments, a clinical factor is non-apoptosis affecting.

In one embodiment, the clinical factor is one or more of age, cytogenetic status, performance, histological subclass, gender, and disease stage.

In one embodiment, the clinical factor is age. In one embodiment, the patient age profile is classified as over about 10, or over about 20, or over about 30, or over about 40, or over about 50, or over about 60, or over about 70, or over about 80 years old.

In one embodiment, the clinical factor is cytogenetic status. In some cancers, such as Wilms tumor and retinoblastoma, for example, gene deletions or inactivations are responsible for initiating cancer progression, as chromosomal regions associated with tumor suppressors are commonly deleted or mutated. For example, deletions, inversions, and translocations are commonly detected in chromosome region 9p21 in gliomas, non-small-cell lung cancers, leukemias, and melanomas. Without wishing to be bound by theory, these chromosomal changes may inactivate the tumor suppressor cyclin-dependent kinase inhibitor 2A. Along with these deletions of specific genes, large portions of chromosomes can also be lost. For instance, chromosomes 1p and 16q are commonly lost in solid tumor cells. Gene duplications and increases in gene copy numbers can also contribute to cancer and can be detected with transcriptional analysis or copy number variation arrays. For example, the chromosomal region 12q13-q14 is amplified in many sarcomas. This chromosomal region encodes a binding protein called MDM2, which is known to bind to a tumor suppressor called p53. When MDM2 is amplified, it prevents p53 from regulating cell growth, which can result in tumor formation. Further, certain breast cancers are associated with overexpression and increases in copy number of the ERBB2 gene, which codes for human epidermal growth factor receptor 2. Also, gains in chromosomal number, such as chromosomes 1q and 3q, are also associated with increased cancer risk.

Cytogenetic status can be measured in a variety of manners known in the art. For example, FISH, traditional karyotyping, and virtual karyotyping (e.g. comparative genomic hybridization arrays, CGH and single nucleotide polymorphism arrays) may be used. For example, FISH may be used to assess chromosome rearrangement at specific loci and these phenomenon are associated with disease risk status. In some embodiments, the cytogenetic status is favorable, intermediate, or unfavorable.

In one embodiment, the clinical factor is performance. Performance status can be quantified using any system and methods for scoring a patient's performance status are known in the art. The measure is often used to determine whether a patient can receive chemotherapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry. Higher performance status (e.g., at least 80%, or at least 70% using the Karnofsky scoring system) may indicate treatment to prevent progression of the disease state, and enhance the patient's ability to accept chemotherapy and/or radiation treatment. For example, in these embodiments, the patient is ambulatory and capable of self care. In other embodiments, the evaluation is indicative of a patient with a low performance status (e.g., less than 50%, less than 30%, or less than 20% using the Karnofsky scoring system), so as to allow conventional radiotherapy and/or chemotherapy to be tolerated. In these embodiments, the patient is largely confined to bed or chair and is disabled even for self-care.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than 50% of waking hours; 3, capable of only limited self-care, confined to bed or chair more than 50% of waking hours; 4, completely disabled, cannot carry on any self-care, totally confined to bed or chair; 5, dead.

In one embodiment, the clinical factor is histological subclass. In some embodiments, histological samples of tumors are graded according to Elston & Ellis, Histopathology, 1991, 19:403-10, the contents of which are hereby incorporated by reference in their entirety.

In one embodiment, the clinical factor is gender. In one embodiment, the gender is male. In another embodiment the gender is female.

In one embodiment, the clinical factor is disease stage. By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In some embodiments, the clinical factor is the French-American-British (FAB) classification system for hematologic diseases (e.g. indicating the presence of dysmyelopoiesis and the quantification of myeloblasts and erythroblasts). In one embodiment, the FAB for acute lymphoblastic leukemias is L1-L3, or for acute myeloid leukemias is M0-M7.

In another embodiment, the method further comprises a measurement of an additional biomarker selected from mutational status, single nucleotide polymorphisms, steady state protein levels, and dynamic protein levels. In another embodiment, the method further comprises predicting a clinical response in the patient. In another embodiment, the clinical response is about 1, about 2, about 3, or about 5 year progression/event-free survival.

A variety of clinical factors have been identified, such as age profile and performance status. A number of static measurements of diagnosis have also been utilized, such as cytogenetics and molecular events including, without limitation, mutations in the genes MLL, AML/ETO, Flt3-ITD, NPM1 (NPMc+), CEBPα, IDH1, IDH2, RUNX1, ras, and WT1 and in the epigenetic modifying genes TET2 and ASXL, as well as changes in the cell signaling protein profile.

Further, in some embodiments, the any one of the following clinical factors may be useful in the methods described herein: gender; genetic risk factors; family history; personal history; race and ethnicity; features of the certain tissues; various benign conditions (e.g. non-proliferative lesions); previous chest radiation; carcinogen exposure and the like.

Further still, in some embodiments, the any one of the following clinical factors may be useful in the methods described herein: one or more of a cell surface marker CD33, a cell surface marker CD34, a FLT3 mutation status, a p53 mutation status, a phosphorylation state of MEK-1 kinase, and phosphorylation of serine at position 70 of Bcl-2.

In some embodiments, the clinical factor is expression levels of the cytokines, including, without limitation, interleukin-6. In some embodiments, interleukin-6 levels will correlate with likelihood of response in MM patients, including a poor patient prognosis or a good patient prognosis.

In another embodiment, the method comprises measuring the heterodimer binding of a cell expressing one or more of a cell surface marker CD33, a cell surface marker CD34, a FLT3 mutation status, a p53 mutation status, a phosphorylation state of MEK-1 kinase, and phosphorylation of serine at position 70 of Bcl-2; and correlating to efficacy in treating cancer patients with chemotherapy.

In still another embodiment, the cancer is AML and/or MM and the clinical factor is age profile and/or cytogenetic status; or the cancer is AML and/or MM and the cancer treatment is cytarabine or cytarabine-based chemotherapy and/or azacytidine, or the cancer treatment is cytarabine or cytarabine-based chemotherapy and/or azacytidine and the clinical factor is age profile and/or cytogenetic status, or the cancer treatment is cytarabine or cytarabine-based chemotherapy and/or azacytidine; the cancer is AML and/or MM; and the clinical factor is age profile and/or cytogenetic status.

The invention also provides kits that can simplify the evaluation of tumor or cancer cell specimens. A typical kit of the invention comprises various reagents including, for example, one or more agents to detect a BH3 peptide. A kit may also comprise one or more of reagents for detection, including those useful in various detection methods, such as, for example, antibodies. The kit can further comprise materials necessary for the evaluation, including welled plates, syringes, and the like. The kit can further comprise a label or printed instructions instructing the use of described reagents. The kit can further comprise a treatment to be tested.

Detection Methods

In various embodiments, the present methods comprise evaluating the cytogenetic status of a cell (e.g. evaluating a presence, absence, or level of a protein and/or a nucleic acid). In various embodiments, the present methods comprise evaluating a presence, absence, or level of a protein and/or a nucleic acid which can enhance the specificity and/or sensitivity of heterodimer binding. In some embodiments, the evaluating is of a marker for patient response. In some embodiments, the present methods comprise measurement using one or more of immunohistochemical staining, western blotting, in cell western, immunofluorescent staining, ELISA, and fluorescent activating cell sorting (FACS), bioluminescence, fluorescent marker detection, or any other method described herein or known in the art. The present methods may comprise contacting an antibody with a tumor specimen (e.g. biopsy or tissue or body fluid) to identify an epitope that is specific to the tissue or body fluid and that is indicative of a state of a cancer.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, NY, 1988), Harlow et al. (Using Antibodies, A Laboratory Manual, Cold Spring Harbor Laboratory, NY, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In another embodiment, the measurement comprises evaluating a presence, absence, or level of a nucleic acid. A person skilled in the art will appreciate that a number of methods can be used to detect or quantify the DNA/RNA levels of appropriate markers.

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

This invention is further illustrated by the following non-limiting examples.

EXAMPLES

Example 1: Preparation of Monoclonal Antibodies Specific to Caspase-IAP Heterodimers Genes encoding human caspase, 9, 7 and 3 minus the caspase recruitment domain are cloned and expressed as described in *Curr Protoc Protein Sci.* 2003 February; Chapter 21:Unit 21.13. *Expression, purification, and characterization of caspases.* Denault J B, Salvesen G S.)

All of the DNA constructs are introduced into BL21 *E. coli* cells. Positive transformants are cultured in a suitable medium and expression of the fusion proteins are induced with isopropyl-1-thio-β-D-galactopyranoside. The expressed fusion proteins are purified using Amersham Hitrap Glutathione column on the ACTA-FPLC (Amersham) and accurately quantified using spectrophotometry.

Peptides comprising the BIR 1 and 3 domains of xIAP and the BIR-2 domains of xIAP, cIAP1, or cIAP2, as described in table 3 are made with one aromatic amino acid residue replaced with benzol phenylalanine (Bpa) during synthesis. The Bpa modified BIR-3 domain peptides are checked for binding to caspase 3, 7 and 9 using fluorescence polarization, in this case by inhibiting the bonding of wild type peptides are labeled with FITC to caspases (Eckelman and Salvesen, *J. Biol. Chem.* 2006, 281:3254-3260).

After binding kinetics are determined at equamolar amounts in PBS and exposed to UV light to catalyze covalent attachment of the Bpa residue to the caspase protein. The mixture is stirred on ice for 12 hours to allow formation of heterodimers. The heterodimers are separated from unbound caspase proteins using a BIR 2, BIR-1 or BIR3 peptide coupled sepharose 12 column on a ACTA-FPLC, following the method described in Zue et al., Protein Science 6: 781-788 (2007).

Each of the heterodimers (1 mg) is suspended in monophosphoryl lipid A plus trehalose dicorynomycolate adjuvant. The mixtures thus formed are injected into Balb/c mice at each hind foot pad once every 3-4 days for 14 times. Three days after the final injection, spleen cells are removed from the mice and a single cell suspension is prepared in a DMEM medium supplemented with 1% penicillin-streptomycin. The spleen cells are fused with murine myeloma cells P3X63AgU.1 (ATCC® CRL 1597) using 35% polyethylene glycol and cultured in 96-well culture plates.

Hybridomas are selected in super DMEM [DMEM supplemented with 10% fetal calf serum FCS, 100 mM pyruvate, 100 U/ml insulin, 100 mM oxaloacetic acid, 2 mM glutamine, 1% nonessential amino acids, 100 U/ml penicillin, and 100 µg/ml streptomycin] containing 100 µM hypoxanthine, 0.4 µM aminopterin, and 16 µM thymidine (HAT).

Hybridoma cells are fed with 200 µl of super DMEM containing 10% FCS and antibiotics. Ten days after the fusion, supernatants of the hybridoma cultures are collected and screened for the presence of antibodies that bind to the cognate heterodimer protein and/or to either member of the heterodimer (as negative controls) in a capture ELISA as described in Certo et al., Cancer Cell., 9 (5):351-365 (2006).

Briefly, 96-well microtiter plates are coated with 50 µl (1 µg/ml) of a heterodimer or a member of the heterodimer at 4° C. overnight. The plates are then washed three times with PBS containing 0.05% TWEEN 20® (PBST) and blocked with 50 µl PBS containing 2.0% bovine serum albumin (BSA) at room temperature for 1 hour. The plates are then washed again three times with PBST. Afterwards, 100 µl of a hybridoma supernatant is added to designated wells. The plates are incubated at room temperature for 1 hour on a shaker apparatus and then washed three times with wash buffer. Next, 50 µl HRP-conjugated goat anti-mouse IgG Fc, diluted 1:1000 in assay buffer (0.5% bovine serum albumin, 0.05% % TWEEN 20™, 0.01% Thimersol in PBS), is added to each well. The plates are then incubated for 1 hour at room temperature on a shaker apparatus and washed three times with wash buffer, followed by addition of 50 µl of substrate DACO and incubation at room temperature for 10 minutes. 50 µl diethyl glycol were added to each well to stop the reaction and absorbance at 450 nm in each well is read in a microtiter plate reader.

Hybridoma cells producing antibodies that bind to a heterodimer but not to either member of the heterodimer are selected. These positive hybridoma cells are cloned twice and the specificity of the antibodies produced thereby are retested. The isotypes of the antibodies having the desired specificity are determined by conventional methods, e.g., using isotype specific goat anti-mouse Igs.

Example 2: Preparation of Polyclonal Antibodies Specific to Caspase-IAP Heterodimers New Zealand rabbits are immunized on the back and proximal limbs of the rabbits with 0.1 ml of a caspase-IAP heterodimer (50 µg/ml) prepared following the method described in Example 1. The heterodimer is pre-mixed with 50% Freund's complete adjuvant. The immunization is repeated 28th days later. On day 35, 0.5 ml of blood is obtained from each of the immunized rabbits and antibody titers in the blood samples are determined by ELISA. Anti-sera are collected from the arterial carotid of rabbits having high antibody titers.

The specificity of the antibodies in each antiserum is examined by conventional methods, e.g., the immunoprecipitation and FACS assays described in Examples 4 and 5 below.

Figure 4:
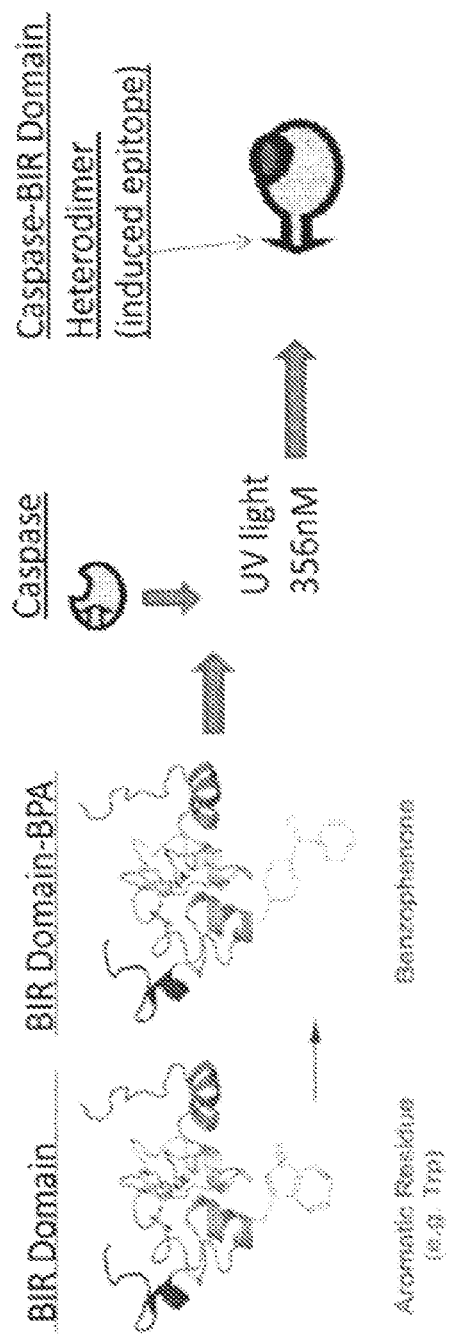
FIG. 4 is a schematic illustration showing substitution of an aromatic amino acid in the BIR domain of IAP protein and covalent binding of this peptide to the caspase to make the covalent heterodimer for antibody production.

Example 3: Screening for scFv Antibodies Specific to Caspase-IAP Heterodimers Using A Yeast scFv Library A nonimmune human scFv yeast library (using expression vector pYD1) is obtained from Pacific Northwest National Laboratories. In this library, a scFv antibody, in which the heavy and light chains are connected by a flexible polypeptide linker, is fused to the adhesion subunit of the yeast agglutinin protein Aga2p and the HA-tag. Upon expression, the scFv is located on the surface of a yeast host cell via binding of Aga2P to Aga1P, a cell surface protein. See FIG. 4. Each yeast cell typically displays $1 \times 10^5$ to $1 \times 10^6$ copies of the scFv and the surface expression of the scFv. Variations in surface expression can be measured through immunofluorescence labeling of the HA-tag flanking the scFv region.

The scFv library described above is introduced into yeast strain EBY100 (Invitrogen™) and scFv antibodies having the desired specificity are identified as follows. The EBY yeast cells are first grown overnight in 1 liter of SDCAA medium (containing 20 g dextrose, 6.7 g Difco yeast nitrogen base, 5 g Bacto casamino acids, 5.4 g Na2HPO4 and 8.56 g NaH2PO4H2O). $1 \times 10^{10}$ yeast cells from the overnight culture are precipitated by centrifugation at 2,500 g for 5 minutes and resuspended in SGCAA medium (a medium identical to SDACC except that it contains galactose instead of dextrose) to an absorbance of about 0.5-1 at 600 nm. The yeast cells are then cultured at 20° C. for 36 h to allow expression of scFv antibodies. Afterwards, the cells are collected by centrifugation at 2,500 g for 5 min. The cell pellet is washed with 25 ml PBS.

Yeast cells expressing scFv antibodies are sorted by flow cytometry. Briefly, about $1 \times 10^6$ to $1 \times 10_7$ yeast cells prepared as described above are collected via centrifugation at 14,000 g for 30 seconds, washed with 1 ml PBS buffer, and mixed with 2 µl of 10 µg/ml anti-HA phycoerythrin monoclonal antibody (SIGMA-ALDRICH™) and caspase-IAP heterodimer, in which the anti-capase antibody is labeled with FITC and the IAP antibody is labeled with Texas Red®. After being incubated at room temperature for 1 hour, the mixture is centrifuged at 12,000 g for 30 seconds to precipitate yeast cells. The cell pellet thus formed is resuspended in 500 µl 10 mM Tris (final cell density about $10^6$/ml) and subjected to cell sorting by flow cytometry as follows.

A flow cytometry protocol is pre-determined using EBY100 yeast cells mixed with the anti-HA phycoerythrin antibody as a positive control and EBY100 yeast cells mixed with the double-labeled heterodimer as a negative control. Compensation is performed to reject crosstalk between the FITC, Texas Red®, and phycoerythrin channels of the fluorescence detector. The labeled yeast cells are loaded into a FACSAria Cell-Sorter (Becton Dickinson, Mountain View, Calif.) and gated on forward- and side scatter channels. An appropriate sort gate in the FITC/Texas red/phycoerythrin positive quadrant is drawn and the top 5% triple positive yeast cells are collected in 1 ml SDCAA media. If necessary, the top 0.1% triple-positive yeast cells are collected to ensure that only cells having high affinity to caspase IAP heterodimer is sorted.

The triple-positive cells thus identified are suspended in 10 ml SDCAA and grown over night at 30° C. These cells are then subjected to two rounds of negative selection to exclude cells expressing scFv antibodies that also bind to caspase monomer or IAP monomer. More specifically, the cells are incubated with FITC-labeled caspase and Texas red-labeled IAP and following the same procedure described above, FITC and Texas Red® double negative cells are sorted. The cells thus collected are labeled with the double-labeled caspase IAP heterodimer to confirm their binding to the heterodimer.

The yeast cell thus identified are diluted and plated to allow formation of individual clones. Plasmid DNAs are isolated from these clones using a Zymoprep kit (Zymo Research, Orange, Calif.) as described in Weaver-Feldhaus et al., Protein Engineering, Design & Selection vol. 18, no. 11, pp 527-536 (2005). The scFv sequence included in each plasmid DNA is determined following the method described in Chao et al., Nature Protocols 1:755-768 (2006).

The scFv antibodies thus identified are analyzed by ELISA and FACS to confirm their specificity to caspase-IAP heterodimer. They can subject to mutagenesis to select for scFv antibodies having higher affinity and specificity to caspase IAP heterodimer.

Figure 2:
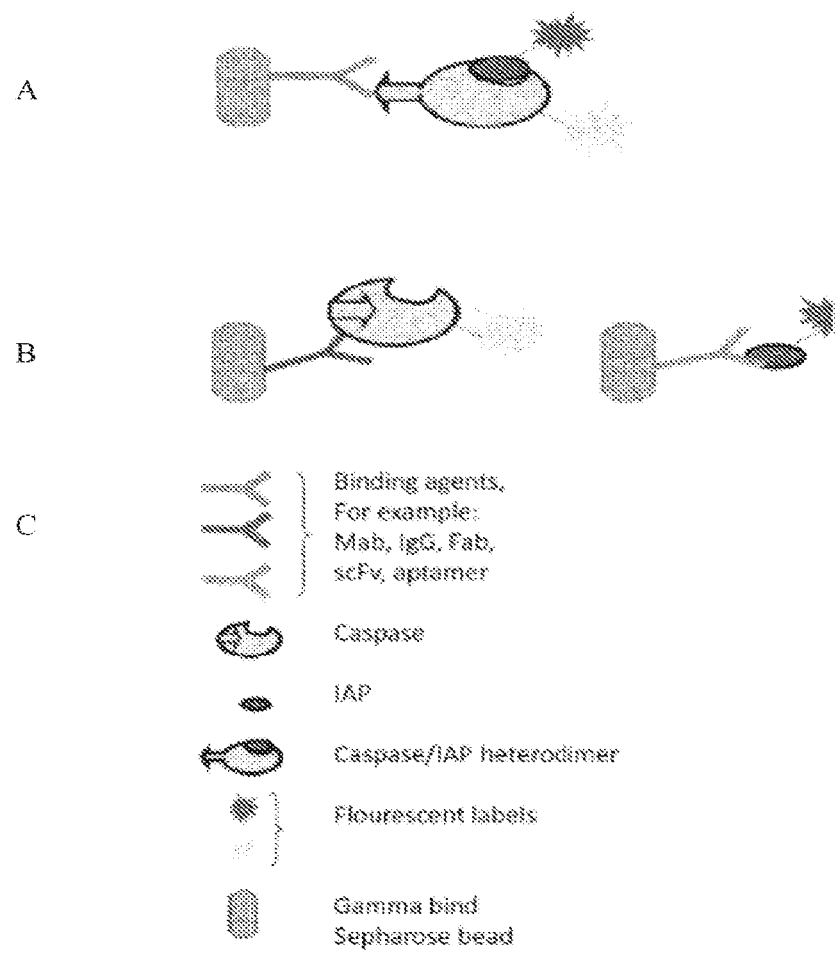
FIG. 2 is a schematic illustration depicting the process of selecting antibodies specific to caspase-IAP heterodimers via an immunoassay. Panel A: antibodies binding to a caspase-IAP heterodimer being positively selected. Panel B: antibodies binding to non-dimerized members of the heterodimer being negatively selected. Panel C: illustrate the symbols in Panels A and B.

Example 4: Select Antibodies Specific to Caspase IAP Heterodimers by Immunoprecipitation An immunoprecipitation assay, as illustrated in FIG. 2, is performed to ensure that the antibodies obtained in Example 1 above are specific to caspase IAP heterodimer. The two members of a caspase IAP heterodimer are conjugated with two fluorescent probes that have distinct emission spectra, i.e., one labeled with fluorescein isothiocyanate (FITC; which emits at 488 nm) and the other labeled with Texas red (which emits at 590 nm). The labeled members are incubated together to allow formation of the caspase IAP heterodimer, following the method described in Example 1 above. 0.1 µg of the heterodimer thus formed is incubated with 50 µL of supernatant from a hydridoma clone that produces an antibody of interest in 0.5 mL PBS containing 0.05% TWEEN 20™. The non-dimerized labeled members of the heterodimer are used as negative controls. The mixtures are incubated for 1 hour on ice to allow formation of antibody-antigen complexes and 10 µl of GammaBing-G sepharose beads (GE Healthcare™, Piscataway, N.Y.) are added to the mixture. After being incubated on ice for 30 minutes on ice with rotation, the mixtures are centrifuged at 10,000 g for 30 seconds. The pellet beads, to which the antibody-antigen complexes are attached, are washed several times and measured for optical density at 488 nm (OD488) and 590 nm (OD590). The specificity of the antibody is determined based on the values of OD488 and 590 nm OD590.

Example 5: Detecting Caspase-IAP Heterodimers in Fixed Cells

Cells care characterized for having a prevalent caspase IAP heterodimer. These cells, placed on cover slips, are fixed with 2-4% formaldehyde (Formaldehyde, 16%, methanol free) in PBS for 15 minutes at room temperature. The cell-containing cover slips are rinsed with PBS three times, 5 minutes for each. The slips are then soaked in a blocking buffer (TBST/5% normal goat serum: to 5 ml 1×TBST add 250 µl normal goat serum) for 60 minutes. After the blocking buffer is aspirated, an antibody specific to either caspase 3, 7 or 9 or cIAP1, cIAP2, xIAP heterodimer (0.1 to 15 mg/ml) is added to the slips. After being incubated at 4° C. overnight, the slips are rinsed three times with PBS, 5 minutes each time. A fluorochrome-conjugated secondary antibody, diluted in a dilution buffer, is then added. After being incubated for 1-2 hours at room temperature in dark, the slips are rinsed with PBS three times, 2 minutes each time, and subsequently treated with Prolong Gold Antifade Reagent (Invitrogen™). The slips are then sealed by painting around edges of the slips with nail polish and observed under an inverted fluorescent microscope.

Example 6: Detecting Caspase-IAP Heterodimers in Fixed Tissue Samples

Paraffin embedded and frozen thin section tissue samples from cancer patients and healthy subjects are purchased from Imgenex™. These samples are spotted on microarray chips (4 mm×4 mm spots that are 4 mm thick). The adjacent normal tissues from the same patients/healthy subjects are also spotted on the array chips.

The microarray chips mentioned above are washed in turn with xylene three times, 5 minutes each time, 100% ethanol twice, 10 minutes each time, 95% ethanol, twice, 10 minutes each time, and finally dH2O twice, 5 minutes each time. The chips are then soaked in 1 mM EDTA, pH 8.0, heated to boiling, and then kept at a sub-boiling temperature for 15 minutes.

If the tissue samples on the microarray chips are fixed with formalin, the chips are washed in turn with 100%, 95%, 80% ethanol 3 times each, 3 minutes each time, followed by two washes with dH2O, 3 minutes each. The chips are then soaked in 0.01M sodium citrate. pH 6.0 for 20 minutes.

The chips are then washed with $dH_2O$ three times, 5 minutes each time, incubated in 3% hydrogen peroxide for 10 minutes (this step is not needed for formalin fixed samples), and washed again with dH2O twice, 5 minutes each time.

Next, the chips are subjected to immunostaining using the antibodies prepared in Example 1 or an anti-caspase antibody as a control. The chips are soaked in a wash buffer for 5 minutes and then in 100-400 µl of a blocking buffer (TBST containing 5% normal goat serum) for one hour. After decanting the blocking solution, the chips are incubated with 100-400 µl of an anti-caspase/IAP-heterodimer antibody (primary antibody), diluted to 0.1 to 15 µg/ml for each chip, overnight at 4 µC. Afterwards, the chips are washed with the wash buffer three times, 5 minutes each time, and then incubated with 100-400 µl of a biotinylated goat anti-mouse Ig antibody (the secondary antibody), which is diluted in TBST following the manufacturer's protocol, for 30 minutes at room temperature. The chips are then washed with the wash buffer three times, 5 minutes each time, and incubated with 100-400 µl ABC reagent (Vectastain ABC Kit™), which is prepared following the manufacturer's instructions, for 30 minutes at room temperature. After being washed for three times with the wash buffer, the chips are incubated with 100-400 µl DAB for signal development. The chips are immersed in dH$_2$O immediately after a color has developed thereon. When necessary, the chips are counterstained with hematoxylin and DAPI following manufacturer's instructions.

The stained chips are dehydrated by incubation sequentially in 95% ethanol two times, 10 seconds each, in 100% ethanol two times, 10 seconds each, and finally in xylene two times, 10 seconds each. The chips are then mounted with cover slips and examined using Fluorescence and UV microscopy for staining patterns. The staining patterns obtained from cancer tissue samples are compared with those obtained from adjacent normal tissues.

Example 7: Antibodies that Bind Bim-BH3 Domain Peptide

Preparation of Heterodimer Immunogen

Figure 6:
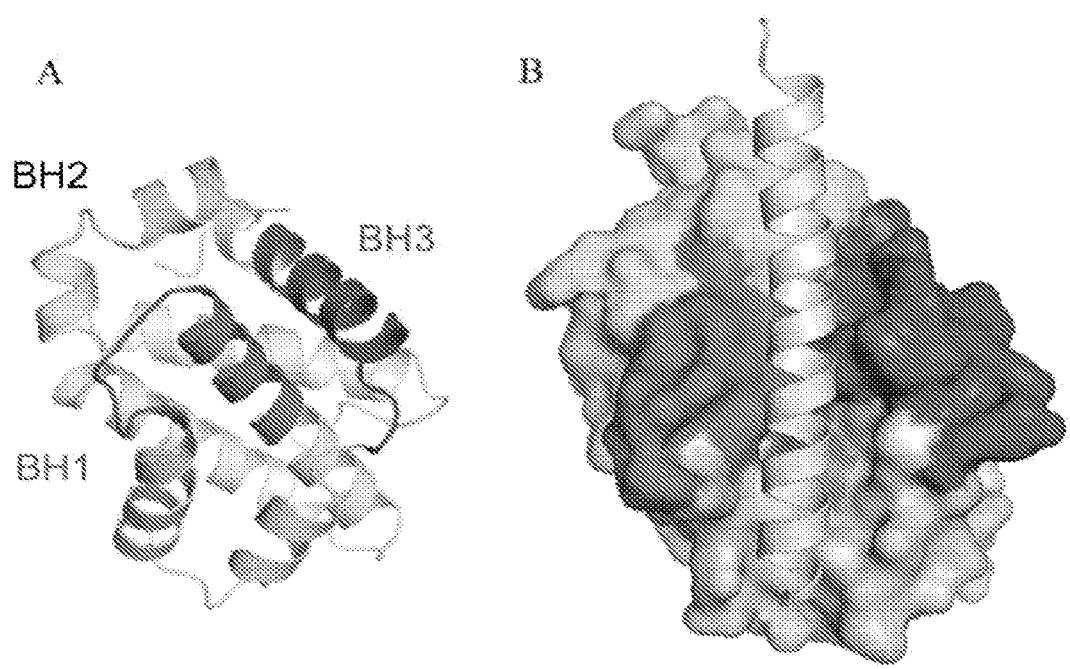
FIG. 6 shows the hydrophobic groove of BCL-XL formed by BH1-3. Panel A is a ribbon representation of BCL-XL with BH1 colored pink, BH2 colored yellow, and BH3 colored red. Panel B is a surface representation of BCL-XL bound to BIM BH3 peptide, shown in ribbon.
Figure 7:
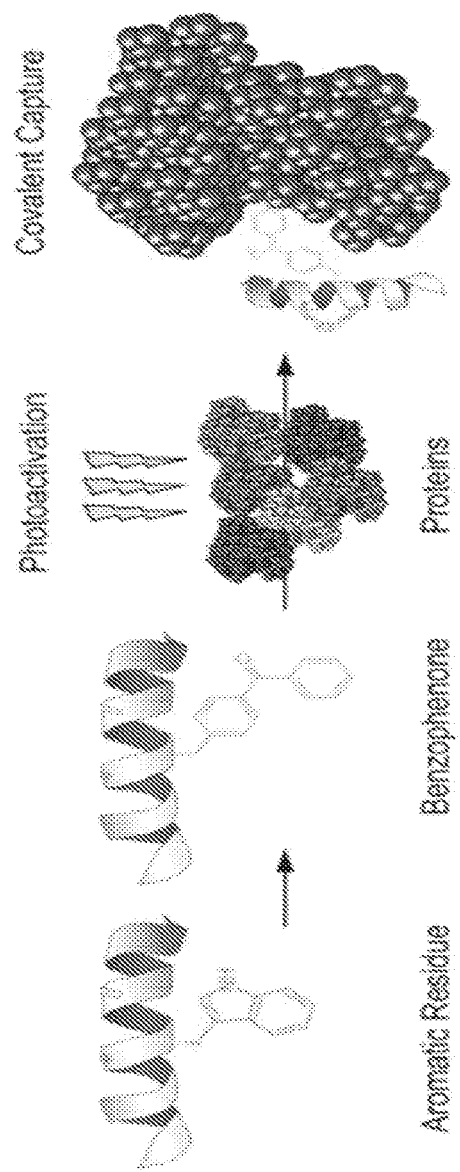
FIG. 7 shows a schematic illustration depicting the coupling of photoactivatable benzophenyl alanine modified Bim-BH3 peptide. This peptide is allowed to complex with Bcl-xL-GST while exposed to UV light. The covalent heterodimer is purified and assessed for function before being used to immunize mice.

We prepared an immunogen consisting of a Bcl-xL-GST fusion protein bound with Bim-BH3 domain peptide. (FIG. 6). Though there is tight binding between the peptide and the protein it seemed likely that only a covalently attached peptide would remain bound during the immunization process. To make such a covalent heterodimer immunogen we prepared a series of Bim BH3 domain peptides with 4-benzoylpheylalanine (BPA) residues with replacing each of the sterically similar aromatic amino acids in the peptide one at a time. (FIG. 7). A series of such peptides were tested for binding affinities for Bcl-xL using fluorescence polarization and compared to the non-modified Bim BH3 peptide. The peptide that demonstrated the most similar binding affinity to the non-modified Bim BH3 peptide was chosen for covalent linking.

Coupling was performed by adding a 2 fold molar excess of BPA-Bim-BH3 to Bcl-xL GST and exposing to UV light for 8 hours. Following UV activation each of the different Bcl-xL Bim-BPA-BH3 covalent complexes were tested for physical features by gel electrophoresis, mass spectroscopy analysis. Unbound Bcl-xL GST was removed from the solution by passing over a Biotinylated-Bim BH3, Streptavidin-bead column. The flow through was prepared for immunization.

Monoclonal Antibody Development

Figure 8:
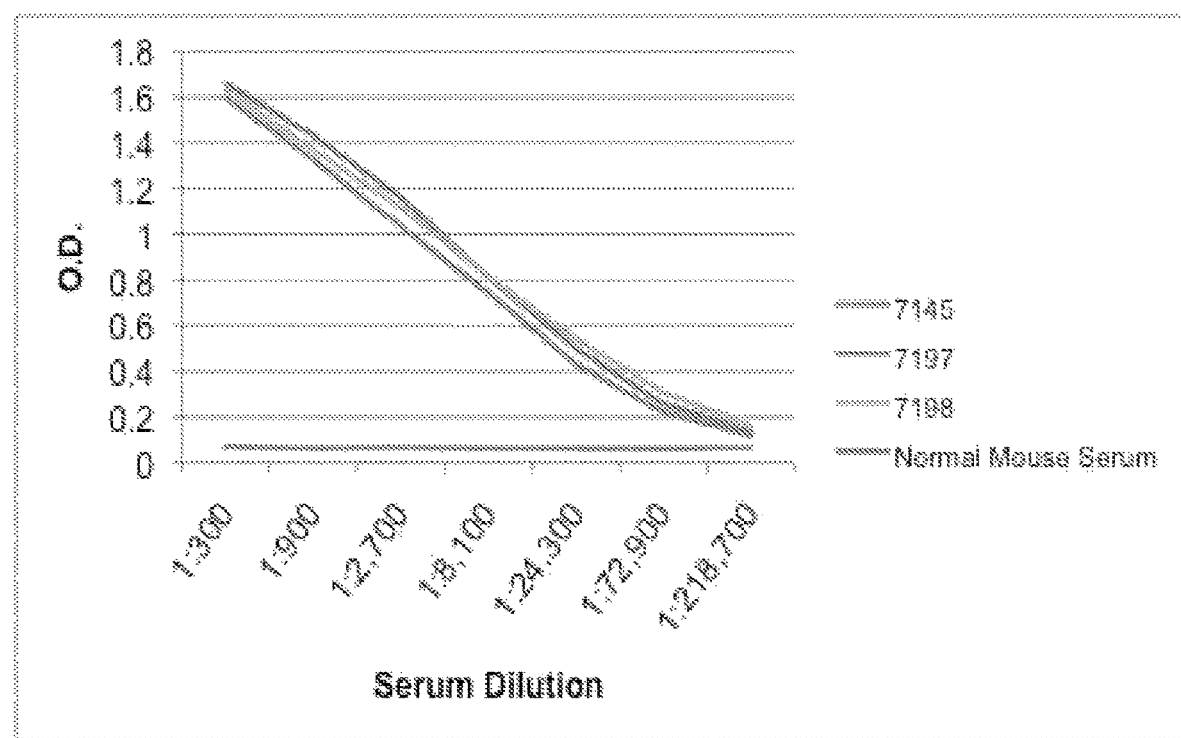
FIG. 8 shows the results of an ELISA of various dilutions of hybridoma clones 7146, 7197, and 7198.

HTP™ Mice (Abpro, Lexington Mass.) have been genetically engineered to produce a more sensitive immune response than mouse models. Due the broader epitope diversity of this response, it generates high affinity antibodies to the most traditionally difficult targets. MAbs were generated in mice using a rapid immunization protocol. Using a modified rapid immunization at multiple sites (RIMMS) protocol with the soluble GST-Bcl-xL/BIM, the immunized mice developed high levels of polyclonal IgG to the immunogen within 17 days of the first immunization. The lymph node cells isolated from the immunized animals were then fused with mouse myeloma cells for hybridoma generation. Use of an efficient hybridoma cloning protocol in combination with an ELISA screening procedure (see FIG. 8) allowed for early identification of stable hybridomas secreting anti-Bcl-xL/BIM IgG.

Mice were immunized with 100 ug GST-Bcl-xL/BIM protein and Complete Freund's Adjuvant (CFA). Subsequent injections every two or three days were with 100 ug immunogen and Incomplete Freund's Adjuvant (IFA). Immunized mice were titer tested for reactivity by ELISA. Mouse lymph cells were fused with murine myeloma cell lines and hybridomas were selected in HAT media.

Screening and Selection of Monoclonal Antibodies

Figure 9:
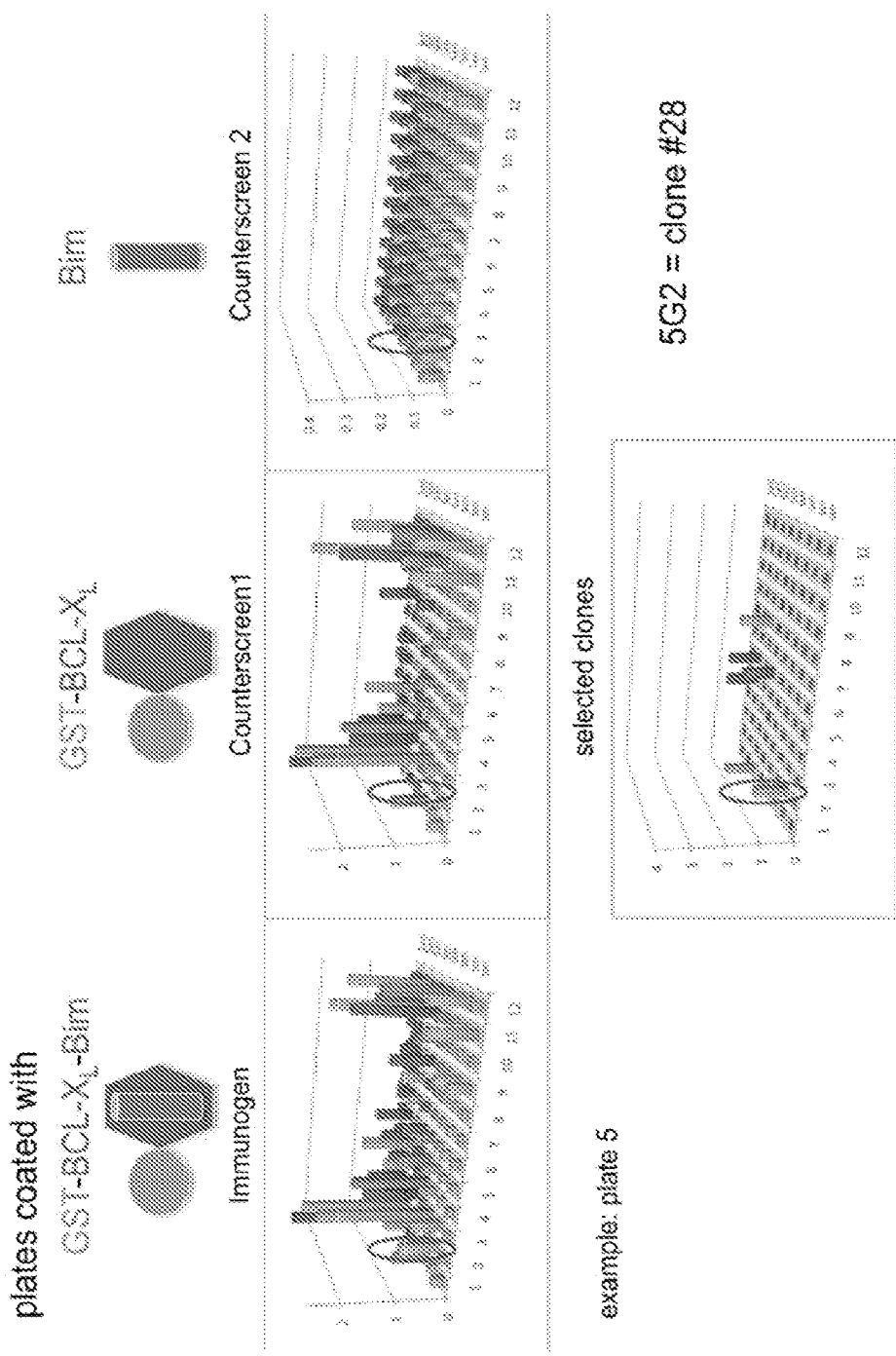
FIG. 9 is a schematic illustration depicting the screen/counterscreen of monoclonal antibodies derived from fusions. Eight 96-well plates=768 clones tested in ELISA assay plates coated with Bcl-XL-GST/Bim BH3 peptide conjugate, and counter screened against the Bcl-XL GST or Bim-BH3 peptide coated plates. From this, 39 selectively binding clones, were advanced for testing and subcloning.

Fusion hybridoma supernatants were screened for specific reactivity by ELISA. ELISA positive clones were subcloned to obtain monoclonal hybridomas of interest. Clones were ranked by relative affinity. Results were validated using purified GST-Bcl-xL fusion protein in an ELISA-based assay (FIG. 9). Eight 96-wells plates or 768 clones were tested in an ELISA assay.

Several identified MAbs specifically reacted with the Bcl-xL/BIM heterodimer protein without binding to protein or peptide alone. As evaluated by ELISA analysis, some MAbs displayed high affinities to heterodimer. Fifty clones were selected and 39 clones were still viable and positive in the pre-subclone screen.

A sandwich ELISA was used to determine the antibody concentration in the fusion clone supernatants. Thirty-one of the 39 clones turned out to be IgG class. All following assays were normalized to IgG concentration.

Covalent Heterodimer Assay

Figure 10A:
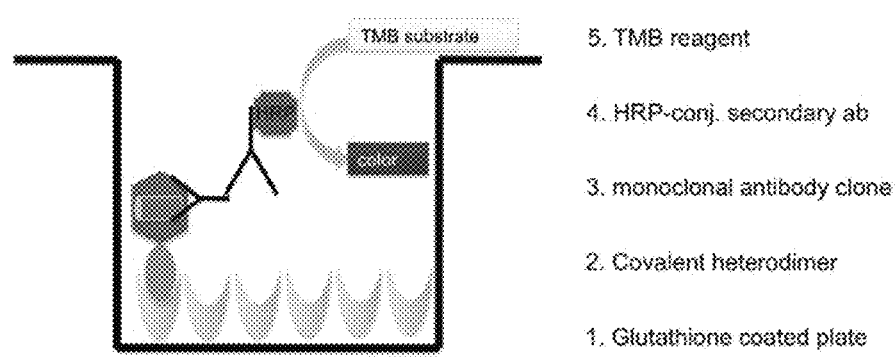
FIG. 10A and FIG. 10B show an assay in which covalent heterodimer was bound to Glutathione-coated ELISA plates and tested for binding of fusion clones to GST-Bcl-XL-BIM heterodimer. Panel A shows the set-up of reagents. Panel B shows the results for two dilutions of the heterodimer.
Figure 10B:
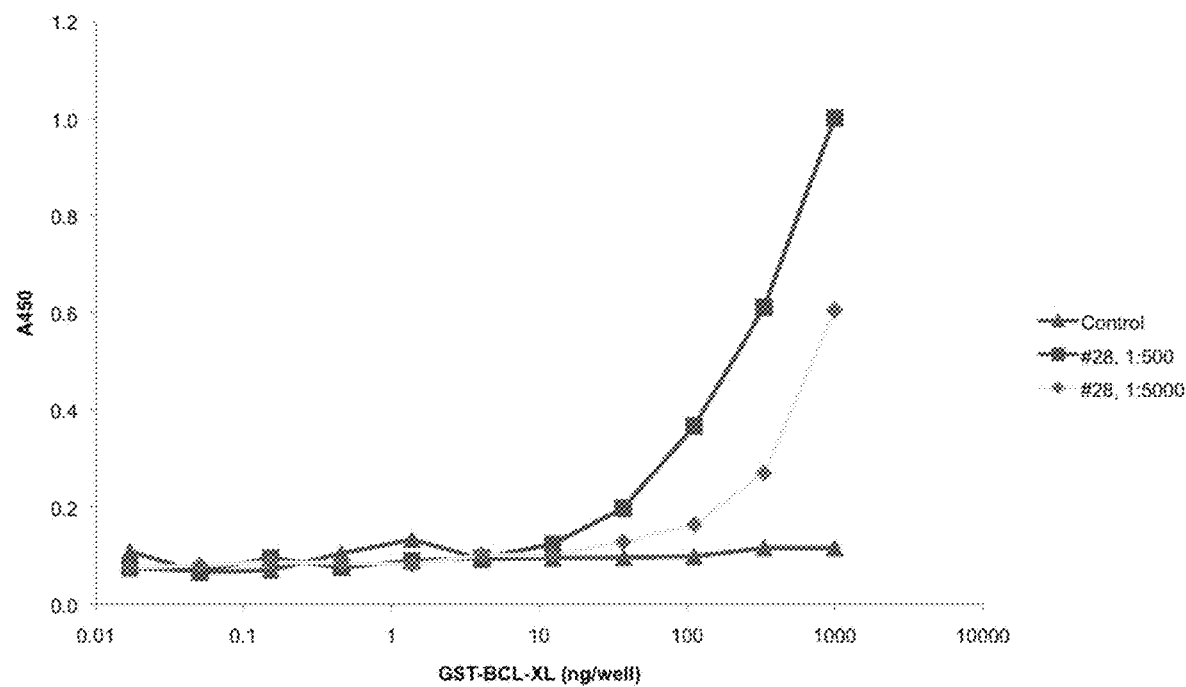

Supernatants from clones were tested binding activity by EILISA. Protein concentrations were normalized and a concentration series was tested. A representative experiment is shown in FIG. 10 and FIG. 10B. Briefly, a covalent heterodimer was bound to Glutathione-coated ELISA plates and tested for binding of fusion clones to GST-Bcl-XL-BIM heterodimer. FIG. 11A, FIG. 11B, FIG. 11C, and FIG. 11D show the heterodimer binding affinity ranked for all 31 IgG clones tested in this ELISA based assay.

Figure 12:
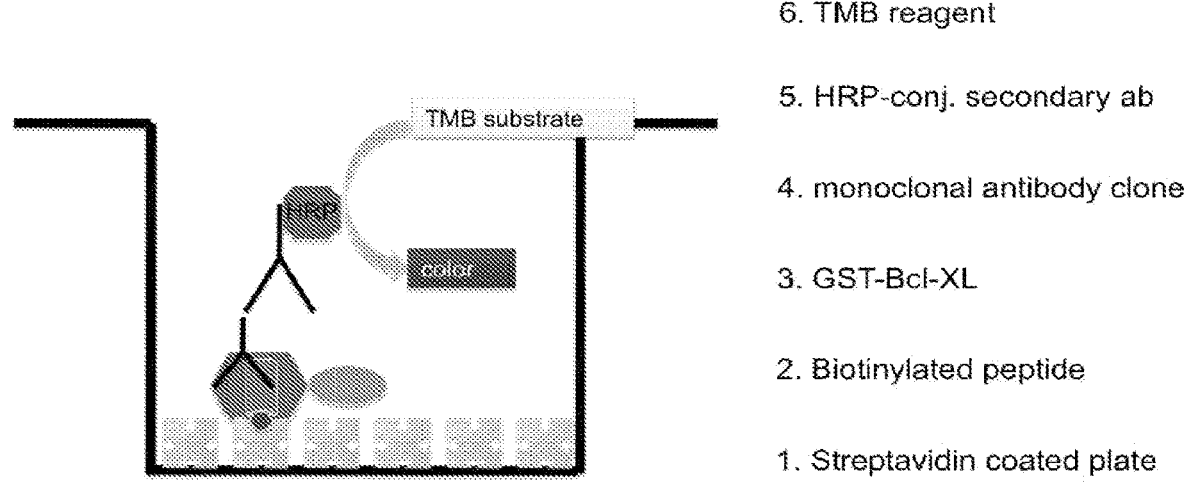
FIG. 12 shows an alternative strategy in which biotinylated peptide was bound to Streptavidin-coated plates and then incubated with the GST-Bcl-XL fusion proteins.
Figure 13B:
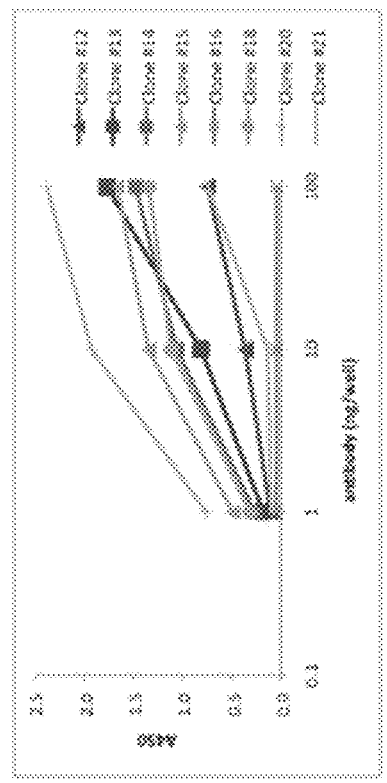
FIG. 13A, FIG. 13B, FIG. 13C, and FIG. 13D show the heterodimer binding affinity ranked for all 31 IgG clones tested in this ELISA assay.
Figure 13D:
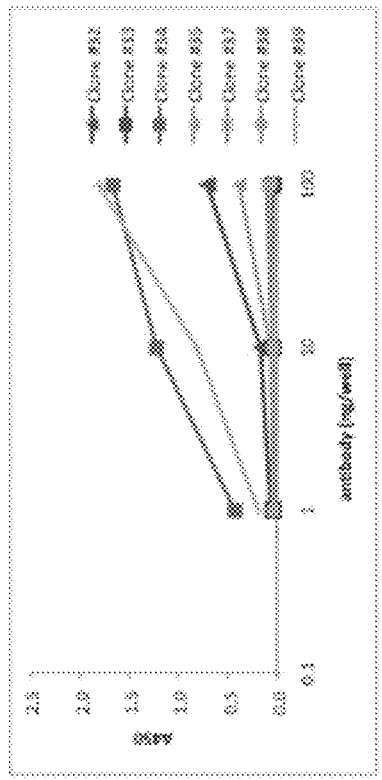
Figure 13A:
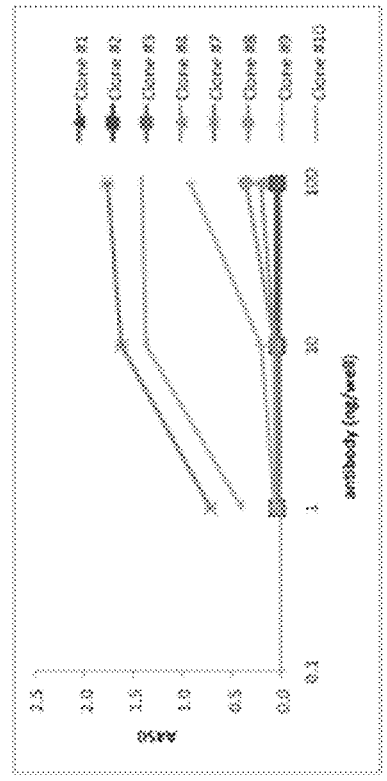
Figure 13C:
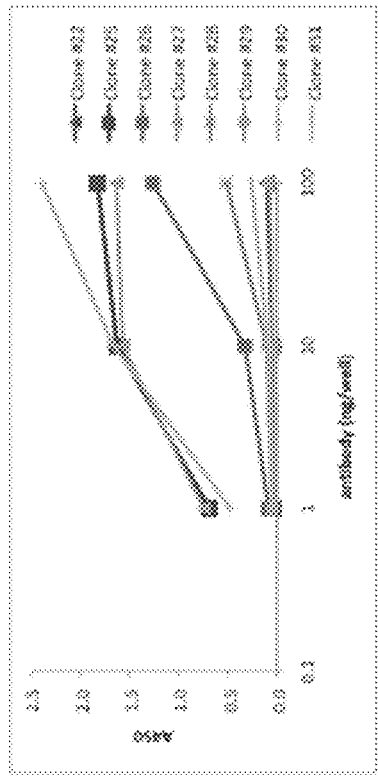

FIG. 12 shows a schematic of an alternative strategy where biotinylated peptide was bound to Streptavidin-coated plates and then incubated with the GST-Bcl-XL fusion proteins. FIG. 13A, FIG. 13B, FIG. 13C, and FIG. 13D show the heterodimer binding affinity ranked for all 31 IgG clones tested in this ELISA based assay.

Establishing Selective Recognition of BIM BH3 Induced Epitope

Figure 14:
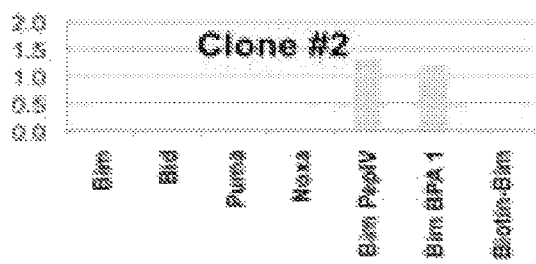
FIG. 14 shows the selective binding of Bim versus other peptides. GST-Bcl-XL fusion protein was added to Glutathione coated plates first, and subsequently clones were screened for specificity by adding non-modified pro-apoptotic BH3-only subfamily domain peptides. This figure shows an example of five different clones that showed specificity for BIM, but no specificity for BID peptide.
Figure 14:
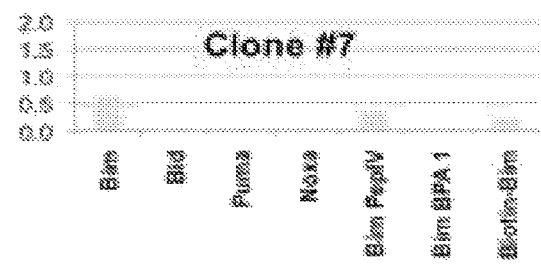
Figure 14:
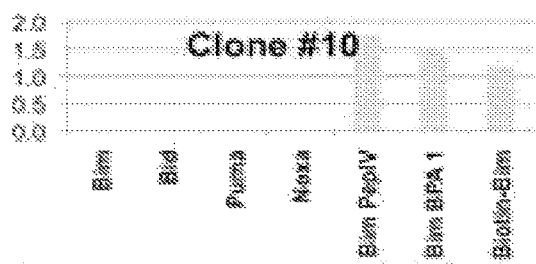
Figure 14:
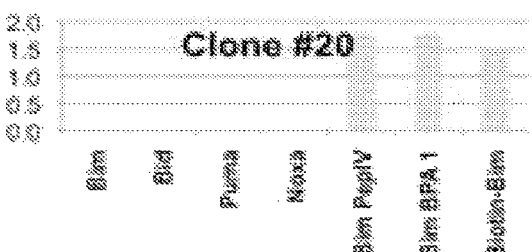
Figure 14:
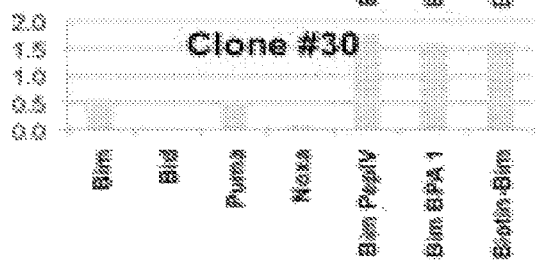
Figure 14:
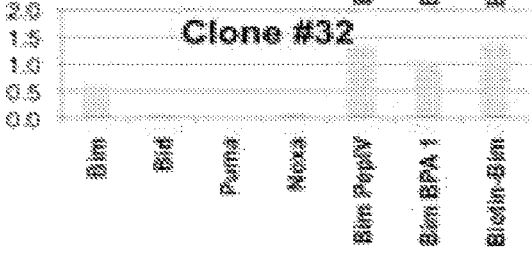

The results from the titrations of 31 clones were confirmed by binding to heterodimers formed by non-covalent interactions. In addition, this experiment examined the binding of clone supernatants to other BH3 only protein peptides, Bid, Puma, and Noxa as well as the BPA-Bim BH3 peptide, the native BIM BH3 peptide, the native BIM BH3 peptide with several flanking amino acids. As shown in FIG. 14, several clones demonstrated selective binging to the Bim-BH3 peptide over the Bid, Puma and Noxa peptides. Of these we preferred those that bound to each of the BIM BH3 peptides and we selected clone 32, now called Heterodimer, Bcl-xL Specific to Bim (hence forth referred to as HBXSB) as the parent clone for further study.

Establishing Selective Inhibition of BIM BH3 Induced Epitope

Figure 15:
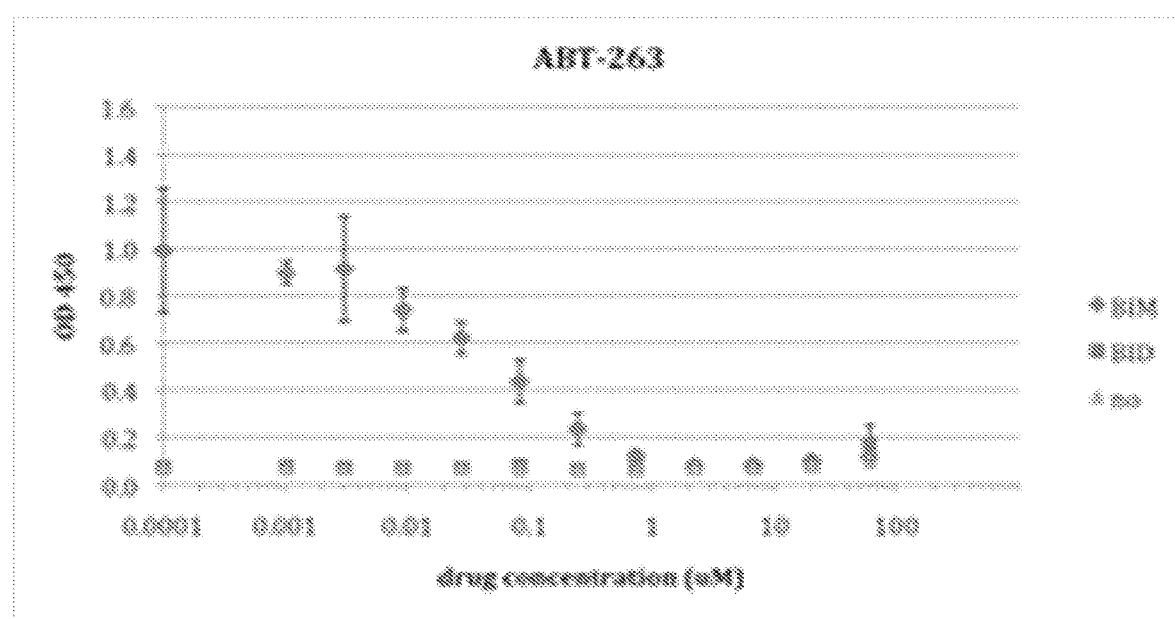
FIG. 15 shows the selective inhibition of HSBXB binding to heterodimer Bcl-XL/BIM-BH3 with BH3 mimetic Abt-263: In this assay, non-covalent Bcl-XL-GST/BIM-BH3 heterodimer was bound to Glutathione-coated ELISA plates and treated with ABT-263 (Navitoclax), a potent BCL2/Bcl-XL targeted compound. The compound was added to the ELISA plates after addition of peptides and before adding the monoclonal antibody. The Bib BH3 domain peptide was added as a negative control.

ABT-263 is a BH3 domain mimetic that competitively inhibits BH3 domain mediated binding. ABT-263 disrupts Bcl-2/Bcl-xL interactions with pro-death proteins (e.g., Bim), leading to the initiation of apoptosis within 2 hours post treatment (Tse et al., 2008). A dose-dependent inhibition of heterodimer antibody signal was observed in heterodimers formed with the BIM peptide. BID peptide or no peptide served as negative controls confirming a heterodimer specificity of the monoclonal antibody. The data in FIG. 15 demonstrates that displacement of the Bcl-xL bound BIM BH3 peptide is detected by HSBXB. A dose dependent inhibition of heterodimer antibody signal was observed with BIM peptide. BID peptide, or no peptide, served as negative controls confirming a heterodimer specificity of the monoclonal antibody.

Application of HSBXB to Fixed Cells

Figure 16A:
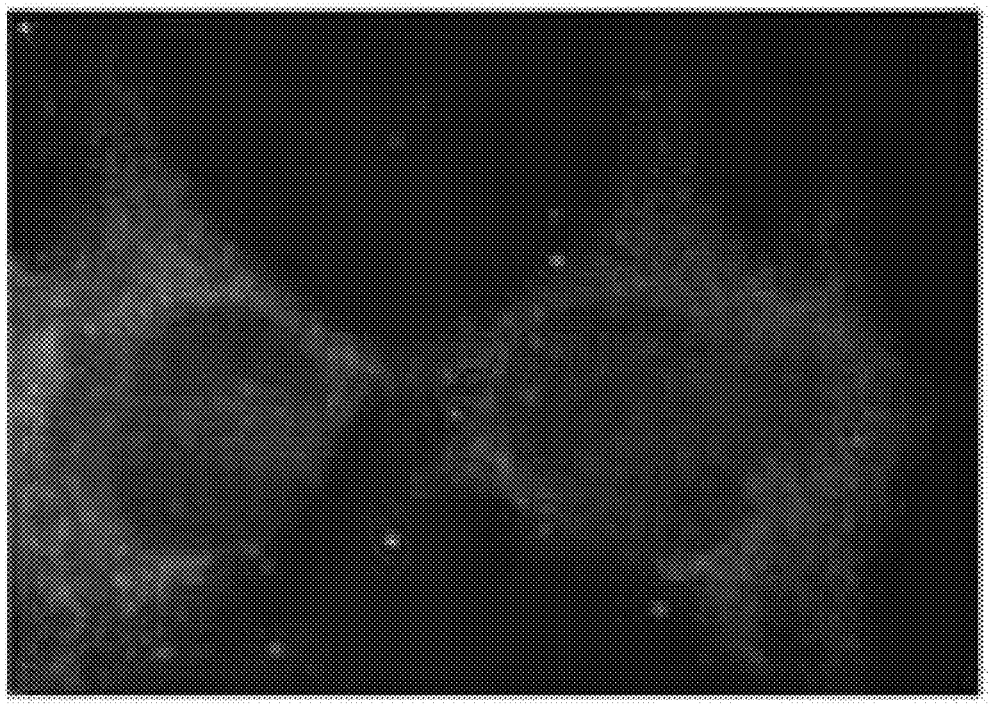
FIG. 16A and FIG. 16B show immunofluorescence microscopy for 6 clones selected for subcloning based on the combined ELISA results. Melanoma AUCC903N cells were either fixed with Methanol (Panel A) or with 4% paraformaldehyde and permeabilized with 0.2% TRITONX100 (Octylphenol Ethoxylate) (Panel B) and incubated with subclone #32. The cells were incubated with an Alexa488-conjugated goat anti-mouse antibody. Panel B shows an overlay with DAPI nuclear DNA stain. The mitochondrial staining is visible.
Figure 16B:
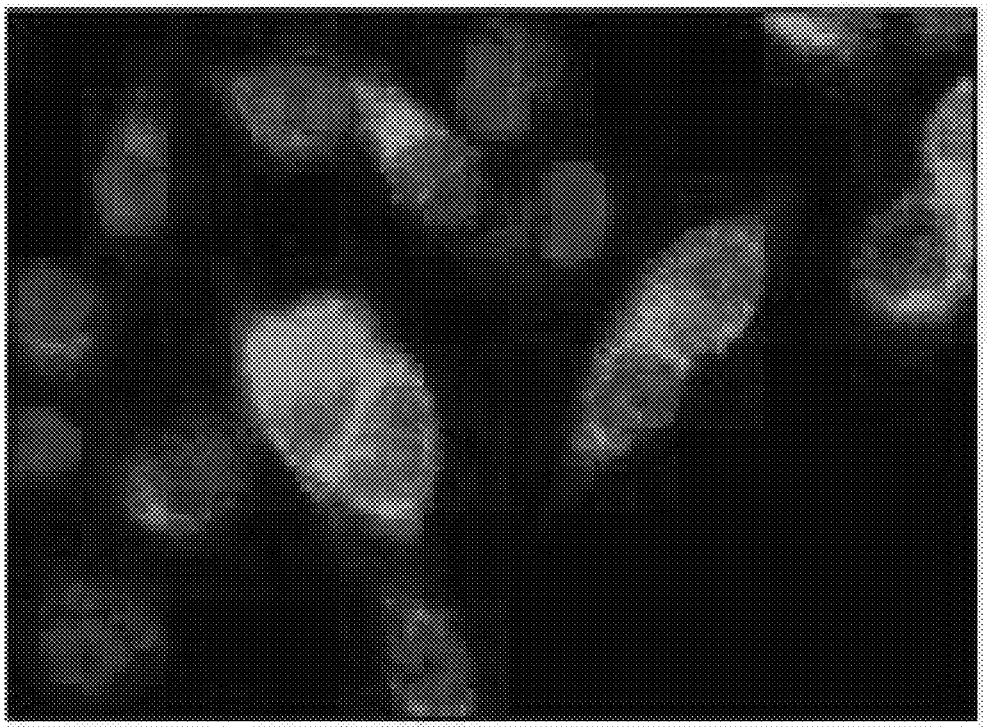

To demonstrate the utility of HSBXB as biomarker that could be used in fixed archived tumor samples we used immunofluorescence microscopy to test 6 of the clones (FIG. 16A and FIG. 16B). Melanoma AUCC903N cells were fixed with either methanol (Panel A) or 4% paraformaldehyde (Panel B), permeabilized with 0.2% TRITONX100 (Octylphenol Ethoxylate) and incubated with a subclone of HSBSX (#32). Then cells were incubated with an Alexa488-conjugated goat anti-mouse antibody.

Inhibition of HSBXB Binding With ABT 263 and Detection in Fixed Cells

We have determined that our novel imaging system would be well suited for quantitative signal analysis in fixed cells and solid tumor thin sections. The system provides several advantages over microscopy or high throughput western blotting. The detection system uses near-infrared (IR) fluorophores (670-1100 nm) that have a distinct advantage over visible dyes, in that very low background fluorescence at longer wavelengths provides an excellent signal-to-noise ratio. Common visible fluorophores cannot be used effectively for direct protein detection on membranes and in plastic plates because of their high background fluorescence in the visible range. In this system antibodies labeled with IR dyes at different wavelengths are used for detection of multiple targets. The imager simultaneously detects two distinct wavelengths. A scanning optical assembly carries two laser diodes that generate excitation light at 680 and 780 nm, as well as two avalanche photodiodes, which detect emitted fluorescence at 720 and 820 nm.

Figure 17A:
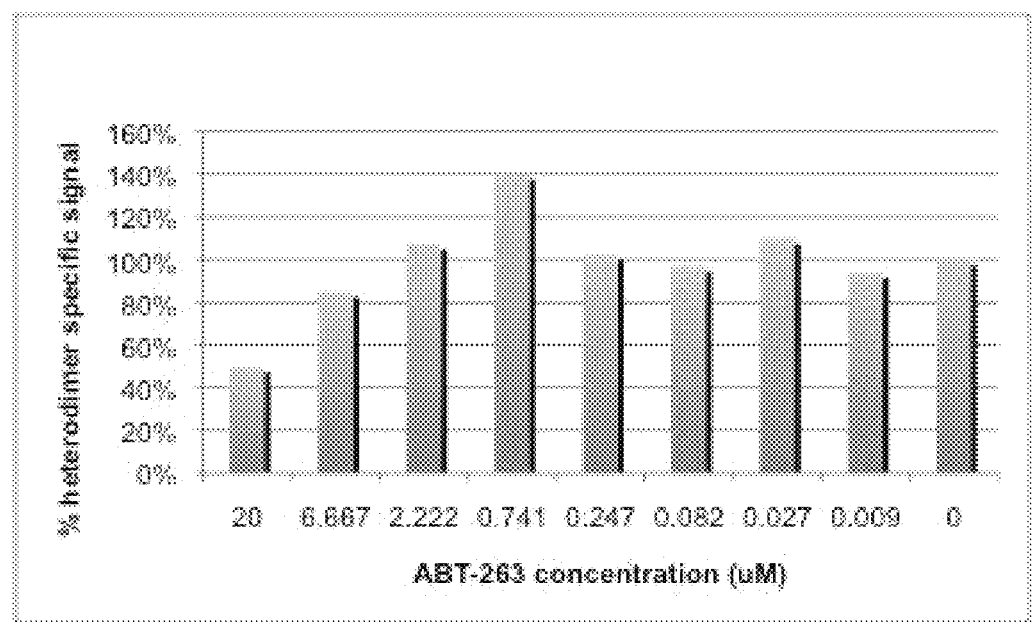
FIG. 17A and FIG. 17B shows HSBXB binding of Bcl-XL/BIM heterodimer in cells incubated with different concentrations of ABT-263. IRDye 800CW goat anti-mouse antibody was used for detecting the heterodimer specific mouse monoclonal antibody and IRDye 800CW Goat anti-rabbit antibody was used to detect the commercial Bcl-XL rabbit monoclonal antibody. Panel A is a bar graph, and Panel B is a line graph showing the percent heterodimer specific signal in relation to ABT-263 concentration.
Figure 17B:
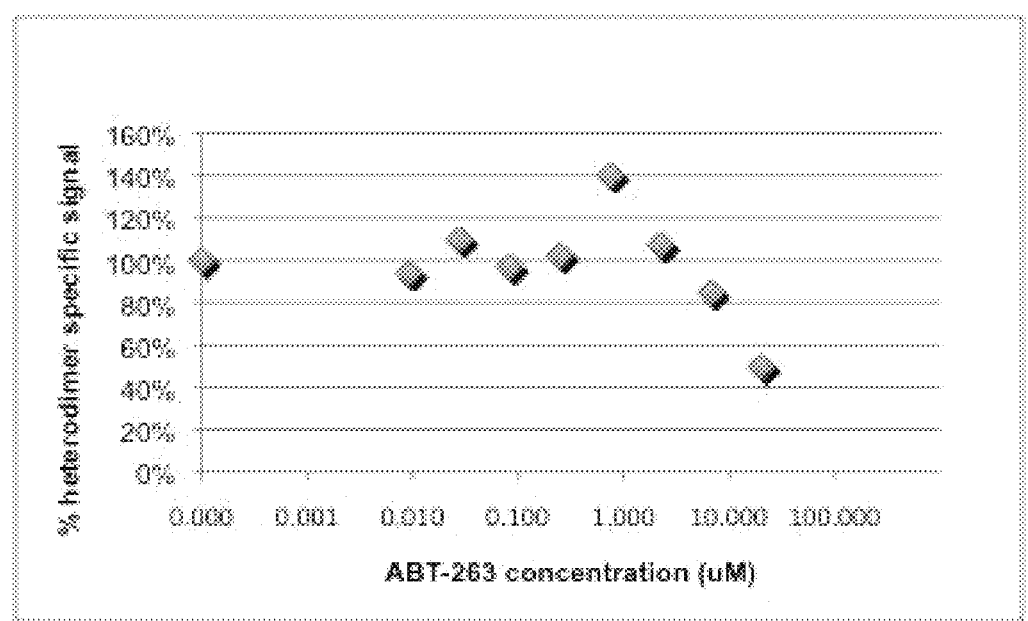

Using this system we have demonstrated that displacement of the Bcl-xL bound BIM BH3 peptide is detected by HSBXB in paraformaldehyde fixed cells. FIG. 17A and FIG. 17B demonstrates HSBXB binding of Bcl-XL/BIM heterodimer in cells incubated with different concentrations of ABT-263 to shows quantitative measurements of heterodimer in response to ABT-263 in SKBR3 cells. IRDye 800CW goat anti-mouse antibody was used for detecting the heterodimer specific mouse monoclonal antibody and IRDye 800CW Goat anti-rabbit antibody was used to detect the commercial Bcl-XL rabbit monoclonal antibody.

Inhibition and Enhancement of HSBXB and Detection by Flow Cytometry

Figure 18:
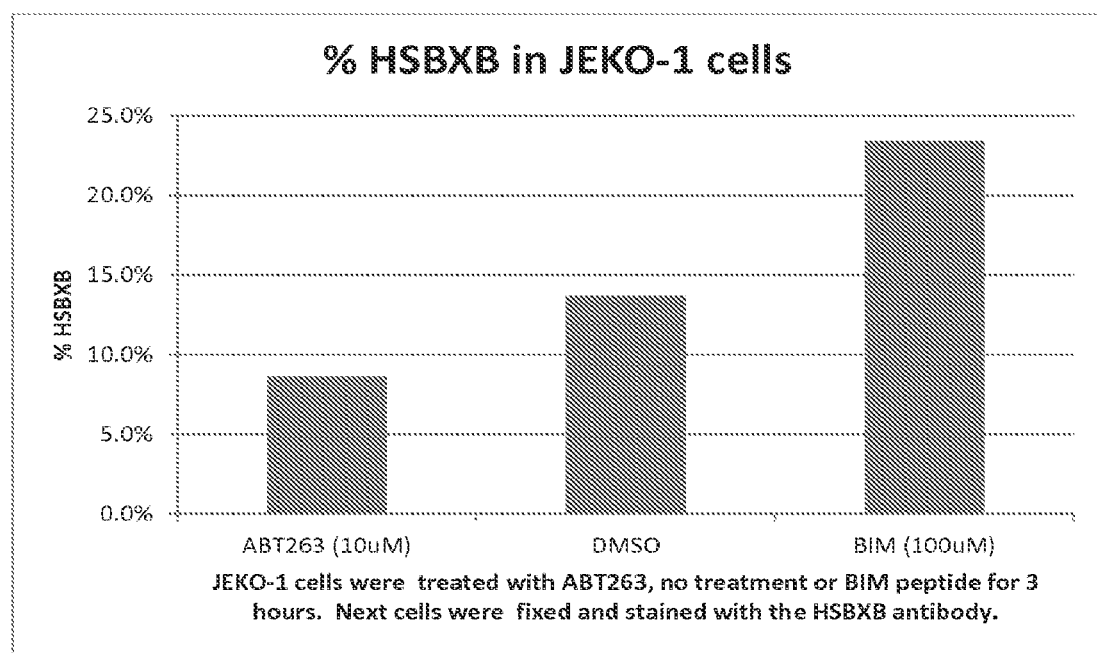
FIG. 18 shows a FACS readout in JEKO-1 cells which were treated with ABT263, no treatment or BIM peptide for 3 hours is represented positive signal is percentage of signal generated by the isotype (negative control).

We have established a method for intracellular staining with the Bcl-xL and the HSBXB antibodies and used that in several leukemia cell lines. As a positive control we pretreated with the Bim BH3 peptide at a concentration that achieve saturated binding to the endogenous Bcl-XL. This treatment is routinely used as a positive control for complete mitochondrial priming in our mitochondrial profiling AML test. As a negative control we pretreated with ABT 263 to displace Bim from Bcl-xL by the BH3, as we have established above this treatment diminished binding in in vitro assays and in our novel platform. The displacement of Bim by ABT263 results in MOMP as measured by the mitochondrial profiling assay (unpublished data). FIG. 18 shows that this displacement in measurable by flow cytometry using the HSBXB antibody. To enhance staining and to establish a positive control we added saturating amount of the Bim BH3 peptide to partially lysed cells. As a negative control we pretreated with BH3 mimetic compound, ABT 263 to displace Bim from Bcl-xL. In this experiment 5×10e6 JEKO 1 cells were suspended in Newmeyer buffer (Ryan et al Proc Natl Acad Sci USA 2010; 107:12895-900), digitonin (Sigma-Aldrich, St Louis Mo.) and treated with 100 uM Bim BH3 peptide; or ABT263 compound at 10 uM; or not treated. Cells were incubated on ice for 3 hours, and then washed and treated with clone 32 at 10 ug/ml for 20 minutes, washed again and stained with secondary goat anti-mouse IgG alexa-488. An IgG-2A isotype control was also prepared and run in parallel. Samples are analyzed on a FACS Canto II (BD Biosciences, San Jose Calif.) using the BD FACS Diva software.

EQUIVALENTS

The detailed description herein describes various aspects and embodiments of the invention, however, unless otherwise specified, none of those are intended to be limiting. Indeed, a person of skill in the art, having read this disclosure, will envision variations, alterations, and adjustments that can be made without departing from the scope and spirit of the invention, all of which should be considered to be part of the invention unless otherwise specified. Applicants thus envision that the invention described herein will be limited only by the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

What is claimed is:

1. A method for predicting a patient's sensitivity to a cancer treatment, comprising:
   a) isolating a patient sample comprising a cancer cell or specimen from said patient;
   b) contacting said cancer cell or specimen with one or more fluorescently-labelled monoclonal IgG antibodies that specifically bind to an anti-apoptotic heterodimer; wherein the heterodimer comprises a first member of the Bcl-2 family and a second member of the Bcl-2 family, wherein the first Bcl-2 family member is BIM, and the second Bcl-2 family member is selected from Mcl-1, Bcl-XL, and Bcl-2;
   c) detecting an immunofluorescent signal from the one or more fluorescently-labelled antibodies, wherein the presence of the immunofluorescent signal indicates binding of the fluorescently-labelled antibody to the heterodimer, thereby detecting the heterodimer in the patent sample;
   d) determining a correlation between the antibody binding to the heterodimer in said cancer cell or specimen and the sensitivity of said cell or specimen to said treatment; and
   e) classifying the patient for likelihood of clinical response to one or more cancer treatments, wherein the presence of the heterodimer in the patient sample indicates the patient is likely to be sensitive to the cancer treatment.

2. The method of claim 1, wherein the cancer is a hematologic cancer.

3. The method of claim 2, wherein the hematologic cancer is selected from acute myelogenous leukemia (AML), multiple myeloma, follicular lymphoma, acute lymphoblastic leukemia (ALL), chronic lymphocytic leukemia, and non-Hodgkin's lymphoma.

4. The method of claim 1, wherein the cancer is a solid tumor cancer.

5. The method of claim 4, wherein the solid tumor cancer is selected from non-small lung cell carcinoma, ovarian cancer, and melanoma.

6. The method of claim 1, wherein the specimen is a biopsy selected from a frozen tumor tissue specimen, cultured cells, circulating tumor cells, and a formalin-fixed paraffin-embedded tumor tissue specimen.

7. The method of claim 1, further comprising treating the patient if the patient is likely to be sensitive to the cancer treatment.

8. The method of claim 7, further comprising treating the patient with a different cancer treatment if the patient is likely to not be sensitive to the cancer treatment.

9. The method of claim 8, wherein the cancer treatment is one or more of anti-cancer drugs, chemotherapy, antagonist of an anti-apoptotic protein, surgery, adjuvant therapy, and neoadjuvant therapy.

10. The method of claim 8, wherein the cancer treatment is one or more of a second mitochondrial-derived activator of caspase (SMAC) mimetic, BH3 mimetic, proteasome inhibitor, histone deacetylase inhibitor, glucocorticoid, steroid, monoclonal antibody, antibody-drug conjugate, or thalidomide derivative.

11. The method of claim 8, wherein the treatment blocks formation of the heterodimer detected.

* * * * *